United States Patent
Zhang et al.

(10) Patent No.: US 11,691,953 B2
(45) Date of Patent: Jul. 4, 2023

(54) COMPOUND AS PPAR AGONIST AND APPLICATION THEREOF

(71) Applicant: USA Elixiria Biotech Inc., Hartsdale, NY (US)

(72) Inventors: Lihai Zhang, Hartsdale, NY (US); Min Hu, Heilongjiang (CN)

(73) Assignee: USA Elixiria Biotech Inc.

( * ) Notice: Subject to any disclaimer, the term of this patent is extended or adjusted under 35 U.S.C. 154(b) by 0 days.

(21) Appl. No.: 16/921,102

(22) Filed: Jul. 6, 2020

(65) Prior Publication Data

US 2020/0331868 A1 Oct. 22, 2020

Related U.S. Application Data

(63) Continuation-in-part of application No. PCT/CN2019/072302, filed on Jan. 18, 2019.

(51) Int. Cl.
| | | |
|---|---|---|
| C07D 267/14 | (2006.01) | |
| C07C 49/653 | (2006.01) | |
| C07D 215/227 | (2006.01) | |
| C07D 311/22 | (2006.01) | |
| C07D 311/76 | (2006.01) | |
| C07D 265/36 | (2006.01) | |
| C07D 277/34 | (2006.01) | |
| C07D 209/88 | (2006.01) | |
| C07D 333/50 | (2006.01) | |
| C07D 495/08 | (2006.01) | |
| C07D 233/36 | (2006.01) | |
| C07D 241/08 | (2006.01) | |

(52) U.S. Cl.
CPC .......... *C07D 267/14* (2013.01); *C07C 49/653* (2013.01); *C07D 209/88* (2013.01); *C07D 215/227* (2013.01); *C07D 233/36* (2013.01); *C07D 241/08* (2013.01); *C07D 265/36* (2013.01); *C07D 277/34* (2013.01); *C07D 311/22* (2013.01); *C07D 311/76* (2013.01); *C07D 333/50* (2013.01); *C07D 495/08* (2013.01)

(58) Field of Classification Search
None
See application file for complete search history.

(56) References Cited

U.S. PATENT DOCUMENTS

| | | | |
|---|---|---|---|
| 2009/0054417 A1* | 2/2009 | Michellys | A61P 1/16 514/249 |
| 2014/0275060 A1 | 9/2014 | Menaldino et al. | |

FOREIGN PATENT DOCUMENTS

WO    WO 97/23214 A1    7/1997

OTHER PUBLICATIONS

Chemical Abstract Registry No. 1452760-28-9, indexed in the Registry File on STN CAS Online Sep. 20, 2013.*
Chemical Abstract Registry No. 1336953-22-0, indexed in the Registry File on STN CAS Online Oct. 17, 2011.*
Sairam et al., Three Dimensional Pharmacophore Modelling of Monoamine oxidase-A (MAO-A) inhibitors. International Journal of Molecular Sciences, 2007, 8, 894-919.*
Federal Register, published on 2011, vol. 76, No. 27, p. 7166.*
Chemical Abstract Registry No. 1416979-97-9, indexed in the Registry File on STN CAS Online Jan. 18, 2013.*
Manley-King, Clarina I. et al., "Inhibition of monoamine oxidase by selected C5- and C6-substituted isatin analogues"; Bioorganic & Medicinal Chemistry, 19:261-274 (2011).
PCT Notification (Form PCT/ISA/210) in Chinese language for International Application No. PCT/CN2019/072302.
PCT Notification (Form PCT/ISA/237) in Chinese language for International Application No. PCT/CN2019/072302.
Grammes, C, et al. The PPARγ agonist pioglitazone crosses the blood-brain barrier and reduces tumor growth in a human xenograft model, Cancer Chemother Pharmacol, 71:929-936 (2013).

* cited by examiner

*Primary Examiner* — Po-Chih Chen
(74) *Attorney, Agent, or Firm* — Locke Lord LLP

(57) ABSTRACT

The present invention provides compounds as PPAR agonists and their application, involving a new class of peroxisome proliferator-activated receptor (PPAR) gamma receptor agonist, which can inhibit the production of mitochondrial reactive oxygen species, and most of which can readily cross the blood-brain barrier. The present invention also includes pharmaceutical uses of the compounds.

6 Claims, 6 Drawing Sheets

COMPOUND AS PPAR AGONIST AND APPLICATION THEREOF

This application is a continuation-in-Part of International Application Number PCT/CN2019/072302, filed Jan. 18, 2019, which claims the benefit of Chinese Patent Application Number CN 201810054428.2, filed Jan. 19, 2018, all of which are hereby incorporated by reference in their entireties.

TECHNICAL FIELD

The invention belongs to the field of chemical medicine, and encompasses compounds, methods of preparing compounds, pharmaceutical compositions and medicaments of compounds, especially novel compounds that can cross the blood-brain barrier (BBB), which are agonists of peroxisome proliferator-activated receptor gamma (PPARγ). The invention also relates to their preparation and their use in pharmaceutical compositions for human or veterinary medicine, or use in a cosmetic composition.

BACKGROUND ART

PPARγ agonist drugs currently sold on the market are mainly used to treat diabetes. Most of them are thiazolidinediones (TZD), including but not limited to pioglitazone and rosiglitazone. These substances can activate peroxisome proliferator-activated receptor (PPAR) and, then PPAR bind to the DNA sequence of peroxisome proliferator hormone response elements (PPRE).

TZD class of PPARγ agonists taken by animals at high doses (greater than 100 mg/kg) were found to have a role in increasing klotho protein in the nervous system. Since 2005, it was found in many experiments that klotho protein has anti-aging and anti-dementia treatment effects. Life expectancy of mice with more klotho protein was extended by 30%, and they were healthier and smarter; Mice with lack of this protein showed many signs similar to human aging, including but not limited to cognitive decline and reduced synapses. Human studies have shown that people with more klotho protein had reduced risk of dementia. Klotho is mainly produced by the kidneys, circulates in the blood like hormones, and protects the kidneys as well as heart. So increasing of Klotho protein also has the potential to treat kidney and cardiovascular diseases.

TZD class of PPARγ agonists taken by animals at high doses (greater than 300 mg/kg) was found to control mitochondrial target protein(s), and relieve the neuropathic pains. In vitro studies identified several possible mitochondrial target proteins, including but not limited to complex I in respiratory chain, mitochondrial pyruvate carrier (MPC), mitoNEET, etc. Through these proteins, PPARγ agonists promote mitochondrial biosynthesis, inhibit the production of reactive oxygen species (ROS), and consequently treat many diseases, such as neurological disorders, metabolic diseases, etc.

However, the PPARγ agonist on the market has poor BBB penetration, which causes two limitations:

Limitation 1: Low Brain Bioavailability

Currently known PPARγ agonists are very difficult to penetrate the BBB. Although in vitro cell experiments have shown their potential to treat and/or prevent some neurological disorders and brain cancer. However, animal study indicated that in the case of high oral doses (10 mg/kg body weight), Rosiglitazone concentration in the brain is only about 0.7 micromole/L, still below its minimum concentration needed to treat brain cancer (1-10 micromole/L). See reference 1: Grommes, C, et al. The PPARγ agonist pioglitazone crosses the blood-brain barrier and reduces tumor growth in a human xenograft model [J]. Cancer Chemother Pharmacol 2013, 71(4): 929-936. This is because the human BBB prevents PPARγ agonists from entering the neural tissue of the brain. The blood brain barrier is formed by endothelial cells of the capillary wall, astrocyte end-feet ensheathing the capillary, and pericytes embedded in the capillary basement membrane, Many blood compounds, including but not limited to almost all macromolecular drugs and 98% of small molecule drugs, have difficulty crossing the blood-brain barrier into the brain parenchyma, leading to the extremely low dose of drugs that cross the BBB, encumber PPARγ agonists from exerting their effects in the nerve tissue of the brain or elsewhere, and hamper the efficacy. It is therefore necessary to increase the concentration of PPARγ agonists in the brain.

Limitation 2: Intolerable High Systemic Dose

Although systemic administration of clinically used pioglitazone and rosiglitazone capable or likely to treat and/or prevent many diseases, the dosage and time of administration must always be strictly controlled. If the dose is too high or taken for a long time, there will be some side effects. The main side effects of systemic administration include: Edema, fracture of bone, hepatotoxicity. These side effects limit high-dose administration to treat and/or prevent many chronic or semi-chronic diseases, e.g., Alzhmer's disease.

Reduced doses can significantly reduce the incidence of side effects. If PPARγ agonists can enter the brain tissue readily in large amounts, the dose of administration can be reduced, thus reducing the extent to which other organs and tissues of the human body are exposed to PPARγ agonists or their analogs, and consequently the side effects will be reduced. This is a two-pronged solution. However, there is currently a lack of PPARγ agonists with strong BBB permeability.

Therefore, there is a need in the art for PPARγ agonists with high blood-brain barrier permeability, related methods of administration and drugs.

Contents of the Invention

The present invention aims to provide new PPARγ agonists that can cross the blood-brain barrier and their use.

In the first aspect, the present invention provides compounds of formula (I) or pharmaceutically acceptable salts, solvates, prodrugs or metabolites thereof:

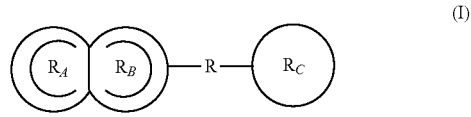

(I)

Among them, cyclic $R_A$ contains carbonyl or amide groups, which are saturated or unsaturated $C_{5-12}$ carbocyclic ring or $C_{5-12}$ heterocyclic ring that are optionally substituted by any one or more $R^a$;

cyclic $R_B$ is $C_{3-8}$ cycloalkyl, $C_{3-8}$ saturated cycloalkyl, $C_{3-8}$ unsaturated cycloalkyl, $C_{6-12}$ fused heterocyclic, $C_{6-12}$ aryl, $C_{6-12}$ heteroaryl optionally substituted by one or more $R^b$; or there is no cyclic $R_B$;

cyclic $R_C$ is $C_{3-8}$ cycloalkyl, $C_{3-8}$ saturated heterocycloalkyl, $C_{3-8}$ unsaturated heterocycloalkyl, $C_{6-10}$ aryl and C6-10 heteroaryl optionally substituted by one or more $R^C$;

R is $C_{1-12}$ alkyl, $C_{2-8}$ alkenyl, $C_{2-8}$ alkynyl, $C_{3-6}$ cycloalkyl and $C_{3-6}$ heterocycloalkyl which are optionally substituted by one or more $R^1$ or connected by one or more $R^1$;

among them, $R^1$, $R^a$, $R^b$ or $R^C$ can be independently selected from hydrogen atoms, halogen, hydroxyl, nitro, cyano, isocyanide, sulfonyl, $C_{1-6}$ alkyl, $C_{1-6}$ cycloalkyl, $C_{1-6}$ heterocyclyl, $C_{2-8}$ alkenyl, $C_{2-8}$ alkynyl, $C_{1-6}$ alkoxy, halogenated $C_1$-$C_6$ alkyl, halogenated $C_1$-$C_6$ alkoxy, halogenated $C_1$-$C_6$ cycloalkyl, $C_{1-6}$ alkylthio, $C_{1-6}$ alkylcarbonyl, $C_{1-6}$ alkoxycarbonyl, bis($C_{1-6}$ alkyl) amino, $C_{2-6}$ alkoxycarbonyl, $C_{2-6}$ alkylthiocarbonyl, amino, $C_{1-6}$ alkylamino, bis($C_{1-6}$ alkyl) amino, carbamoyl, $C_{1-6}$ alkylcarbamoyl, bis($C_{1-6}$ alkyl) carbamoyl, bis($C_{1-6}$ alkyl) $C_{2-6}$ alkylcarbamoyl, sulfamoyl, $C_{1-6}$ alkylsulfamoyl, bis($C_{1-6}$ alkyl) sulfamoyl, bis ($C_{1-6}$ alkyl) amino, $C_{2-6}$ alkylsulfamoyl, $C_{1-6}$ alkylsulfonyl, $C_{1-6}$ alkylsulfinyl, $C_{1-6}$ alkyl sulfonyl sulfonyl, bis($C_{1-6}$ alkyl) phosphono, hydroxyl $C_{1-6}$ alkyl, hydroxycarbonyl $C_{1-6}$ alkyl, $C_{1-6}$ alkoxyl $C_{1-6}$ alkyl, $C_{1-6}$ alkylsulfonyl $C_{1-6}$ alkyl, $C_{1-6}$ alkylsulfinyl $C_{1-6}$ alkyl, $C_{1-6}$ alkylthiocarbonyl $C_{1-6}$ alkyl, bis($C_{1-6}$ alkyl) phosphono $C_{1-6}$ alkyl, hydroxyl $C_{2-6}$ alkoxy, $C_{1-6}$ alkoxy $C_{2-6}$ alkoxy, amino $C_{1-6}$ alkyl, $C_{1-6}$ alkylamino $C_{1-6}$ alkyl, bis($C_{1-6}$ alkyl) amino $C_{1-6}$ alkyl, bis($C_{1-6}$ alkyl) aminoacetyl, amino $C_{2-6}$ alkoxy, $C_{1-6}$ alkylamino $C_{2-6}$ alkoxy, bis($C_{1-6}$ alkyl) amino $C_{2-6}$ alkoxy, hydroxy $C_{2-6}$ alkylamino, $C_{2-6}$ alkoxy $C_{2-6}$ alkylamino, amino $C_{2-6}$ alkylamino, $C_{1-6}$ alkylamino $C_{2-6}$ alkylamino, bis($C_{1-6}$ alkyl) amino $C_{2-6}$ alkylamino, $C_{5-10}$ aryl, $C_{5-10}$ heteroaryl group;

In a preferred embodiment, the compounds are (E)-6-(4-(4-ethylphenyl) but-1-en-1-yl)-2,3-dihydro-1H-inden-1-one; (E)-7-(4-(4-ethylphenyl)but-1-en-1-yl)-3,4-dihydroquinoline-2(1H)-one; (E)-6-(4-(4-methyl(Oxyphenyl)but-1-en-1-yl)-2,3-dihydro-1H-indene-1-one; (E)-6-(4-(3-methoxyphenyl)butane-1-en-1-yl)-2,3-dihydro-1H-inden-1-one; (E)-6-(4-(5-ethylpyridin-2-yl)but-1-ene(1-1-yl)-2,3-dihydro-1H-inden-1-one.

In another preferred embodiment, cyclic $R_C$ is preferred to be $C_{6-10}$ aryl and $C_{6-10}$ heteroaryl optionally substituted by one or more $R^C$, in which $R^C$ is $C_{1-6}$ alkyl.

In another preferred embodiment, R is $C_{1-12}$ alkyl and $C_{2-8}$ alkenyl groups optionally substituted by one or more $R^1$s or connected by one or more $R^1$s, where $R^1$ is one group selected from hydrogen atoms, halogens, hydroxyl, nitro, cyano, sulfonate, $C_{5-10}$ aryl and $C_{5-10}$ heteroaryl groups In another preferred embodiment, the total number of oxygen atoms and nitrogen atoms in the compounds is 1 to 4, with 1 to 3 being more preferred.

In another preferred embodiment, the total number of sulfur atoms in the compounds is 0 to 2, with 0 to 1 being more preferred.

In another preferred embodiment,

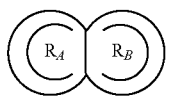

is selected from:

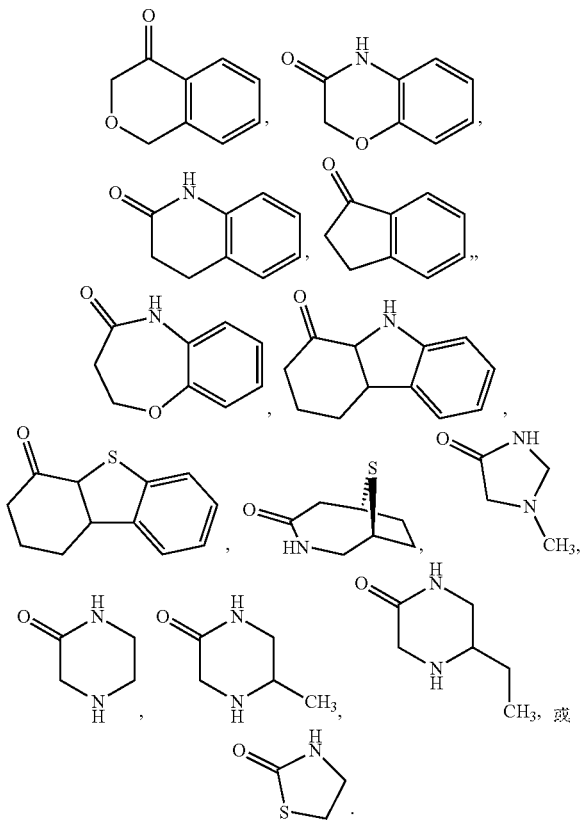

In another preferred embodiment, the compounds provided by the present invention is selected from those listed in Table 2:

(E)-6-(4-(4-ethylphenyl)but-1-en-1-yl)-2,3-dihydro-1H-inden-1-one;
(E)-7-(4-(4-ethylphenyl)but-1-en-1-yl)-3,4-dihydroquinolin-2(1H)-one;
7-(4-(4-ethylphenyl)butyl)-3,4-dihydroquinolin-2(1H)-one;
(E)-6-(4-(4-ethylphenyl)but-1-en-1-yl)chroman-4-one;
7-(4-(4-ethylphenyl)butyl)chroman-4-one;
(E)-7-(4-(4-ethylphenyl)but-1-en-1-yl)chroman-4-one;
(E)-8-(4-(4-ethylphenyl)but-1-en-1-yl)-2,3-dihydrobenzo [b][1,4]oxazepin-4(5H)-one;
8-(4-(4-ethylphenyl)butyl)-2,3-dihydrobenzo[b][1,4]oxazepin-4(5H)-one;
6-(6-(4-ethylphenyl)hexyl) isochroman-4-one;
(E)-6-(4-(4-ethylphenyl)but-1-en-1-yl)-2H-benzo[b][1,4] oxazin-3(4H)-one;
6-(4-(4-ethylphenyl)butyl)-2H-benzo[b][1,4]oxazin-3(4H)-one;
(E)-7-(4-(4-ethylphenyl)but-1-en-1-yl)-2,3,4,4a,9,9a-hexahydro-1H-carbazol-1-one;
(4aR,9aR)-7-(4-(4-ethylphenyl)butyl)-2,3,4,4a,9,9a-hexahydro-1H-carbazol-1-one;
(E)-7-(4-(4-ethylphenyl)but-1-en-1-yl)-1,2,3,9b-tetrahydrodibenzo[b,d]thiophen-4(4aH)-one;
(4aR,9bR)-7-(4-(4-ethylphenyl)butyl)-1,2,3,9b-tetrahydrodibenzo[b,d]thiophen-4(4aH)-one;
(1S,6R,8R)-8-(5-(4-ethylphenyl)pentyl)-9-thia-3-azabicyclo[4.2.1]nonan-4-one;
(E)-2-(3-(3-(4-ethylphenyl)prop-1-en-1-yl)benzyl)-1-methylimidazolidin-4-one;

(2R)-2-((3-(3-(4-ethylphenyl)propyl)phenyl)methyl)-1-methylimidazolidin-4-one;
(E)-6-(3-(3-(4-ethylphenyl)prop-1-en-1-yl)benzyl)piperazin-2-one;
(6S)-6-((3-(3-(4-ethylphenyl)propyl)phenyl)methyl)piperazin-2-one;
(5S,6S)-5-ethyl-6-((2S)-8-(4-ethylphenyl)-2-methyloctyl)piperazin-2-one;
(E)-6-(4-(4-ethylphenyl)but-1-en-1-yl)isochroman-4-one;
6-(4-(4-ethylphenyl)butyl)isochroman-4-one;
(E)-6-(4-(4-ethylphenyl)but-1-en-1-yl)-5-fluoro-2,3-dihydro-1H-inden-1-one:
(E)-6-(4-(4-ethylphenyl)but-1-en-1-yl)-5-(18F)fluoro-2,3-dihydro-1H-inden-1-one;
(E)-6-(3-(4-ethylphenoxy)prop-1-en-1-yl)-2,3-dihydro-1H-inden-1-one;
(E)-6-(4-(4-melhoxyphenyl)but-1-en-1-yl)-2,3-dihydro-1H-inden-1-one;
(E)-6-(3-(4-methoxyphenoxy)prop-1-en-1-yl)-2,3-dihydro-1H-inden-1-one;
(E)-6-(4-(5-ethylpyridin-2-yl)but-1-en-1-yl)-2,3-dihydro-1H-inden-1-one:
(E)-6-(4-(3-methoxyphenyl)but-1-en-1-yl)-2,3-dihydro-1H-inden-1-one;
(E)-6-(6-(4-ethylphenyl)hex-1-en-1-yl)-2,3-dihydro-1H-inden-1-one;
(E)-2-(3-(3-(4-ethylphenyl) prop-1-en-1-yl)benzyl)imidazolidin-4-one;
2-(3-(3-(4-ethylphenyl)propyl)benzyl)imidazolidin-4-one;
6-((1E)-4-(3-ethylphenyl)but-1-en-1-yl)-2,3-dihydro-1H-inden-1-one;
6-((1E)-5-(2-methyl-5-phenyl-1H-pyrrol-1-yl)pent-1-en-1-yl)-2,3-dihydro-1H-inden-1-one;
6-((1E)-4-(4-phenoxyphenyl)but-1-en-1-yl)-2,3-dihydro-1H-inden-1-one;
6-((1E)-4-(4-benzylphenyl)but-1-en-1-yl)-2,3-dihydro-1H-inden-1-one;
6-((1E)-3-(4-benzylphenoxy)prop-1-en-1-yl)-2,3-dihydro-1H-inden-1-one;
and listed in Table 3:
6-(4-(4-ethylphenyl)butyl)-2,3-dihydro-1H-inden-1-one;
(E)-5-(4-(4-ethylphenyl)but-1-en-1-yl)benzofuran-3(2H)-one;
(E)-5-(4-(4-ethylphenyl)butyl)-2,3-dihydro-1-benzofuran-3-one;
(E)-6-(4-(4-chlorophenyl)-4-oxobut-1-en-1-yl)-2,3-dihydro-1H-inden-1-one;

In the second aspect, the present invention provides pharmaceutical compositions or cosmetic compositions. The compositions comprise compounds provided by the invention as described abovementioned and pharmaceutically or cosmetically acceptable excipients.

In another embodiment, the pharmaceutical compositions described herein are formulated into any suitable dosage form, including but not limited to, aqueous dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and immediate release formulations.

In the third aspect, the present invention provides a useful in preventing and treating peroxisome proliferator-activated receptor gamma (PPARγ) activity-dependent diseases, and the preparation of medicaments and/or dermal compositions prepared from the abovementioned compounds for the prevention and treatment of such diseases.

In the fourth aspect, the present invention provides the prevention and treatment of peroxisome proliferator-activated receptor gamma (PPARγ) activity-dependent diseases.

The abovementioned diseases are selected from neurological disorders and strokes, inflammation and immune diseases, metabolic diseases, kidney diseases, and cancers.

The abovementioned neurological disorders are selected from the group consisting of, but not limited to, dementia (mainly including Alzheimer's disease), vascular dementia, mixed dementia, Lewy body disease, frontotemporal dementia, secondary dementia, Huntington's disease, motor neuron disease, multisystem atrophy, progressive supranuclear palsy, normal pressure hydrocephalus, epilepsy, Parkinson's disease, stroke, spinal cord injury, traumatic brain injury. Pick's disease, Niemann-Pick's disease, amyloid angiopathy, amyloid cerebrovascular disease, systemic amyloidosis, Hereditary cerebral hemorrhage with amyloidosis (e.g., Dutch type), inclusion body myositis, mild cognitive impairment, Down syndrome, amyotrophic lateral sclerosis (ALS), multiple sclerosis, Duchenne muscular dystrophy, Becker's muscular dystrophy, Facioscapulohumeral muscular dystrophy (FSHD), Limb-girdle muscular dystrophies (LGMD), neuropathic pain (e.g., Painful diabetic peripheral neuropathy, postherpetic neuralgia, cancer-related pains such as chemotherapy-induced peripheral neuropathy), spinal cord injury induced neuropathic pain, complex regional pain syndrome (CRPS), AIDS (Acquired immunodeficiency syndrome)-related pain, multiple sclerosis-related pain, phantom limb pain, post-stroke pain, trigeminal neuralgia, migraine, alcohol or drug abuse related pain, etc; inflammatory pain or nociception pain being mixed with neuropathic pain sometimes e.g., lower back pain, and thus belonging to neurological disorder due to nerve damage occurring in these pains), age-related eye disease (e.g., macular degeneration, cataract, glaucoma, diabetic retinopathy). Preferred compounds are those listed in Tables 2 and 3, including the compounds named ELB00824, ELB00727, ELB00702, ELB001080, ELB001045, ELB00992, ELB00827, ELB00532, ELB00993, ELB00533, ELB001062, ELB00400, ELB001064, ELB00887, ELB00403. ELB00984, ELB00923, ELB00983, ELB00915, ELB00410, ELB001046, ELB001058, ELB001103, ELB001114, ELB001115, ELB001116, ELB001117, ELB001125, ELB001084, ELB001201, ELB001090, ELB001091, ELB001057, ELB00825, ELB001044, ELB001056, ELB001121, ELB001203, ELB03020. ELB03012, ELB03017, or ELB03019. More preferred are selected from the compounds named ELB00824, ELB00825, ELB001080, ELB001045, ELB001046, ELB001115, ELB001116, ELB001125, ELB00727, and preferred diseases are Alzheimer's disease and Parkinson's disease; or selected from the compounds named ELB00824, ELB00825, ELB001080, ELB001045, ELB001046, ELB001115, ELB001116, ELB001125, and preferred diseases are trigeminal neuralgia and Painful diabetic peripheral neuropathy.

The abovementioned cancers are selected from the group consisting of, but not limited to, lung cancer, colorectal (e.g., colon cancer), gastric cancer, liver cancer, prostate cancer, esophageal cancer, bladder cancer, kidney cancer, pancreatic cancer, lymphoma, brain cancer (e.g. pituitary cancer, glioblastoma, brain metastases), leukemia, breast cancer, thyroid cancer, cervical cancer, uterine cancer, ovarian cancer, melanoma, other types of cancers. Preferred compounds are those listed in Tables 2, and more preferred compounds are named ELB00824, ELB00727, ELB00702, ELB001080, ELB001045, ELB00992, ELB00827, ELB00532, ELB00993, ELB00533, ELB001062, ELB00400, ELB001064, ELB00887, ELB00403, ELB00984, ELB00923, ELB00983, ELB00915, ELB00410, ELB001046, ELB001058, ELB001103, ELB001114, ELB001115, ELB001116, ELB001117, ELB001125, ELB001084, ELB001201, ELB001090, ELB001091, ELB001057, ELB001203, ELB03020, ELB03012, ELB03017, or ELB03019.

The abovementioned kidney diseases are selected from the group consisting of, but not limited to, acute kidney injury, chronic kidney disease, chronic glomerulonephritis, membranous nephritis, proliferative nephritis, chronic renal failure, diabetic nephropathy, hypertensive nephropathy, purpuric nephritis, lupus nephritis, IgA nephropathy, glomerulosclerosis, nephrotic syndrome, renal ischemia and/or uremia. The abovementioned inflammatory and immune diseases are selected from the group consisting of, but not limited to, systemic lupus erythematosus (SLE), arthritis (e.g. rheumatoid arthritis spondylitis, psoriatic arthritis, osteoarthritis, ankylosing spondylarthritis), diabetes (type 1), multiple sclerosis, myasthenia gravis, vasculitis, inflammation of the skin (e.g., psoriasis, dermatitis and scleroderma), inflammatory intestinal diseases (e.g. inflammatory bowel disease (IBD), Crohn's disease and ulcerative colitis), asthma and atopic disorders (e.g., allergy), and transplant/graft rejection and graft versus host disease, and/or other selective dysfunction of the immune system. The abovementioned metabolic diseases are selected from the group consisting of, but not limited to, diabetes, dyslipidemia, arteriosclerosis, obesity, non-alcoholic tatty liver disease and/or other diseases. Preferred compounds are those listed in Table 2 and Table 3, and more preferred compounds are named ELB00824, ELB00727, ELB00702, ELB001080, ELB001045, ELB00992, ELB00827, ELB00532, ELB00993, ELB00533, ELB001062, ELB00400, ELB001064, ELB00887, ELB00403, ELB00984, ELB00923, ELB00983, ELB00915, ELB00410, ELB001046, ELB001058, ELB001103, ELB001114, ELB001115, ELB001116, ELB001117, ELB001125, ELB001084, ELB001201, ELB001090, ELB001091, ELB001057, ELB00825, ELB001044, ELB001056, ELB001121. ELB001203, ELB03020, ELB03012, ELB03017, or ELB03019. Particularly preferred compounds are named ELB00727 or ELB00824, and preferred disease is hyperglycemic nephropathy.

In the fifth aspect, the present invention provides a useful in preparation of medicaments or reagents prepared from the abovementioned compounds capable of inhibiting mitochondrial reactive oxygen species production.

The abovementioned medicaments are medicines for treating or preventing oxidative stress-related diseases. These oxidative stress-related diseases include, but are not limited to neurological disorders and strokes, metabolic diseases, kidney diseases, inflammation and immune diseases. Preferred compounds are those listed in Tables 2, and more preferred compounds are named ELB00824, ELB00825, ELB001115, ELB001116, ELB001125, ELB001044, ELB001080, ELB001045, ELB1046, or ELB001121.

In the sixth aspect, the present invention provides a useful in preparation of highly BBB permeable PPARγ agonists prepared from the abovementioned compounds.

The abovementioned PPARγ agonists can be used to prepare medicaments for treating PPARγ-related diseases, which including but not limited to neurological disorders and strokes, metabolic diseases, kidney diseases, inflammation and immune diseases, cancer, and other aging related diseases. Preferred compounds are those listed in Tables 2 and 3, and more preferred compounds are named ELB00824, ELB00400, ELB00887, ELB001080, ELB001045, ELB001062, ELB001064, ELB00984, ELB001044, ELB001046, ELB001058, ELB001103, ELB001115, ELB001116, ELB001117, ELB001084, ELB001201 or ELB001057.

In the seventh aspect, the present invention provides a useful in preparation of PPARγ agonists being able to active PPARγ in vitro and prepared from the abovementioned compounds. Preferred compounds are those listed in Tables 2, and more preferred compounds are named ELB00400, ELB00532, ELB00702, ELB00727, ELB00824, ELB00827, ELB00915, ELB00993, ELB001080, ELB001045, ELB001046, ELB001090, ELB001115, ELB001116, ELB001125 or ELB001201.

In the eighth aspect, the present invention provides a useful in preparation of PPARγ agonists being able to increase the transcription of klotho gene in vitro and prepared from the abovementioned compounds. These PPARγ agonists can be used to prepare medicaments for treating PPARγ- or Klotho-related diseases, which include but not limited to, neurological disorders and strokes, metabolic diseases, kidney diseases, inflammation and immune diseases, cancer, and other aging related diseases. Preferred compounds are those listed in Tables 2 and 3, and more preferred compounds are named ELB00400, ELB00532, ELB00702, ELB00727, ELB00824, ELB00827, ELB00915, ELB00993, ELB001080, ELB001045, ELB001046, ELB001090, ELB001115, ELB001116, ELB001125, or ELB001201.

In the ninth aspect, the present invention provides a useful in preparation of PPARγ agonists being able to increase the transcription of klotho gene in vivo and prepared from the abovementioned compounds. These PPARγ agonists can be used to prepare medicaments for treating PPARγ- or Klotho-related diseases, which include but not limited to, neurological disorders and strokes, metabolic diseases, kidney diseases, inflammation and immune diseases, cancer, and other aging related diseases. Preferred compounds are those listed in Tables 2 and 3, ELB00400, ELB00532, ELB00702, ELB00727, ELB00824, ELB00827, ELB00915, ELB00993, ELB001080, ELB001045, ELB001046, ELB001090, ELB001115, ELB001116, ELB001125 or ELB001201.

Accordingly, the present invention provides novel compounds as PPARγ agonists that can inhibit the production of mitochondrial reactive oxygen species and/or has high blood-brain barrier permeability, related preparation methods, and a useful as drug for prevention and treatment of related indications.

DESCRIPTION OF FIGURES

FIG. 6 shows the therapeutic effects of the carbonyl-containing cyclic compound provided by the present invention on kidney disease, inflammation and immune disease, and metabolic disease; wherein: FIG. 6A shows the effect of anti-nephropathy; FIG. 6B shows the effect of treating inflammation and immune disease; FIG. 6C Shows the effect of treating metabolic diseases.

MODE OF CARRYING OUT THE INVENTION

Figure 1:
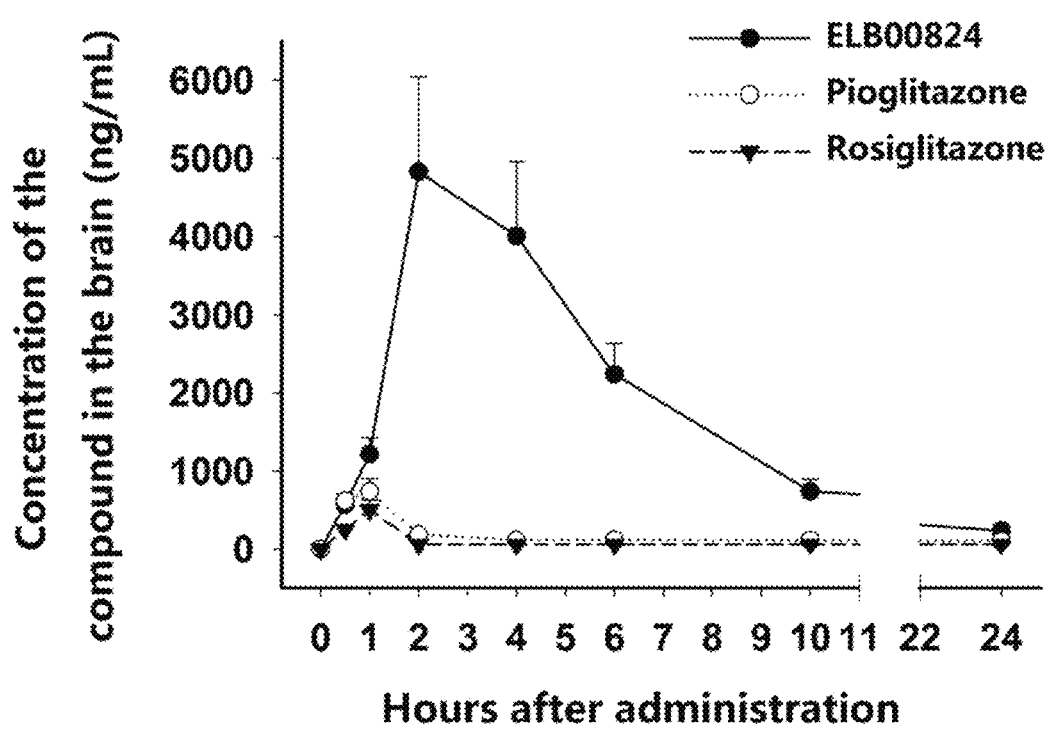
FIG. 1 is the concentration-time curve of ELB00824, rosiglitazone, and pioglitazone in the rat brain after a single injection (10 mg/kg).

The peroxisome proliferator-activated receptors (PPARs) are a group of nuclear receptor superfamily. When paired with specific agonists, they can enter the nucleus of the cells, bind to specific DNA regions on the chromosome, activate or inhibit the expression of multiple genes and regulate many functions of the cells. The superfamily comprises of the following three subtypes: PPARα, PPARγ, and PPARβ/δ. PPARα primary regulates lipid metabolism and modulates inflammation. Activation of PPARβ/δ participates in embryonic development, implantation and bone formation. PPARγ is a key factor in many physiological functions, so that its agonists can be used for threating various diseases, including but not limited to, neurological disorders and strokes, metabolic diseases, kidney diseases, inflammation and immune diseases, cancer, aging related diseases, etc. (1) In terms of neurological disorders and strokes, some animal experiments have found that PPARγ agonists are effective for the treatment of Alzheimer's disease, Parkinson's disease, brain injury and amyotrophic lateral sclerosis. Their therapeutic mechanisms include regulating inflammation (e.g., inhibiting proinflammatory molecules produced by glial cells and peripheral immune cells), inhibiting the accumulation of amyloid plaques in the cerebral cortex and hippocampus, reducing the production of mitochondrial reactive oxygen species (ROS) and ROS induced oxidative stress, regulating enzyme activities of mitochondrial electron transfer chain, increase the expression level of klotho protein and its downstream anti-oxidative stress proteins (such as manganese superoxide dismulase (MnSOD)), increasing the expression of some synaptic proteins, inducing the expression of neuroprolective brain-derived neurotrophic factor (BDNF), inhibiting apoptosis, etc. (2) Metabolic diseases are the diseases where PPARγ play the most striking role, and US FDA has approved 3 anti-diabetic Active Pharmaceutical Ingredients targeting PPARγ. PPARγ regulates adipocyte differentiation, and multiple metabolism processes (including glucose, lipid, energy, etc.). PPARγ can also increase insulin sensitivity in peripheral tissues, reduce insulin resistance, thereby regulate glucose metabolism and lower blood sugar. PPARγ can also maintain the functions, proliferation and differentiation of vascular endothelial cells, and has anti-inflammatory effects. PPARγ activation reduces the expression of adipokines that induce insulin resistance, including TNF-α. IL-1 and resistin. In macrophages, PPARγ inhibits the up-regulation of inducible nitric oxide synthase (iNOS). PPARγ agonists can also induce the kidney to produce secreted Klotho protein into the blood to protect cardiovascular functions. In addition to the direct protective effects, these mechanisms also indirectly treat cardiovascular disease by controlling risk factors of cardiovascular disease such as atherosclerosis, diabetes, hypertension, obesity and dyslipidemia. (4) In terms of inflammation and immune diseases, the main feature of the inflammatory condition is the activation of macrophages and monocytes at the site of injury, subsequently increase of the release of pro-inflammatory mediators (such as TNF-α, IL-6, IL-1β), which in turn stimulate the production of some cyclooxygenase products. PPARγ activation can inhibit the expression of multiple inflammatory cytokines, and promote the differentiation of immune cells into an anti-inflammatory phenotype. (5) In terms of kidney diseases, and other aging related diseases, in addition to the above-mentioned multiple protective mechanisms, the Klotho protein induced by PPARγ has important protective effects on the kidneys, and promote collagen expression and wound healing. (6) In terms of cancer, animal and human experiments show that PPARγ inhibits the proliferation of malignant cells by inducing the expression of some anti-oncogenes, such as phosphatase and tensin homolog (PTEN) and Klotho protein, thus PPARγ activation can be used to treat a variety of cancers (including malignant liposarcoma, breast cancer, prostate cancer, colorectal cancer, non-small cell lung cancer, pancreatic cancer, bladder cancer, gastric cancer and glioma). Anti-cancer mechanism of PTEN involves regulating protein kinase B (also known as Akt) signaling pathway. Klotho's anti-cancer mechanism involves the insulin-like growth factor 1 (IGF-1) signaling pathway and the Wnt signaling pathway. The above contents are detailed in reference 2: Tyagi S, et al. The peroxisome proliferator-activated receptor: A family of nuclear receptors role in various diseases [J]. J Adv Pharm Technol Res 2011, 2(4): 236-240.

The specific region where PPAR and DNA bind is called the peroxisome proliferator-activated receptor response element (PPRE). The klotho gene promoter region contains PPRE, so after activation by a ligand agonist, PPARγ can activate the klotho gene by binding to this promoter. The Klotho protein expressed by this gene is a transmembrane or secreted protein containing β-glucuronidase activity. By activating the klotho gene, PPARγ agonists have the potential to treat and/or prevent Klotho protein-related diseases.

Some cell and animal studies have shown that traditional PPARγ agonists may treat diseases such as diabetes and pains not only by activating PPARγ, but also by other mechanisms independent to PPARγ. These non-PPARγ targets include, but are not limited to two newly discovered mitochondrial proteins: mitochondrial pyruvate carrier (MPC) or an iron-sulfur cluster transfer protein called mitoNEET. PPARγ agonists can regulate mitochondrial function by binding to these mitochondrial target proteins, including reducing the respiratory activity and reducing the production of reactive oxygen species (ROS) of mitochondria (reference 3: Wright M B, et al. Minireview: Challenges and opportunities in development of PPAR agonists [J], Mol Endocrinol 2014, 71(11):1756-1768).

The abovementioned diseases related to PPARγ, mitochondrial function, or Klotho protein include, but are not limited to neurological disorders and strokes, metabolic diseases, kidney diseases, inflammation and immune diseases, and cancer.

Compound

In the first aspect, the present invention provides compounds of formula (I) or pharmaceutically acceptable salts, solvates, prodrugs or metabolites thereof:

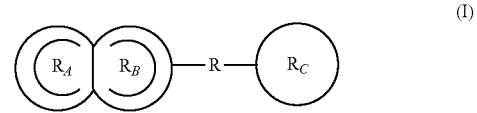

(I)

Among them, cyclic $R_A$ contains carbonyl or amide groups, which are saturated or unsaturated $C_{5-12}$ carbocyclic ring or $C_{5-12}$ heterocyclic ring that are optionally substituted by any one or more $R^a$;

cyclic $R_B$ is $C_{3-8}$ cycloalkyl, $C_{3-8}$ saturated cycloalkyl, $C_{3-8}$ unsaturated cycloalkyl, $C_{6-12}$ fused heterocyclic, $C_{6-12}$ aryl, $C_{6-12}$ heteroaryl optionally substituted by one or more $R^b$; or there is no cyclic $R_B$;

cyclic $R_C$ is $C_{3-8}$ cycloalkyl, $C_{3-8}$ saturated heterocycloalkyl, $C_{3-8}$ unsaturated heterocycloalkyl, $C_{6-10}$ aryl and $C_{6-10}$ heteroaryl optionally substituted by one or more $R^C$;

R is $C_{1-12}$ alkyl, $C_{2-8}$ alkenyl, $C_{2-8}$ alkynyl, $C_{3-6}$ cycloalkyl and $C_{3-6}$, heterocycloalkyl which are optionally substituted by one or more $R^1$ or connected by one or more $R^1$;

among them, $R^1$, $R^a$, $R^b$ or $R^c$ can be independently selected from hydrogen atoms, halogen, hydroxyl, nitro, cyano, isocyanide, sulfonyl, $C_{1-6}$ alkyl, $C_{1-6}$ cycloalkyl, $C_{1-6}$ heterocyclyl, $C_{2-8}$ alkenyl, $C_{2-8}$ alkynyl, $C_{1-6}$ alkoxy, halogenated $C_1$-$C_6$ alkyl, halogenated $C_1$-$C_6$ alkoxy, halogenated $C_1$-$C_6$ cycloalkyl, $C_{1-6}$ alkylthio, $C_{1-6}$ alkylcarbonyl, $C_{1-6}$ alkoxycarbonyl, bis($C_{1-6}$ alkyl) amino, $C_{2-6}$ alkoxycarbonyl, $C_{2-6}$ alkylthiocarbonyl, amino, $C_{1-6}$ alkylamino, bis($C_{1-6}$ alkyl) amino, carbamoyl, $C_{1-6}$ alkylcarbamoyl, bis($C_{1-6}$ alkyl) carbamoyl, bis($C_{1-6}$ alkyl) $C_{2-6}$ alkylcarbamoyl, sulfamoyl, $C_{1-6}$ alkylsulfamoyl, bis($C_{1-6}$ alkyl) sulfamoyl, bis ($C_{1-6}$ alkyl) amino, $C_{2-6}$ alkylsulfamoyl, $C_{1-6}$ alkylsulfonyl, $C_{1-6}$ alkylsulfinyl, $C_{1-6}$ alkyl sulfonyl sulfonyl, bis($C_{1-6}$ alkyl) phosphono, hydroxyl $C_{1-6}$ alkyl, hydroxycarbonyl $C_{1-6}$ alkyl, $C_{1-6}$ alkoxyl $C_{1-6}$ alkyl, $C_{1-6}$ alkylsulfonyl $C_{1-6}$ alkyl, $C_{1-6}$ alkylsulfinyl $C_{1-6}$ alkyl, $C_{1-6}$ alkylthiocarbonyl $C_{1-6}$ alkyl, bis($C_{1-6}$ alkyl) phosphono $C_{1-6}$ alkyl, hydroxyl $C_{2-6}$ alkoxy, $C_{1-6}$ alkoxy $C_{2-6}$ alkoxy, amino $C_{1-6}$ alkyl, $C_{1-6}$ alkylamino $C_{1-6}$ alkyl, bis($C_{1-6}$ alkyl) amino $C_{1-6}$ alkyl, bis($C_{1-6}$ alkyl) aminoacetyl, amino $C_{2-6}$ alkoxy, $C_{1-6}$ alkylamino $C_{2-6}$ alkoxy, bis($C_{1-6}$ alkyl) amino $C_{2-6}$ alkoxy, hydroxy $C_{2-6}$ alkylamino, $C_{2-6}$ alkoxy $C_{2-6}$ alkylamino, amino $C_{2-6}$ alkylamino, $C_{1-6}$ alkylamino $C_{2-6}$ alkylamino, bis($C_{1-6}$ alkyl) amino $C_{2-6}$ alkylamino, $C_{5-10}$ aryl, $C_{5-10}$ heteroaryl group;

cyclic $R_C$ is preferred to be $C_{6-10}$ aryl and $C_{6-10}$ heteroaryl optionally substituted by one or more $R^C$, in which $R^C$ is $C_{1-6}$ alkyl.

In a preferred embodiment, R is $C_{1-12}$ alkyl and $C_{2-8}$ alkenyl groups optionally substituted by one or more $R^1$s or connected by one or more $R^1$s, where $R^1$ is one group selected from hydrogen atoms, halogens, hydroxyl, nitro, cyano, sulfonate, $C_{5-10}$ aryl and $C_{5-10}$ heteroaryl groups

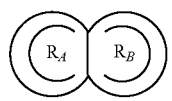

is selected from:

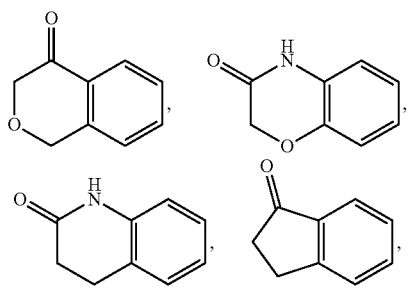

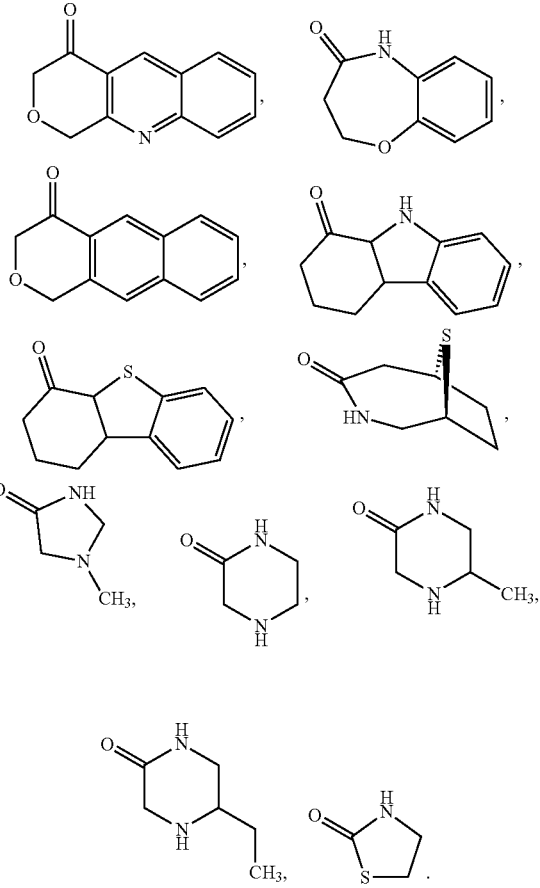

In one embodiment of the present invention, the total number of oxygen atoms and nitrogen atoms in the compounds provided by the present invention is less than 4, preferably less than 3, more preferred less than 2.

In one embodiment of the present invention, the total number of sulfur atoms in the compounds provided by the present invention is 0 to 2, with 0 to 1 being more preferred.

In one embodiment of the present invention, the molecular weight of the compounds provided by the present invention is less than 400 Dalton.

The scope of the invention includes any combination of the elements from the different species, embodiments, functions and/or subassemblies disclosed herein, as would be within the skill of the art.

According to Table 1 below, the present invention provides 2 groups of compounds with strong ability to inhibit the production of reactive oxygen species, which can be used for different types of indications. They are (1) high BBB/strong PPAR group with both higher blood-brain barrier permeability and stronger PPARγ agonist activity; (2) high BBB/weak PPAR group with both higher blood-brain barrier permeability and weaker PPARγ agonist activity. The blood-brain barrier permeability and PPARγ agonist activity are relative to those of the clinically used old PPARγ agonists (i.e., rosiglitazone and pioglitazone). Among the two old drugs, pioglitazone has a slightly stronger ability to inhibit the production of reactive oxygen species, and rosiglitazone has a slightly stronger PPARγ agonist activity.

TABLE 1

Classification of new compounds provided by the invention and corresponding therapeutic indications.

| | | Classification of new compounds | |
|---|---|---|---|
| | | High BBB/strong PPAR group (Table 2) | High BBB/weak PPAR group (Table 3) |
| Abilities of the compound | BBB permeability | Higher than pioglitazone | |
| | PPARγ agonist activity | Stronger than Rosiglitazone | Weaker than Rosiglitazone |
| Therapeutic indications | | Greater therapeutic potential | |
| Classification | Common indication | | |
| 1 Neurological disorders and strokes | Alzheimer's disease | | |
| 2 metabolic diseases | Diabetes, fatty liver | | |
| 3 Kidney diseases | Diabetic nephropathy | | |
| 4 Inflammation and immune diseases | Psoriasis | | |
| 5 Cancer | | Greater therapeutic potential | Less therapeutic potential |

Specifically, the compounds of formula (I) include, but is not limited to, these listed in Tables 2 and 3 below. Note IUPAC is the abbreviation for International Union of Pure and Applied Chemistry.

TABLE 2

High BBB/strong PPAR group of new compounds

| Compound Structure | Name in this patent | IUPAC Name |
|---|---|---|
| 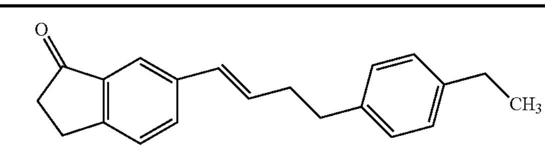 | Compound 2 (ELB00824) | (E)-6-(4-(4-ethylphenyl)but-1-en-1-yl)-2,3-dihydro-1H-inden-1-one |
| 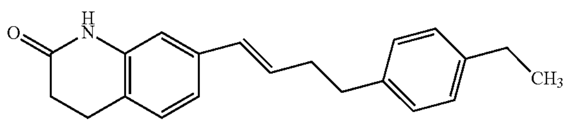 [SMILES: CCc1ccc(CC/C=C/c2ccc3c(c2)NC(=O)CC3)cc1] | Compound 5 (ELB00727) | (E)-7-(4-(4-ethylphenyl)but-1-en-1-yl)-3,4-dihydroquinolin-2(1H)-one |
| 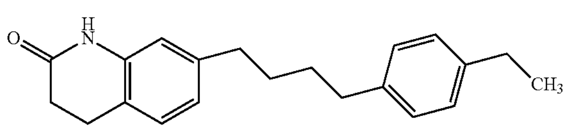 [SMILES: CCc1ccc(CCCCc2ccc3c(c2)NC(=O)CC3)cc1] | Compound 6 (ELB00702) | 7-(4-(4-ethylphenyl)butyl)-3,4-dihydroquinolin-2(1H)-one |
| 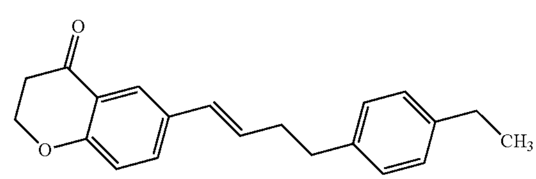 [SMILES: CCc1ccc(CC/C=C/c2ccc3c(c2)C(=O)CCO3)cc1] | ELB001080 | (E)-6-(4-(4-ethylphenyl)but-1-en-1-yl)chroman-4-one |
| 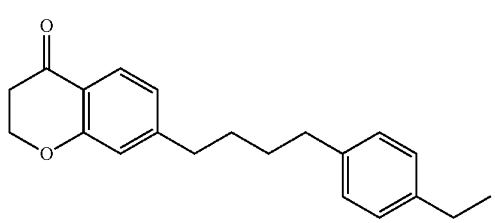 [SMILES: CCc1ccc(CCCCc2ccc3c(c2)OCCC3=O)cc1] | Compound 45 (ELB001057) | 7-(4-(4-ethylphenyl)butyl)chroman-4-one |

TABLE 2-continued

High BBB/strong PPAR group of new compounds

| Compound Structure | Name in this patent | IUPAC Name |
|---|---|---|
| 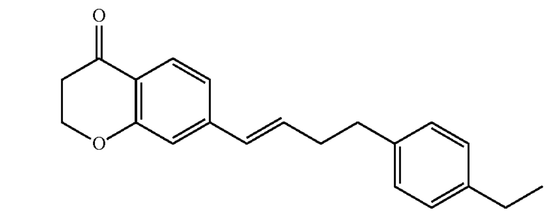 [SMILES: CCc1ccc(CC/C=C/c2ccc3c(c2)OCCC3=O)cc1] | Compound 9 (ELB001045) | (E)-7-(4-(4-ethylphenyl)but-1-en-1-yl)chroman-4-one |
| 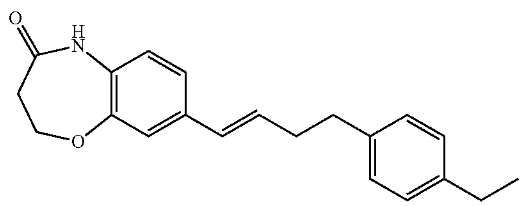 [SMILES: CCc1ccc(CC/C=C/c2ccc3c(c2)OCCC(=O)N3)cc1] | Compound 11 (ELB00992) | (E)-8-(4-(4-ethylphenyl)but-1-en-1-yl)-2,3-dihydrobenzo[b][1,4]oxazepin-4(5H)-one |
| 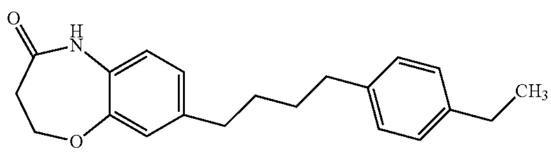 [SMILES: CCc1ccc(CCCCc2ccc3c(c2)OCCC(=O)N3)cc1] | Compound 12 (ELB00827) | 8-(4-(4-ethylphenyl)butyl)-2,3-dihydrobenzo[b][1,4]oxazepin-4(5H)-one |
| 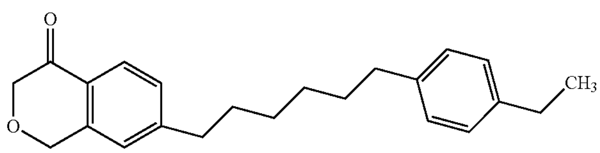 [SMILES: CCc1ccc(CCCCCCc2ccc3c(c2)COCC3=O)cc1] | Compound 18 (ELB00532) | 6-(6-(4-ethylphenyl)hexyl)isochroman-4-one |
| 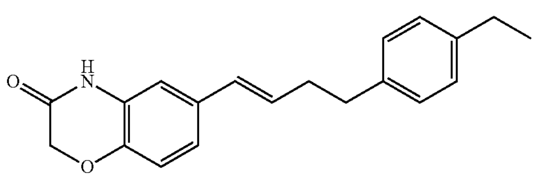 [SMILES: CCc1ccc(CC/C=C/c2ccc3c(c2)NC(=O)CO3)cc1] | Compound 20 (ELB00993) | (E)-6-(4-(4-ethylphenyl)but-1-en-1-yl)-2H-benzo[b][1,4]oxazin-3(4H)-one |
| 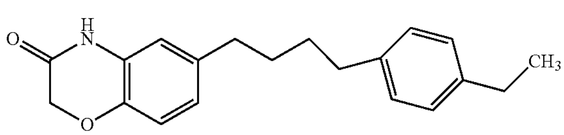 [SMILES: CCc1ccc(CCCCc2ccc3c(c2)NC(=O)CO3)cc1] | Compound 21 (ELB00533) | 6-(4-(4-ethylphenyl)butyl)-2H-benzo[b][1,4]oxazin-3(4H)-one |
| 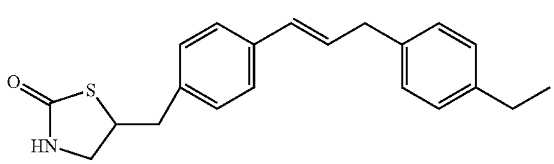 [SMILES: CCc1ccc(C/C=C/c2ccc(CC3CNC(=O)S3)cc2)cc1] | (ELB001062) | (E)-7-(4-(4-ethylphenyl)but-1-en-1-yl)-2,3,4,4a,9,9a-hexahydro-1H-carbazol-1-one |
| 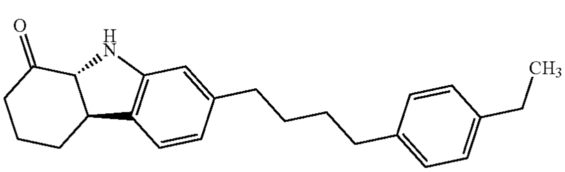 [SMILES: CCc1ccc(CCCCc2ccc3c(c2)N[C@H]2C(=O)CCC[C@H]32)cc1] | (ELB00400) | (4aR,9aR)-7-(4-(4-ethylphenyl)butyl)-2,3,4,4a,9,9a-hexahydro-1H-carbazol-1-one |
| 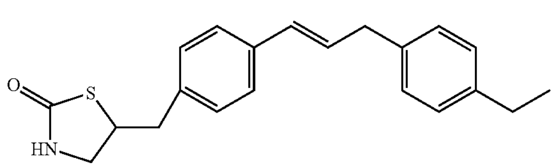 [SMILES: CCc1ccc(C/C=C/c2ccc(CC3CNC(=O)S3)cc2)cc1] | (ELB001064) | (E)-7-(4-(4-ethylphenyl)but-1-en-1-yl)-1,2,3,9b-tetrahydrodibenzo[b,d]thiophen-4(4aH)-one |

TABLE 2-continued

High BBB/strong PPAR group of new compounds

| Compound Structure | Name in this patent | IUPAC Name |
|---|---|---|
| 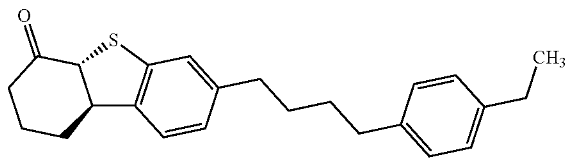 [SMILES: CCc1ccc(CCCCc2ccc3c(c2)S[C@H]2C(=O)CCC[C@H]32)cc1] | (ELB00887) | (4aR,9bR)-7-(4-(4-ethylphenyl)butyl)-1,2,3,9b-tetrahydrodibenzo[b,d]thiophen-4(4aH)-one |
| 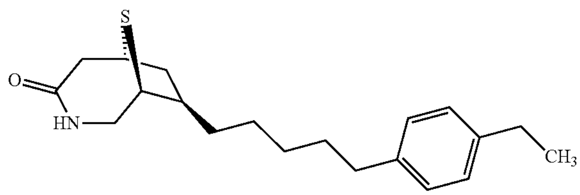 [SMILES: CCc1ccc(CCCCC[C@@H]2C[C@@H]3CC(=O)NC[C@H]2S3)cc1] | (ELB00403) | (1S,6R,8R)-8-(5-(4-ethylphenyl)pentyl)-9-thia-3-azabicyclo[4.2.1]nonan-4-one |
| 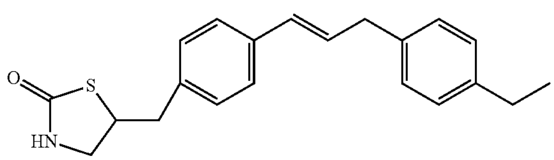 [SMILES: CCc1ccc(C/C=C/c2ccc(CC3CNC(=O)S3)cc2)cc1] | Compound 25 (ELB00984) | (E)-2-(3-(3-(4-ethylphenyl)prop-1-en-1-yl)benzyl)-1-methylimidazolidin-4-one |
| 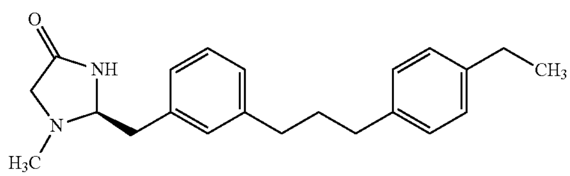 [SMILES: CCc1ccc(CCCc2cccc(C[C@@H]3NC(=O)CN3C)c2)cc1] | Compound 26 (ELB00923) | (2R)-2-((3-(3-(4-ethylphenyl)propyl)phenyl)methyl)-1-methylimidazolidin-4-one |
| 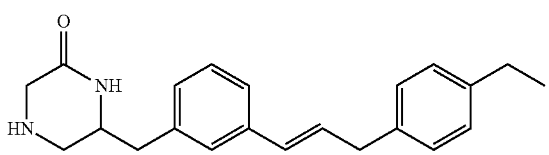 [SMILES: CCc1ccc(C/C=C/c2cccc(CC3CNCC(=O)N3)c2)cc1] | (ELB00983) | (E)-6-(3-(3-(4-ethylphenyl)prop-1-en-1-yl)benzyl)piperazin-2-one |
| 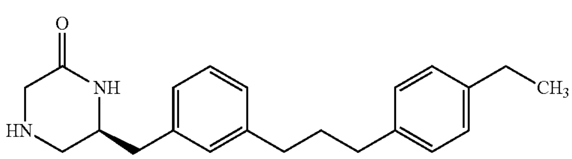 [SMILES: CCc1ccc(CCCc2cccc(C[C@H]3CNCC(=O)N3)c2)cc1] | (ELB00915) | (6S)-6-((3-(3-(4-ethylphenyl)propyl)phenyl)methyl)piperazin-2-one |
| 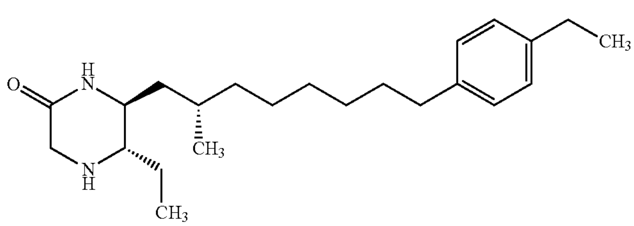 [SMILES: CCc1ccc(CCCCCC[C@H](C)C[C@@H]2NC(=O)CN[C@H]2CC)cc1] | (ELB00410) | (5S,6S)-5-ethyl-6-((2S)-8-(4-ethylphenyl)-2-methyloctyl)piperazin-2-one |
| 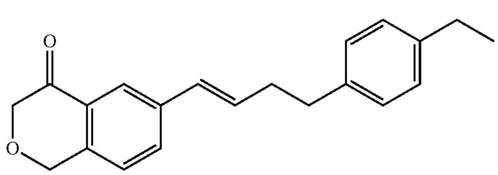 [SMILES: CCc1ccc(CC/C=C/c2ccc3c(c2)C(=O)COC3)cc1] | Compound 29 (ELB001046) | (E)-6-(4-(4-ethylphenyl)but-1-en-1-yl)isochroman-4-one |

TABLE 2-continued

High BBB/strong PPAR group of new compounds

| Compound Structure | Name in this patent | IUPAC Name |
|---|---|---|
| 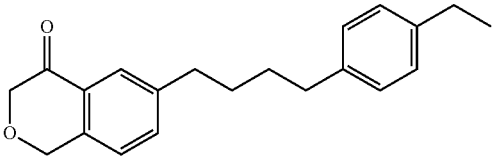 [SMILES: CCc1ccc(CCCCc2ccc3c(c2)C(=O)COC3)cc1] | Compound 30 (ELB001058) | 6-(4-(4-ethylphenyl)butyl) isochroman-4-one |
| 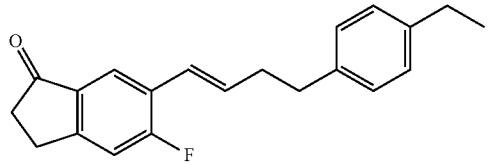 [SMILES: CCc1ccc(CC/C=C/c2cc3c(cc2F)CCC3=O)cc1] | (ELB001103) | (E)-6-(4-(4-ethylphenyl)but-1-en-1-yl)-5-fluoro-2,3-dihydro-1H-inden-1-one |
| 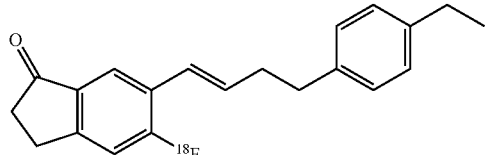 | (ELB001114) | (E)-6-(4-(4-ethylphenyl)but-1-en-1-yl)-5-($^{18}$F)fluoro-2,3-dihydro-1H-inden-1-one |
| 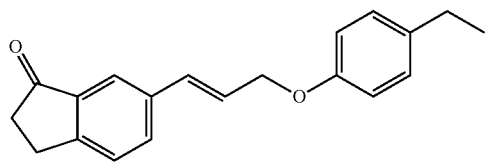 [SMILES: CCc1ccc(OC/C=C/c2ccc3c(c2)C(=O)CC3)cc1] | Compound 34 (ELB001115) | (E)-6-(3-(4-ethylphenoxy)prop-1-en-1-yl)-2,3-dihydro-1H-inden-1-one |
| 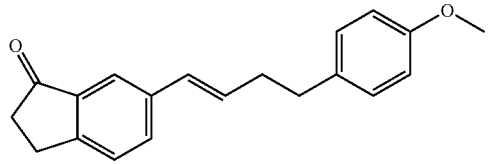 [SMILES: COc1ccc(OC/C=C/c2ccc3c(c2)C(=O)CC3)cc1] | Compound 36 (ELB001116) | (E)-6-(4-(4-methoxyphenyl)but-1-en-1-yl)-2,3-dihydro-1H-inden-1-one |
| 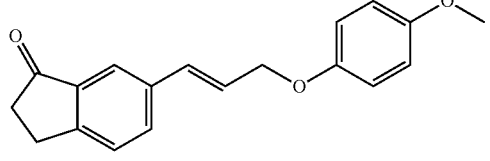 | (ELB001117) | (E)-6-(3-(4-methoxyphenoxy)prop-1-en-1-yl)-2,3-dihydro-1H-inden-1-one |
| 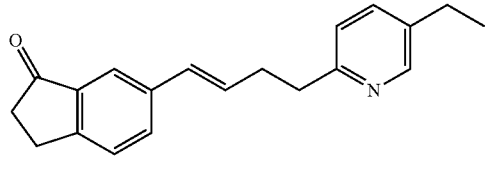 [SMILES: CCc1ccc(CC/C=C/c2ccc3c(c2)C(=O)CC3)nc1] | Compound 38 (ELB001125) | (E)-6-(4-(5-ethylpyridin-2-yl)but-1-en-1-yl)-2,3-dihydro-1H-inden-1-one |
| 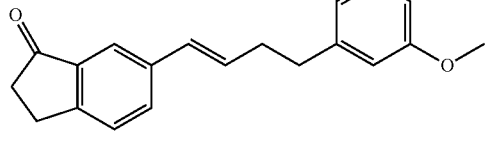 | Compound 40 (ELB001084) | (E)-6-(4-(3-methoxyphenyl)but-1-en-1-yl)-2,3-dihydro-1H-inden-1-one |
| 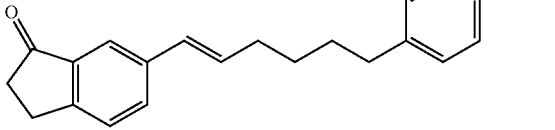 | Compound 42 (ELB001201) | (E)-6-(6-(4-ethylphenyl)hex-1-en-1-yl)-2,3-dihydro-1H-inden-1-one |

TABLE 2-continued

High BBB/strong PPAR group of new compounds

| Compound Structure | Name in this patent | IUPAC Name |
|---|---|---|
| 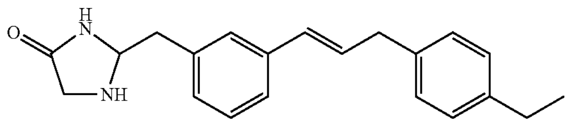 [SMILES: CCc1ccc(C/C=C/c2cccc(CC3NCC(=O)N3)c2)cc1] | Compound 43 (ELB001090) | (E)-2-(3-(3-(4-ethylphenyl)prop-1-en-1-yl)benzyl)imidazolidin-4-one |
| 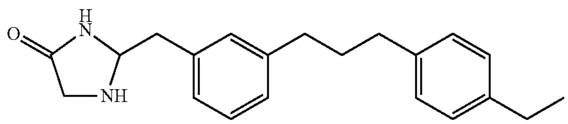 [SMILES: CCc1ccc(CCCc2cccc(CC3NCC(=O)N3)c2)cc1] | Compound 44 (E1B001091) | 2-(3-(3-(4-ethylphenyl)propyl)benzyl)imidazolidin-4-one |
| 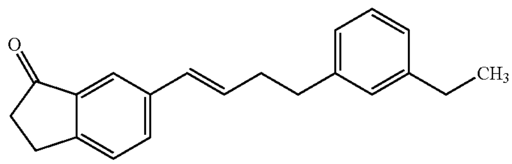 [SMILES: CCc1cccc(CC/C=C/c2ccc3c(c2)C(=O)CC3)c1] | Compound 48 (ELB001203) | 6-((1E)-4-(3-ethylphenyl)but-1-en-1-yl)-2,3-dihydro-1H-inden-1-one |
| 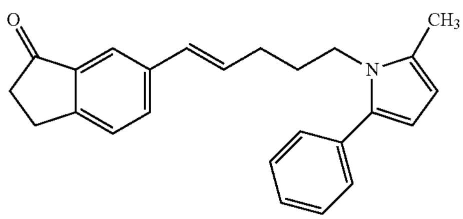 [SMILES: Cc1ccc(-c2ccccc2)n1CCC/C=C/c1ccc2c(c1)C(=O)CC2] | (ELB03020) | 6-((1E)-5-(2-methyl-5-phenyl-1H-pyrrol-1-yl)pent-1-en-1-yl)-2,3-dihydro-1H-inden-1-one |
| 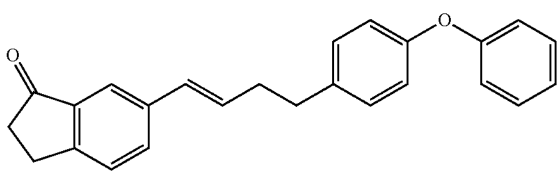 [SMILES: O=C1CCc2ccc(/C=C/CCc3ccc(Oc4ccccc4)cc3)cc21] | (ELB03012) | 6-((1E)-4-(4-phenoxyphenyl)but-1-en-1-yl)-2,3-dihydro-1H-inden-1-one |
| 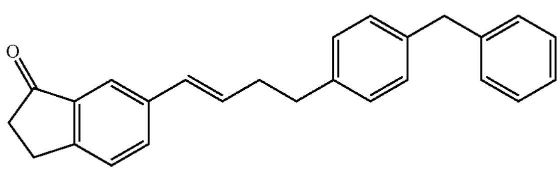 [SMILES: O=C1CCc2ccc(/C=C/CCc3ccc(Cc4ccccc4)cc3)cc21] | (ELB03017) | 6-((1E)-4-(4-benzylphenyl)but-1-en-1-yl)-2,3-dihydro-1H-inden-1-one |
| 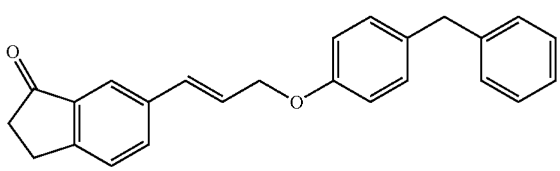 [SMILES: O=C1CCc2ccc(/C=C/COc3ccc(Cc4ccccc4)cc3)cc21] | (ELB03019) | 6-((1E)-3-(4-benzylphenoxy)prop-1-en-1-yl)-2,3-dihydro-1H-inden-1-one |

TABLE 3

High BBB/weak PPAR group of new compounds

| Compound Structure | Name in this patent | IUPAC Name |
|---|---|---|
| 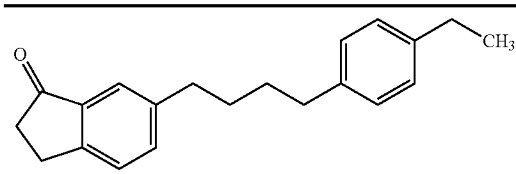 | Compound 3 (ELB00825) | 6-(4-(4-ethylphenyl)butyl)-2,3-dihydro-1H-inden-1-one |

TABLE 3-continued

High BBB/weak PPAR group of new compounds

| Compound Structure | Name in this patent | IUPAC Name |
|---|---|---|
| 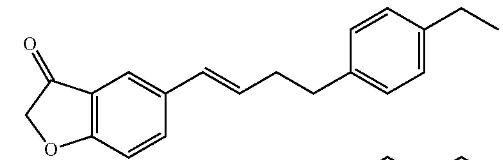 [SMILES: CCc1ccc(CC/C=C/c2ccc3c(c2)C(=O)CO3)cc1] | Compound 27 (ELB001044) | (E)-5-(4-(4-ethylphenyl)but-1-en-1-yl)benzofuran-3(2H)-one |
| 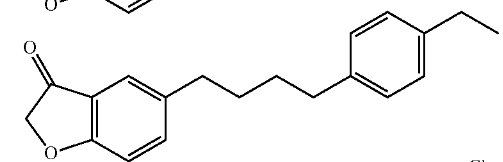 | Compound 28 (ELB004056) | (E)-5-(4-(4-ethylphenyl)butyl)-2,3-dihydro-1-benzofuran-3-one |
| 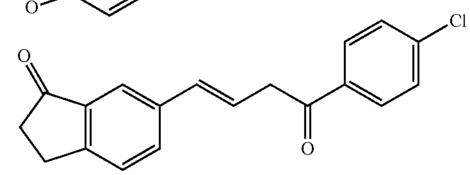 | (ELB001121) | (E)-6-(4-(4-chlorophenyl)-4-oxobut-1-en-1-yl)-2,3-dihydro-1H-inden-1-one |

Synthesis of Compound

The present invention further provides methods for synthesizing new PPARγ agonists, which are illustrated by the preparation of several compounds in the invention. In the following embodiments, the structures of compounds are confirmed by one or more of the followings: proton nuclear magnetic resonance, mass spectrometry, thin layer chromatography, and high performance liquid chromatography.

The following general reaction scheme can be used to prepare compounds (i.e., carbonyl-containing cyclic compound) of the present invention. Among them:

R is alkyl. A is a five-membered ring, a six-membered ring or a seven-membered ring. B is benzene, naphthalene, benzopyridine and other mono-cyclic or polycyclic. A and B can form bridged rings. According to literature 4 (Czaplik W M, et al. Domino iron catalysis: direct aryl-alkyl cross-coupling [J]. Angew Chem Int Ed Engl. 2009; 48(3) 607-10), compound D can be synthesized by cross-coupling reaction of halogenated aromatic Compound C with halogenated alkanes catalyzed by ferric chloride. Compound F was synthesized by Negishi coupling reaction of compound D and aryl halogenated compound E catalyzed by palladium acetate with tris(o-methylphenyl)phosphine as the ligand. Compound F reacted with hydroxylamine hydrochloride and converted to oxime compound G. Compound G and polyphosphoric acid underwent Beckmann rearrangement reaction to form Compound H. Compound I was obtained by hydrogen reduction catalyzed by palladium on carbon. Compound J was synthesized by hydrogen reduction of Compound F directly catalyzed by palladium on carbon.

Those skilled in the art can easily select and optimize similar reaction paths to prepare new compounds that conform to the general formulas of the present invention.

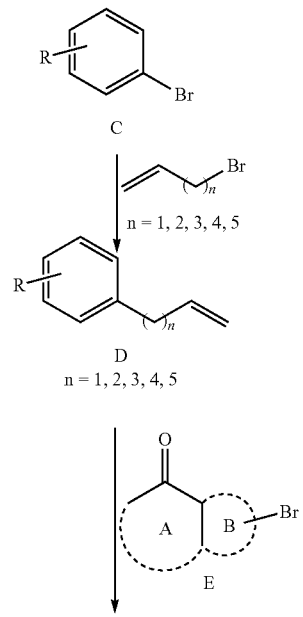

-continued

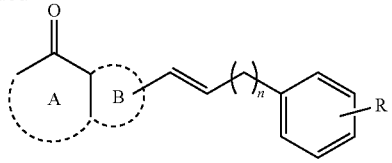

F
n = 1, 2, 3, 4, 5, e.g.,

ELB00824, ELB001044, ELB001045,
ELB001046, ELB001060, ELB001061,
ELB001062, ELB001064, ELB001084,
ELB001103, ELB001114, ELB001115,
ELB001116, ELB001117, ELB001119,
ELB001120, ELB001121, ELB001125,
ELB001130, ELB001131, ELB001201

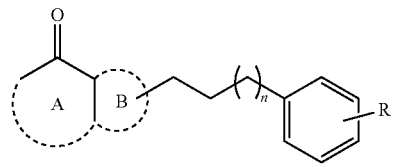

J
n = 1, 2, 3, 4, 5, e.g.,

ELB00400, ELB00402,
ELB00410, ELB00532,
ELB00825, ELB00826,
ELB00836, ELB00855,
ELB00887, ELB00904,
ELB00915, ELB00923,
ELB001057, ELB001058

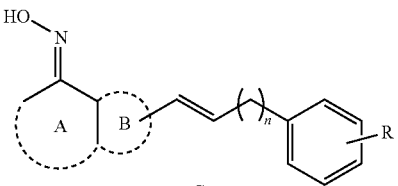

G
n = 1, 2, 3, 4, 5

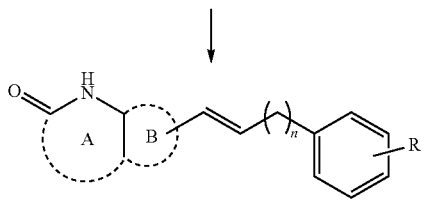

H
n = 1, 2, 3, 4, 5, e.g.,

ELB00727, ELB00979,
ELB00983, ELB00984,
ELB00992, ELB00993,
ELB001090

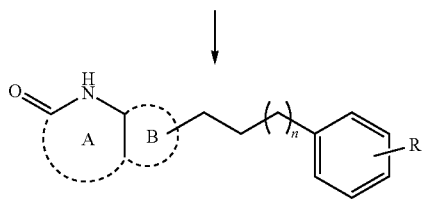

I
n = 1, 2, 3, 4, 5, e.g.,

ELB00403, ELB00533,
ELB00702, ELB00827,
ELB001091

Further Embodiments of Compounds

In one embodiment, those carbonyl-containing cyclic compound of Formula (I) provided in the present patent can be used in the form of pharmaceutically acceptable salts, prodrugs or metabolites derived from pharmaceutically, cosmetically or physiologically acceptable acids or bases. These salts include but are not limited to, the following mineral or inorganic acids such as hydrochloric acid, sulfuric acid, nitric acid, phosphoric acid; and organic acids such as acetic acid, oxalic acid, succinic acid, and maleic acid salts. Other salts include esters, carbamates and other conventional "prodrug" forms of alkali metals and alkaline earth metals such as sodium, potassium, calcium and magnesium salts. After administered in these forms, they are converted in vivo to the active moiety.

"Pharmaceutically acceptable" here refers to a substance, such as a carrier or diluent, that does not make the biological activity or properties of a compound disappear and is relatively non-toxic. For example, giving a substance to an individual does not cause unwanted biological effects or interact in harmful ways with any of its components.

The term "pharmaceutically acceptable salt" refers to the form in which a compound exists, which does not cause significant stimuli to the organism being administered with this compound, and does not diminish the biological activity and properties of the compound. In some specific respects, pharmaceutically acceptable salts are obtained by the reaction of compounds of formula (I) with acids, such as hydrochloric acid, hydrobromic acid, sulfuric acid, nitric acid, phosphoric acid, methanesulfonic acid, ethylsulfonic acid, p-toluene sulfonic acid, salicylic acid, etc. The reaction of compounds of formula (I) with alkali can also form pharmaceutically acceptable salts, such as ammonium salts; alkali metal salts (such as sodium or potassium salts); alkaline earth metal salts (such as calcium or magnesium salts); organic alkali salts (such as dicyclohexylamine, N-methyl-D-glucamine, tri(hydroxymethyl)methylamine); and amino acid salts, (such as arginine and lysine salts).

It should be understood that pharmaceutically acceptable salts include solvent addition or crystallization forms, especially solvates or polycrystalline. Solvents contain stoichiometric or non-stoichiometric solvents and are selectively formed during crystallization with pharmaceutically acceptable solvents such as water, ethanol, etc. A hydrate is formed when the solvent is water, or an alcoholate is formed when the solvent is ethanol. Solvents of compounds conforming to formula (I) can be easily prepared or formed according to the methods described in present invention In another embodiment, compounds conforming to formula (I) are prepared in different forms, including, but not limited to, amorphous, pulverized and macro-, micro- or nano-granular forms. In addition, compounds conforming to formula (I) can be prepared in monocrystalline and polycrystalline. Polycrystallines consist of different lattice arrangements of the same elements in compounds. Polycrystallines usually have different X-ray diffraction patterns, infrared spectroscopy, melting point, density, hardness, crystalline form, optical and electrical properties, stability and solubility. Different factors, such as recrystallization solvent, crystallization rate and storage temperature, may lead to a monocrystalline form being dominant.

In another embodiment, compounds of formula (I) can contain one or more asymmetric carbon atoms and some of the compounds can contain one or more asymmetric (chiral) centers and can thus give rise to optical isomers and diastereomers. While shown without respect to stereochemistry, when the compounds can contain one or more chiral centers, preferably at least one of the chiral centers is of S-stereochemistry. Thus, the invention includes such optical isomers and diastereomers; as well as the racemic and resolved, enantiomerically pure stereoisomers; as well as other mixtures of the R and S stereoisomers, and pharmaceutically acceptable salts, hydrates, metabolites, and prodrugs thereof.

In another embodiment, compounds conforming to formula (I) are prepared as prodrugs. "Prodrug" refers to a reagent being able to be converted into the prototype drug in vivo. Prodrugs are usually useful because in some cases they may be easier to administration than prototypes. For example, the oral bioavailability is improved by prodrugs, but the bioavailability of the prototype drags is low by direct administration. Prodrugs can also improve the solubility of prototypes in pharmaceutical components. For example, some compounds of formula (I) have water solubility is too high to pass through cell membranes, while ester prodrugs may be more ready to pass the membranes. And then the carboxylic acid groups of prodrugs will be hydrolyzed by metabolism, so that the active substances can enter cells. Therefore, prodrugs will greatly favor the use of compounds of formula (I).

Prodrugs are usually precursors of the compounds, after administration and absorption, being converted into active substances or into more active forms through some processes, such as metabolic pathways. Some prodrugs have chemical groups that reduced their active and/or alter their solubility or other properties compared with those of the prototype compounds. Once the chemical groups of the prodrugs are removed and/or modified, the active substances can be obtained.

In another embodiment, prodrugs are designed as reversible compound derivatives and used as modifiers to enhance tissue distribution for drug delivery to specific locations. Specifically, for the tissue with water as the main solvent, the water solubility of these compounds can be increased through prodrug design.

In another embodiment, the compounds described herein are labeled with isotopes (e.g., radioisotope elements) or other means, including, but not limited to, chromophores or fluorescent groups, luminescence or chemiluminescence.

Term

Without further explanation, the terms used in the present invention are defined as follows. If there is no other clear indication, the singular form "one" and ("a") also includes the plural meaning of "one group of" or "one kind of". Without further explanation, this application uses conventional methods of mass spectrometry, nuclear magnetic resonance, high performance liquid chromatography, protein chemistry, biochemistry, recombinant DNA technology and pharmacology. In this application, the use of "or" and "and" may refer to "and/or" unless otherwise specified The term "carbonyl-containing cyclic compounds" used in the present invention refers to compounds which conform to general formula (I). "compounds of formula (I)" as used herein refers to the compounds conforming to structural formula (I).

The term "cosmetic composition" as used herein refers to a composition containing one or more form 1 compound and acceptable carriers in cosmetics, which can be used for skin care and makeup; the abovementioned skin care includes but is not limited to prevention of dermatitis and prevention of skin injuries.

The term "agonist" or "activator" as used herein refers to a compound that binds to and activates receptors, and induces physiological responses.

The term "high or higher blood-brain barrier permeability" as used herein refers to the fact that the new agonists involved in the present invention have a relatively higher penetration capacity through the blood-brain barrier compared with thiazolidinedione-type PPARγ agonists. Typical thiazolidinedione agonists include Rosiglitazone and Pioglitazone.

The term "alkyl" is used herein to refer to both straight- and branched-chain saturated aliphatic hydrocarbon groups having 1 to 12 carbon atoms.

The term "cycloalkyl" is used herein to refer to an alkyl group as previously described that is cyclic in structure and has about 3 to 10 carbon atoms.

The term "alkenyl" is used herein to refer to both straight- and branched-chain alkyl groups having one or more carbon-carbon double bonds and containing about 2 to 12 carbon atoms.

The term "acetylene" as used herein refers to both straight- and branched-chain alkyl groups having one or more carbon-carbon triple bonds and containing about 2 to 12 carbon atoms. The hydrogen atoms in the group are optionally substituted.

The term "heterocyclic" as used herein refers to an aliphatic or aromatic heterocyclic ring, which is saturated, partially unsaturated, or wholly unsaturated The term "carbonyl derivative" as used herein refers to a group of carbonyl-containing compounds derived by replacing one or more hydrogen atoms. The aforementioned "carbonyl" group is an organic functional group composed of carbon and oxygen atoms connected with double bonds, with the formula R—(C=O)—R'. Carbonyl derivatives include, but are not limited to, carbonyls, aldehydes (formula R—CH=O), ketones (formula R—(C=O)—R'), carboxylic acids (formula R—(C=O)—O—R'), esters (formula R—(C=O)—O—R'), amides (formula R—(CO)—NR'R'). R, R" refers to hydrogen atoms or any organic groups. Hydrogen atoms in these groups are optionally substituted.

The term "Phosphorus-containing group" as used herein refers to a group of phosphorus-containing compounds derived by replacing one or more hydrogen atoms, including but not limited to phosphine, phosphate and phosphite groups. Phosphine refers to all phosphine derivatives in which one or more hydrogen atoms are replaced by alkyl groups. Phosphate refers to the ester derivative of orthophosphate ($H_3PO_4$) after replacing one or more hydrogen atoms. Phosphite refers to the ester derivatives of phosphorous acid ($H_3PO_3$) after replacing one or more hydrogen atoms. The hydrogen atoms in these groups are optionally substituted The term "acceptable" as used herein refers to the fact that a prescription component or active ingredient has no excessive harmful effect on the health of a general treatment subject.

The term "metabolites" as used herein refers to the compounds identified from analysis of the tissue samples of a host after a compound was given to the host, or from analysis of the liver cells after coincubate compounds with the cells in vitro.

The term "treatment", "treatment process" or "therapy" as used herein refers to alleviating, inhibiting or improving symptoms or conditions of a disease; suppressing the occurrence of complications; improving or preventing potential metabolic syndromes; suppressing the occurrence of a disease or its symptoms, such as controlling the progress of a disease or condition; alleviating disease or symptoms; reducing complications caused by the disease or its symptom; or preventing or treating symptoms caused by a disease or condition.

Use of the Compounds

The carbonyl-containing cyclic compounds provide by the present invention can be used as medicaments to prevent and/or treat neurological disorders and strokes, inflammation and immune diseases, metabolic diseases, kidney diseases, cancers, etc.

The diseases or conditions referred to herein follow the established classifications of the industry. They can be classified herein under general headings, such as neurological disorders and inflammatory diseases. Those skilled in the art will appreciate that diseases or conditions referred to herein may be appropriately classified under different headings or under multiple headings. The invention is not limited by the classification of the diseases and/or disorders listed herein.

The compounds provided by the present invention can be used to prevent and/or treat neurological disorders and strokes. The abovementioned neurological disorders are selected from the group consisting of, but not limited to, dementia (mainly including Alzheimer's disease), vascular dementia, mixed dementia, Lewy body disease, frontotemporal dementia, secondary dementia, Huntington's disease, motor neuron disease, multisystem atrophy, progressive supranuclear palsy, normal pressure hydrocephalus, epilepsy, Parkinson's disease, stroke (stroke can also be classified as cardiovascular diseases because it is caused by vascular dysfunction), spinal cord injury, traumatic brain injury, Pick's disease, Niemann-Pick's disease, amyloid angiopathy, amyloid cerebrovascular disease, systemic amyloidosis. Hereditary cerebral hemorrhage with amyloidosis (e.g., Dutch type), inclusion body myositis, mild cognitive impairment, Down syndrome, amyotrophic lateral sclerosis (ALS), multiple sclerosis, Duchenne muscular dystrophy, Becker's muscular dystrophy. Facioscapulohumeral muscular dystrophy (FSHD), Limb-girdle muscular dystrophies (LGMD). The compounds provided by the present invention can be used to prevent and/or treat neuropathic pain, such as painful diabetic peripheral neuropathy, postherpetic neuralgia, cancer-related pains such as chemotherapy-induced peripheral neuropathy, spinal cord injury induced neuropathic pain, complex regional pain syndrome (CRPS), AIDS (Acquired immunodeficiency syndrome)-related pain, multiple sclerosis-related pain, phantom limb pain, post-stroke pain, trigeminal neuralgia, migraine, alcohol or drug abuse related pain, etc; inflammatory pain, such as arthritis pain; nociception pain, such as postoperative pain; and pain mixed with two or three types of the abovementioned pains (i.e., neuropathic pain, inflammatory pain, nociception pain), such as lower back pain. The compounds provided by the present invention can also be used to prevent and/or treat age-related eye disease (e.g., macular degeneration, cataract, glaucoma, diabetic retinopathy). The compounds provided by the present invention can be used to prepare the medicaments for preventing and/or treating the abovementioned diseases and conditions.

The compounds provided by the present invention can be used to prevent and/or treat inflammation and immune diseases. The abovementioned inflammation and immune diseases are selected from the group consisting of, but not limited to, lupus, arthritis (e.g. rheumatoid arthritis, psoriasis arthritis, osteoarthritis, ankylosing spondylitis), inflammation of the skin (psoriasis, dermatitis, scleroderma), intestinal inflammation (e.g. inflammatory bowel disease (IBD), Crohn's disease, ulcerative colitis, type I diabetes, multiple sclerosis, myasthenia gravis, vasculitis, asthma, atopic diseases (such as allergies), transplant/graft rejection, and graft-to-host disease, or other dysfunction of the immune system. The compounds provided by the present invention can be used to prepare the medicaments for preventing and/or treating the abovementioned diseases and conditions.

The compounds provided by the present invention can be used to prevent and/or treat metabolic diseases. The abovementioned metabolic diseases are selected from the group consisting of, but not limited to, diabetes (e.g. type 2 diabetes), dyslipidemia, arteriosclerosis, obesity, non-alcoholic fatty liver disease and/or other diseases. The compounds provided by the present invention can be used to prepare the medicaments for preventing and/or treating these diseases and conditions.

The compounds provided by the present invention can be used to prevent and/or treat kidney diseases. The abovementioned kidney diseases are selected from the group consisting of, acute kidney injury, chronic kidney disease, chronic glomerulonephritis, membranous nephritis, proliferative nephritis, chronic renal failure, diabetic nephropathy, hypertensive nephropathy, purpuric nephritis, lupus nephritis, IgA nephropathy, glomerulosclerosis, nephrotic syndrome, renal ischemia and/or uremia; but not limited to. The compounds provided by the present invention can be used to prepare the medicaments for preventing and/or treating the above-mentioned diseases and conditions.

The compounds provided by the present invention can be used to prevent and/or treat cancer diseases. The abovementioned cancer diseases are selected from the group consisting of, but not limited to. The abovementioned cancers are selected from the group consisting of, but not limited to, lung cancer, colorectal (e.g., colon cancer), gastric cancer, liver cancer, prostate cancer, esophageal cancer, bladder cancer, kidney cancer, pancreatic cancer, lymphoma, brain cancer (e.g. pituitary cancer, glioblastoma, brain metastases), leukemia, breast cancer, thyroid cancer, cervical cancer, uterine cancer, ovarian cancer, melanoma, other types of cancers. The compounds provided by the present invention can be used to prepare the medicaments for preventing and/or treating the abovementioned diseases and conditions.

The dosage requirements of the carbonyl-containing cyclic compound of the present invention may depend on the specific patient being treated and/or prevented, and the severity of symptoms of its disease or condition. Those skilled in the art can easily determine the required dose of carbonyl-containing cyclic compound. For example: in one embodiment, the dose is about 100-1000 mg/kg body weight/day, about 10-100 mg/kg body weight-day, about 1-10 mg/kg body weight/day, or about 0.1-1 mg/kg body weight/day. The compounds may be administered in combination with another drug at a dose of 1-10 mg/kg body weight/day or about 0.1-1 mg/kg body weight/day. At the beginning of treatment and/or prevention, carbonyl-containing cyclic compounds are administered in less than those required to produce the desired efficacy, usually less than the optimal dose of rosiglitazone and pioglitazone. Thereafter, the dose can be increased until optimal results are achieved in the patient's background. The exact dose is determined by the administering physician based on experience with the individual patient being treated and/or prevented. In general, it is most suitable to administer a composition of the present invention at a concentration that generally provides effective effects without causing any harmful or adverse side effects.

The compounds of the present invention can be used to prepare the preparation: the preparation can be prepared directly with the compounds of the present invention, or use any intermediate component obtained in the preparation of the compounds.

The present invention can be used in in vitro experiments for screening or verifying active ingredients for preventing or treating the diseases or symptoms described above. In the experiment for screening compounds, the compounds of formula (I), pharmaceutically acceptable salts or solvents thereof, or physiologically acceptable hydrolyzed products or derivatives with higher solubility, or solutions of immobilized derivatives thereof are specifically used to validate the compounds. These candidate compounds can be used to treat one or more of the diseases or conditions described above. Preferably, the compounds of formula (I) in the present invention can be used to confirm the ability of candidate compounds to activate the PPARγ receptor.

In recent years. PPARγ agonists have been found to increase mammalian klotho gene expression by activating PPARγ. In the literature 5 (King C D, et al. Identification of novel small molecules that elevate Klotho expression [J], Biochem J. 2012,441 (1): 453-461), a compound named N-(2-chlorophenyl)-1H-indole-3-amide was found to have an activity to increase the expression of klotho gene when the klotho gene to blindly screen some compounds. However, no carbonyl-containing cyclic compound was found to have an activity to increase the expression of klotho gene. The klotho gene was also not used to screen any PPARγ agonists.

The present invention uses the klotho gene to purposefully screen PPAR agonists. The new PPARγ agonists involved in the present invention are all carbonyl-containing cyclic compounds. Finally, the present invention identifies and selects a batch of PPARγ-activating and carbonyl-containing cyclic compounds that can increase klotho gene expression.

The activities of these carbonyl-containing cyclic compounds are indicated by the increased expression of klotho gene. Its activity is expressed by EC50, which means: the concentration of carbonyl-containing cyclic compounds that can cause 50% of the maximum effect (that is, the maximum expression of the klotho gene). The present invention retains the DNA fragment of the klotho gene promoter, but replaces the DNA sequence of the coding region of the klotho gene with those of luciferase, so that the degree of activation of the klotho gene promoter and the expression of the klotho gene will be sensitively determined by detecting the luciferase luminescence signal.

Transfection refers to the process by which eukaryotic cells acquire new genetic markers due to the incorporation of foreign DNA. Conventional transfection techniques can be divided into two categories: transient transfection and stable transfection (permanent transfection). The former does not integrate foreign DNA/RNA into the host chromosome, so there can be multiple copy numbers in a host cell, resulting in high-level expression, but usually lasts only a few days, and is mostly used for the analysis of promoters and other regulatory elements. In the latter scenario, foreign DNA can either be integrated into the host chromosome, or it can exist as an episome.

The term "KL-Luc" as used herein refers to a special exogenous DNA fragment containing two parts, KL and Luc. "KL" refers to the promoter region of the klotho gene. "Luc" refers to a coding fragment of Luciferase. Luciferase is used here as a reporter gene (a gene that encodes a protein or enzyme that can be detected). The luciferase fragment of the present invention may also be replaced with other reporter genes well known to those skilled in the art, for example, a secreted embryonic alkaline phosphatase (SEAP) reporter gene.

The term "cell strain" as used herein refers to cells derived either from a primary culture or a cell line by the selection or cloning of cells having specific properties or characteristics which must be defined. The term "stably transfected cell line" as used herein refers to a stably transfected cell line. These cell lines can be a human embryonic kidney cell line called HEK293, or other cell lines.

The term "representatives for compounds listed in Table 2" as used herein refers to any or all the following compounds from Table 2: ELB00824, ELB00727, ELB00702, ELB00993, ELB001045, ELB001046, ELB001115, ELB001125, ELB001201, and ELB001090.

The term "representatives for compounds listed in Table 3" as used herein refers to any or all the following compounds from Table 3: ELB00825, ELB001044, and ELB001056

Route of Administration

In one aspect, the present invention includes methods of preparing a pharmaceutical composition containing one or more carbonyl-containing cyclic compounds of the present invention. The composition can be administered to a mammalian subject by several different routes and is desirably administered orally in solid or liquid form.

Solid forms, including tablets, capsules, and caplets, containing the carbonyl-containing cyclic compound can be formed by blending the carbonyl-containing cyclic compound with one or more of the components described above. In one embodiment, the components of the composition are dry or wet blended. In another embodiment, the components are dry granulated. In a further embodiment, the components are suspended or dissolved in a liquid and added to a form suitable for administration to a mammalian subject.

Liquid forms containing the carbonyl-containing cyclic compound can be formed by dissolving or suspending the carbonyl-containing cyclic compound in a liquid suitable for administration to a mammalian subject.

Compositions containing the carbonyl-containing cyclic compound of the present invention can be prepared according to the present invention by combining the carbonyl-containing cyclic compound and a pharmaceutically acceptable carrier.

The compositions described herein containing the carbonyl-containing cyclic compound can be formulated in any form suitable for the desired route of delivery using a pharmaceutically effective amount of the carbonyl-containing cyclic compound. For example, the compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

The oral dosage tablet composition of this invention can also be used to make oral dosage tablets containing derivatives of the carbonyl-containing cyclic compound, including, but not limited to, esters, carbamates, sulfates, ethers, oximes, carbonates, and the like which are known to those of skill in the art.

A pharmaceutically effective amount of the carbonyl-containing cyclic compound can vary depending on the specific compound(s), mode of delivery, severity of the condition being treated, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

The carbonyl-containing cyclic compound of the present invention can be combined with one or more pharmaceutically acceptable carriers or excipients including, without limitation, solid and liquid carriers which are compatible with the compositions of the present invention. Such carriers include adjuvants, syrups, elixirs, diluents, binders, lubricants, surfactants, granulating agents, disintegrating agents, emollients, metal chelators, pH adjustors, surfactants, fillers, disintegrants, and combinations thereof, among others. In one embodiment, the carbonyl-containing cyclic compound is combined with metal chelators, pH adjustors, surfactants, fillers, disintegrants, lubricants, and binders.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Binders can include, without limitation, cellulose, methylcellulose, hydroxymethylcellulose, carboxymethylcellulose calcium, carboxymethylcellulose sodium, hydroxypropylcellulose, hydroxypropylmethylcellulose phthalate, microcrystalline cellulose, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone, hydroxypropylmethylcellulose, carboxymethylcellulose, or gelatin. In another embodiment, the binder is povidone.

Lubricants can include magnesium stearate, light anhydrous silicic acid, talc, stearic acid, sodium lauryl sulfate, and sodium stearyl furamate, among others. In one embodiment, the lubricant is magnesium stearate, stearic acid, or sodium stearyl furamate. In another embodiment, the lubricant is magnesium stearate.

Granulating agents can include, without limitation, silicon dioxide, microcrystalline cellulose, starch, calcium carbonate, pectin, crospovidone, and polyplasdone, among others.

Disintegrating agents or disintegrants can include croscarmellose sodium, starch, carboxymethylcellulose, substituted hydroxypropylcellulose, sodium bicarbonate, calcium phosphate, calcium citrate, sodium starch glycolate, pregelatinized starch or crospovidone, among others. In one embodiment, the disintegrant is croscarmellose sodium.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

A pH adjuster can also be utilized to adjust the pH of a solution containing the carbonyl-containing cyclic compound to about 4 to about 6. In one embodiment, the pH of a solution containing the carbonyl-containing cyclic compound is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Fillers that can be used according to the present invention include anhydrous lactose, microcrystalline cellulose, mannitol, calcium phosphate, pregelatinized starch, or sucrose, hi one embodiment, the filler is anhydrous lactose. In another embodiment, the filler is microcrystalline cellulose.

In one embodiment, compositions containing the carbonyl-containing cyclic compound of the invention are delivered orally by tablet, caplet or capsule, microcapsules, dispersible powder, granule, suspension, syrup, elixir, and aerosol. Desirably, when compositions containing the carbonyl-containing cyclic compound are delivered orally, delivery is by tablets and hard- or liquid-filled capsules.

In another embodiment, the compositions containing the carbonyl-containing cyclic compound can be delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile and stable under conditions of manufacture and storage, and free of the contaminating action of microorganisms such as bacteria and fungi.

In a further embodiment, compositions containing the carbonyl-containing cyclic compound can be delivered rectally in the form of a conventional suppository.

In another embodiment, compositions containing the carbonyl-containing cyclic compound can be delivered vaginally in the form of a conventional suppository, cream, gel, ring, or coated intrauterine device (IUD).

In another embodiment, compositions containing the carbonyl-containing cyclic compound can be delivered via coating or impregnating of a supporting structure, i.e., a framework capable of containing of supporting pharmaceutically acceptable carrier or excipient containing a compound of the invention, e.g., vascular stents or shunts, coronary stents, peripheral stents, catheters, arterio-venous grafts, by-pass grafts, and drug delivery balloons for use in the vasculature. In one embodiment, coatings suitable for use include, but are not limited to, polymeric coatings composed of any polymeric material in which the compounds of the invention is substantially soluble. Supporting structures and coating or impregnating methods, e.g., those described in Reference 6 (U.S. Pat. No. 6,890,546), are known to those of skill in the art and are not a limitation of the present invention.

In yet another embodiment, compositions containing the carbonyl-containing cyclic compound can be delivered intranasally or intrabronchially in the form of an aerosol.

The carbonyl-containing cyclic compounds are administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions are advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

The carbonyl-containing cyclic compounds are also administered parenterally or intraperitoneally. Solutions or suspensions of these active compounds as a free base or pharmacologically acceptable salt are prepared in water suitably mixed with a surfactant such as hydroxypropylcellulose. Dispersions are also prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringe ability exits. It is stable under conditions of manufacture and storage and is preserved against the contaminating action of microorganisms such as bacterial and fungi. The carrier is a solvent or dispersion medium containing, for example, water, ethanol (e.g., glycerol, propylene glycol and liquid polyethylene glycol), suitable mixtures thereof, and vegetable oil.

All features described in this specification (including any described claims, abstract, and figures), and/or all steps involved in any method or process, may exist in any combination, unless certain features or steps are mutually exclusive in the same combination.

The embodiments described herein are provided to illustrate the invention and do not limit the scope thereof. It will be readily apparent to one skilled in the art that varying substitutions and modifications can be made which are meant to be encompassed by the spirit and scope of the invention.

Example 1

Preparation of Compound 2 [ELB00824, (E)-6-(4-(4-ethylphenyl)but-1-en-1-yl)-2,3-dihydro-1H-inden-1-one]

Step 1: Preparation of Compound 1 [1-(but-3-en-1-yl)-4-ethylbenzene]

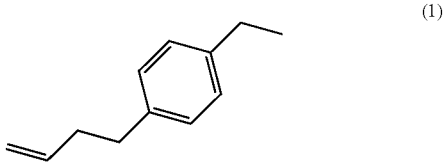

(1)

Method 1: Under the protection of argon, magnesium powder (1.04 g, 0.043 mole) was added to a 500 mL three neck flask. Iron trichloride (300 mg, 0.00178 mole) was dissolved in 200 mL of anhydrous tetrahydrofuran, and slowly dropped into a three neck flask, and then tetramethylethylenediamine (5.00 g, 0.043 mole) was dropped into the three neck flask. Stir at room temperature for 20 minutes, and then the temperature of the reaction system was reduced to 0° C. by ice water bath. Paraethyl bromobenzene (6.6 g, 0.036 mole) and 4-bromo-1-butene (5.8 g, 0.043 mole) were slowly added dropwise to the reaction system and the reaction was monitored by thin-layer chromatography (TLC) for 3 hours. After the reaction completed, saturated ammonium chloride solution (50 mL) was added to quench the reaction. To quench the reaction and concentrate the products, water (150 mL) were added, and extracted three times with 150 mL ethyl acetate. Organic phases were combined, washed with water and saturated sodium chloride, dried over anhydrous magnesium sulfate, filtered and concentrated. The crude product was purified by column chromatography (organic phase:petroleum ether) to obtain 3 g (52%) colorless liquid compound 1.

Method 2: 4-ethylbenzaldehyde (0.90 g, 6.67 millimole) was weighed and added to a 25 mL round-bottom flask. 1M allylmagnesium bromide/ether solution (8 mL, 8.0 millimole) was added to the flask in ice water bath. After 2 hours stirring at 0° C. The reaction was monitored with TLC. When complete, to concentrate the products, water (10 mL) were added, stirred for 10 minutes, and extracted three times with 10 mL ethyl acetate. Organic phases were combined, washed with water and saturated sodium chloride, dried with anhydrous sodium sulfate, then filtered and concentrated to obtain 0.72 g (61%) colorless liquid 1-(4-ethylphenyl)-3-ene-1-ol(1-(4-ethylphenyl)but-3-en-1-ol). Triethoxysilane (2.1 g, 18.36 millimole) was added to the mixture, and boron trifluoride/ether solution (6.13 millimole) was added to the ice bath. After 2 hours stirring at 0° C. The reaction was monitored with TLC. When complete, to concentrate the products, water (10 mL) were added, stirred for 10 minutes, and extracted three times with 15 mL ethyl acetate. Organic phases were combined, washed with water and saturated sodium chloride, dried with anhydrous sodium sulfate, filtered and concentrated, and the crude product was purified by column chromatography (mobile phase:petroleum ether:ethyl acetate=5:1). 4.7 g (72%) colorless transparent liquid was obtained.

The colorless transparent liquid obtained by method 1 and method 2 is compound 1 [(1-(but-3-en-1-yl)-4-ethylbenzene)]. The physical property is as follows: $^1$H NMR (400 MHz, CDCl$_3$): δ1.20 (t, 3H), 1.26 (m, 2H), 1.75 (m, 2H), 4.89 (m, 2H), 5.92 (m, 1H), 7.14 (m, 4H).

Step 2: Preparation of Compound 2 [(E)-6-(4-(4-ethylphenyl)but-1-en-1-yl)-2,3-dihydro-1H-inden-1-one]

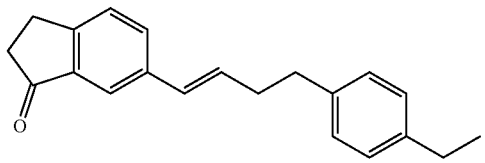

(2)

Under argon protection, 6-bromo-1-indene (112 mg, 0.53 millimole), compound 1 (140 mg, 0.80 millimole), palladium acetate (6 mg, 0.027 millimole), tri(o-methylphenyl)phosphine (16 mg, 0.053 millimole) were added into 25 mL three neck flask, and then triethylamine (1.5 mL), N, N-dimethylformamide (1.5 mL) were added. The reaction system was heated to 100° C. in oil bath and stirred for 6 hours. The reaction was monitored with TLC. When complete, the temperature was reduced to room temperature. To quench the reaction and concentrate the products, water (10 mL) were added, stirred for 10 minutes, and extracted three times with 15 mL ethyl acetate. Organic phases were combined, washed with water and saturated sodium chloride, dried with anhydrous sodium sulfate, filtered and concentrated, and the crude product was purified by column chromatography (mobile phase:ethyl acetate:petroleum ether=1:5). 70 mg (44%) yellow solid was obtained. The yellow solid is compound 2 [(E)-6-(4-(4-ethylphenyl)but-1-en-1-yl)-2,3-dihydro-1H-inden-1-one]. The physical property is as follows: $^1$H NMR (400 MHz, CDCl$_3$): δ1.25 (t, 3H), 2.23 (dd, 2H), 2.60 (m, 4H), 2.71 (m, 2H), 3.12 (m, 2H), 6.38 (m, 2H), 7.11 (m, 4H), 7.65 (m, 3H).

Example 2

Preparation of Compound 3 [ELB00825, 6-(4-(4-ethylphenyl)butyl)-2,3-dihydro-1H-inden-1-one]

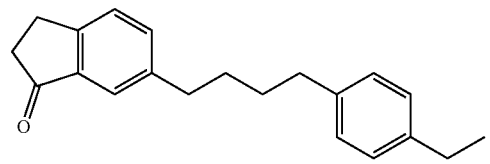

(3)

Compound 2 (1.2 g) was weighed, added to 50 mL autoclave, dissolved in 10 mL methanol, and then added with palladium on carbon (100 mg) and hydrogen. The autoclave temperature was set at 50° C. and the pressure at 1 Mpa. After 2 hours of reaction, the system temperature was lowered to room temperature, palladium on carbon was filtered, and filtrate was concentrated. The crude product was purified by column chromatography (mobile phase: ethyl acetate:petroleum ether=1:6). 1.1 g (91.7%) yellow solid was obtained. The yellow solid is compound 3 [6-(4-(4-ethylphenyl)butyl)-2,3-dihydro-1H-inden-1-one]. The physical property is as follows: $^1$H NMR (400 MHz, CDCl$_3$): δ1.23 (t, 3H), 2.23 (m, 4H), 2.60 (m, 8H), 3.14 (t, 2H), 7.11 (m, 4H), 7.65 (m, 3H).

Example 3

Preparation of Compound 5 [ELB00727, (E)-7-(4-(4-ethylphenyl)but-1-en-1-yl)-3,4-dihydroquinolin-2(1H)-one]

Step 1: Preparation of Compound 4 [(E)-6-((E)-4-(4-ethylphenyl)but-1-en-1-yl)-2,3-dihydro-1H-inden-1-one oxime]

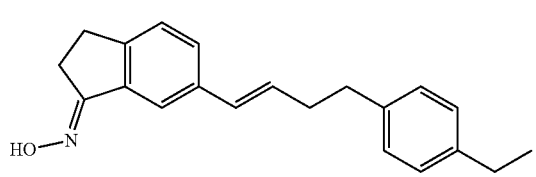

(4)

Compounds 2 (50 mg, 0.172 millimole), hydroxylamine hydrochloride (18 mg, 0.258 millimole), sodium acetate (26 mg, 0.31 millimole) were weighed and added into 25 mL three neck flask, and 3 mL absolute ethanol was added. The reaction was stirred for 3 hours at room temperature and monitored with TLC. When complete, to concentrate the products, water (3 mL) were added, and extracted three times with 5 mL ethyl acetate. Organic phases were combined, washed with water and saturated sodium chloride, dried with anhydrous sodium sulfate, then filtered and concentrated. 55 mg crude product was obtained without purification and was directly used for the next reaction.

Step 2: Preparation of Compound 5 [(E)-7-(4-(4-ethylphenyl)but-1-en-1-yl)-3,4-dihydroquinolin-2(1H)-one]

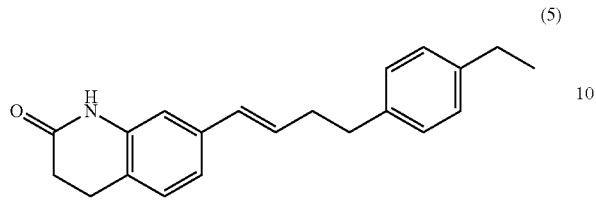

(5)

Compound 4 (30 mg) was weighed and added into three neck flask. 5 mL polyphosphoric acid was added into three neck flask. The reaction system was heated in an oil bath and stirred for 2 hours at 80° C. The system temperature was lowered to room temperature. The reaction was added with 5 mL water and stirred for 10 minutes to quench the reaction. The organic phase was extracted three times with 15 mL ethyl acetate, washed with water and saturated sodium chloride, dried with anhydrous sodium sulfate, filtered and concentrated, and the crude product was purified by column chromatography (mobile phase:ethyl acetate:petroleum ether=1:6). 20 mg (66%) yellow solid was obtained. The yellow solid is compound 5 [(E)-7-(4-(4-ethylphenyl)but-1-en-1-yl)-3,4-dihydroquinolin-2(1H)-one]. The physical property is as follows: $^1$H NMR: (400 MHz, D4-DMSO): δ 1.14 (t, 3H), 2.54 (dd, 2H), 2.74 (m, 2H), 3.03 (m, 4H), 3.34 (m, 2H), 6.42 (m, 2H), 7.11 (m, 4H), 7.42 (m, 1H), 7.57 (m, 1H), 7.67 (m, 1H).

Example 4

Preparation of Compound 6 [ELB00702, 7-(4-(4-ethylphenyl)butyl)-3,4-dihydroquinolin-2(1H)-one]

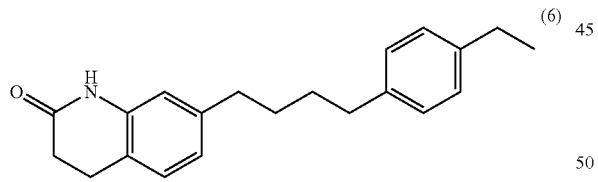

(6)

Compound 5 (1 g) was weighed, added to 50 mL autoclave, and then added with 10 mL methanol, palladium on carbon (100 mg), and hydrogen. The autoclave temperature and pressure were set at 50° C. and 1 Mpa. After 2 hours of reaction, the system temperature was lowered to room temperature, and palladium on carbon was filtered. The filtrate was concentrated, and crude product was purified by column chromatography (mobile phase:ethyl acetate:petroleum ether=1:6). 950 mg (95%) yellow solid was obtained. The yellow solid is compound 6 [7-(4-(4-ethylphenyl)butyl)-3,4-dihydroquinolin-2(1H)-one], The physical property is as follows: $^1$H NMR (400 MHz, D4-DMSO): δ1.14 (t, 3H), 1.24 (m, 2H), 1.32 (m, 2H), 2.56 (m, 2H), 2.78 (m, 2H), 3.09 (m, 4H), 3.36 (m, 2H), 7.13 (m, 4H), 7.45 (m, 1H), 7.56 (m, 1H), 7.69 (m, 1H).

Example 5

Preparation of Compound 12 [ELB00827, 8-(4-(4-ethylphenyl)butyl)-2,3-dihydrobenzo[b][1,4]oxazepin-4(5H)-one]

Step 1: Preparation of Compound 7 [3-(3-bromophenoxy)propanoic acid]

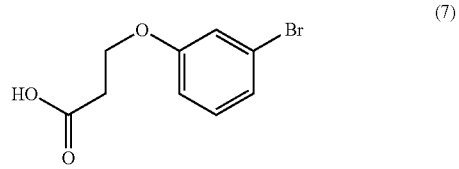 [SMILES: O=C(O)CCOc1cccc(Br)c1]

(7)

3-chloropropionic acid (10.8 g, 0.1 mole) and 3-bromophenol (17.3 g, 0.1 mole) were added to 1000 mL three neck flask respectively. Sodium hydroxide aqueous solution (500 mL, 4.8 mole/L) was added and mixed. The mixed solution was stirred at room temperature for 2 hours, and the color of the solution turned yellow. The reaction was monitored with TLC. When complete, concentrated hydrochloric acid (12 mole/L) was added slowly to adjust the solution pH to 2. Precipitation occurs in the solution, was filtered and dried. 21 g (85%) pale yellow solid was obtained. The pale yellow solid is compound 7 (3-(3-bromophenoxy) propionic acid). The physical property is as follows: $^1$H NMR (400 MHz, CDCl$_3$): δ2.65 (t, 2H), 4.21 (t, 2H), 6.93 (m, 1H), 7.20 (m, 3H).

Step 2: Preparation of Compound 8 (7-bromochroman-4-one)

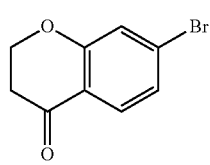

(8)

Compound 7 (5 g) was weighed and added into three neck flask. 50 mL polyphosphoric acid was added and mixed. The reaction system was heated in an oil bath and stirred for 2 hours at 80° C. Then the temperature was lowered to room temperature, and the reaction was quenched with 100 mL water by stirring for 10 minutes. The organic phase was extracted three times with 100 mL ethyl acetate, washed with water and saturated sodium chloride, dried with anhydrous sodium sulfate, filtered and concentrated, and the crude product was purified by column chromatography (mobile phase:ethyl acetate:petroleum ether=1:3). 3.1 g (60%) yellow solid was obtained. The yellow solid is compound 8 (7-bromochroman-4-one). The physical property is as follows: $^1$H NMR (40 MHz, CDCl$_3$): δ2.80 (t, 2H), 4.55 (t, 2H), 7.15 (dd, 1H), 7.25 (s, 1H), 7.71 (t, 1H).

Step 3: Preparation of Compound 9 [ELB001045, (E)-7-(4-(4-ethylphenyl)but-1-en-1-yl)chroman-4-one]

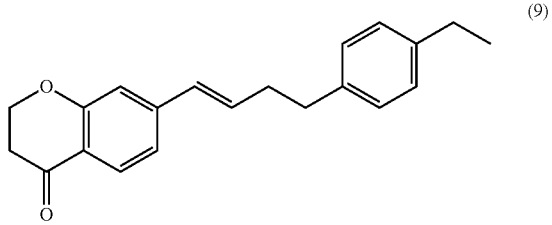 [SMILES: CCc1ccc(CC/C=C/c2ccc3c(c2)OCCC3=O)cc1]

(9)

Compounds 8 (1 14 mg, 0.50 millimole), compound 1 (130 mg, 0.81 millimole), palladium acetate (6 mg, 0.027 millimole), tri(o-methylphenyl) phosphine (16 mg, 0.053 millimole) were added into 25 mL triple bottle under argon protection, and triethylamine (1.5 mL), N, N-dimethylformamide (1.5 mL) were mixed into the reaction system. The reaction system was heated to 100° C. in oil bath, stirred for 5 hours. The reaction was monitored with TLC. When complete, the temperature was lowered to room temperature. The reaction was quenched with 5 mL water by stirring for 10 minutes. The organic phase was extracted three times with 15 mL ethyl acetate, washed with water and saturated sodium chloride, dried with anhydrous sodium sulfate, filtered and concentrated, and the crude product was purified by column chromatography (mobile phase:ethyl acetate: petroleum ether=1:4). 83 mg (54%) yellow solid was obtained. The yellow solid is compound 9 [(E)-7-(4-(4-ethylphenyl)but-1-en-1-yl)chroman-4-one]. The physical property is as follows: $^1$H NMR (400 MHz, CDCl$_3$): δ1.22 (t, 3H), 2.25 (dd, 2H), 2.63 (m, 4H), 2.69 (t, 2H), 4.12 (t, 2H), 6.39 (m, 2H), 7.21 (m, 4H), 7.75 (m, 3H).

Step 4: Preparation of Compound 10 [(E)-7-((E)-4-(4-ethylphenyl)but-1-en-1-yl)chroman-4-one oxime]

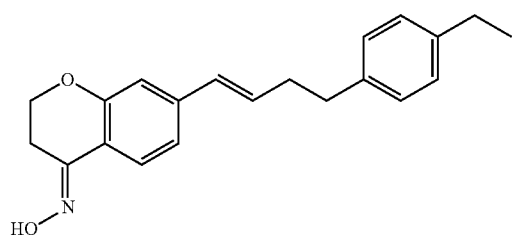

(10)

Compounds 9 (100 mg, 0.33 millimole), hydroxylamine hydrochloride (36 mg, 0.52 millimole), sodium acetate (52 mg, 0.62 millimole), 5 mL absolute ethanol were added into 25 mL three neck flask. Mixture was stirred for 3 hours at room temperature. The reaction was monitored with TLC. When complete, to concentrate the products, water (50 mL) were added, and extracted three times with 10 mL ethyl acetate. Organic phases were combined, washed with water and saturated sodium chloride, dried with anhydrous sodium sulfate, filtered and concentrated. The crude product of 110 mg was obtained without purification. The product was compound 10 [(E)-7-((E)-4-(4-ethylphenyl)but-1-en-1-yl)chroman-4-one oxime], which could be directly used in the next reaction.

Step 5: Preparation of Compound 11 [ELB00992, (E)-8-(4-(4-ethylphenyl)but-1-en-1-yl)-2,3-dihydrobenzo[b][1,4]oxazepin-4(5H)-one]

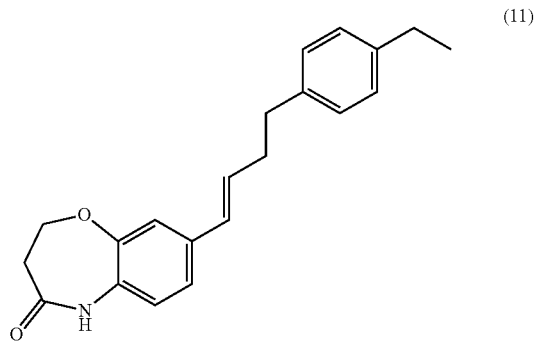 [SMILES: CCc1ccc(CC/C=C/c2ccc3c(c2)OCCC(=O)N3)cc1]

(11)

Compound 10 (80 mg) was weighed and 5 mL polyphosphoric acid was added into three neck flask and mixed. The reaction system was heated in oil bath and stirred at 80° C. for 2 hours. Then the temperature of the system was lowered to room temperature, and 5 mL water was added to quench the reaction. The organic phase was extracted three times with 15 mL ethyl acetate, washed with water saturated sodium chloride, dried with anhydrous sodium sulfate, filtered and concentrated, and the crude product was purified by column chromatography (mobile phase:ethyl acetate: petroleum ether=1:5). 40 mg (50%) yellow solid was obtained. The yellow solid is compound 11 (ELB00992, (E)-8-(4-(4-ethylphenyl)but-1-en-1-yl)-2,3-dihydrobenzo[b][1,4]oxazepin-4(5H)-one). The physical property is as follows: $^1$H NMR (400 MHz, CDCl$_3$): δ1.25 (t, 3H), 2.29 (dd, 2H), 2.59 (m, 4H), 2.82 (t, 2H), 4.38 (t, 2H), 6.55 (m, 2H), 7.02 (m, 4H), 7.75 (m, 3H).

Step 6: Preparation of Compound 12 [8-(4-(4-ethylphenyl)butyl)-2,3-dihydrobenzo[b][1,4]oxazepin-4(5H)-one]

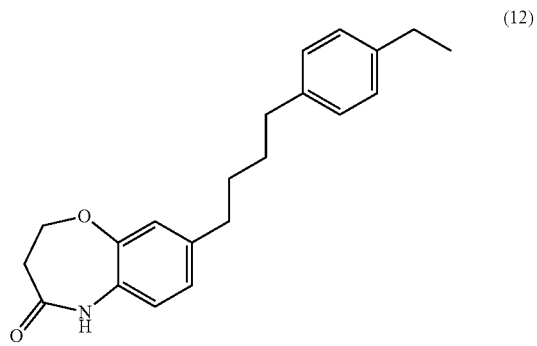 [SMILES: CCc1ccc(CCCCc2ccc3c(c2)OCCC(=O)N3)cc1]

(12)

By a similar preparation method for compound 3, compound 11 (2.3 g) and palladium on carbon (230 mg) were reacted to yield 2.2 g (96%) white solid. The white solid is compound 12 [8-(4-(4-ethylphenyl)butyl)-2,3-dihydrobenzo

[b][1,4]oxazepin-4(5H)-one]. The physical property is as follows: $^1$H NMR (400 MHz, CDCl$_3$): δ1.27 (t, 3H), 2.25 (dd, 2H), 2.59 (m, 6H), 2.84 (t, 2H), 4.39 (t, 2H), 7.03 (m, 4H), 7.72 (m, 3H).

Example 6

Preparation of Compound 18 [ELB00532, 6-(6-(4-ethylphenyl)hexyl)isochroman-4-one]

Step 1: Preparation of Compound 13 [4-bromo-2-(hydroxymethyl)benzoic acid]

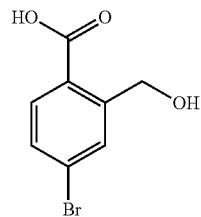

(13)

6-bromo-3H-isobenzofuran-1-one (5.0 g, 23.47 millimole) was weighed, and tetrahydrofuran:methanol:water (2:1:1, 80 mL) were measured and also added into three neck flask. After dissolution by stirring for 10 minutes, lithium hydroxide (3.45 g, 70.42 millimole) was added and stirred for 16 hours at room temperature. The reaction was monitored with TLC. When complete, the solution was concentrated. 100 mL water added to the reaction solution, and pH were adjusted to 3 with 2N hydrochloric acid. The products were extracted three times with 100 mL ethyl acetate. Organic phases were combined, washed with water and saturated sodium chloride, dried with anhydrous sodium sulfate, filtered and concentrated to obtain 3.3 g (91%) white solid. The white solid is compound 13 [4-bromo-2-(hydroxymethyl)benzoic acid]. The physical property is as follows: $^1$H NMR (400 MHz, CD$_3$OD): 7.88-7.86 (m, 2H), 7.45 (dd, 1H), 4.90 (s, 2H).

Step 2: Preparation of Compound 14 [4-bromo-2-((carboxymethoxy)methyl)benzoic acid]

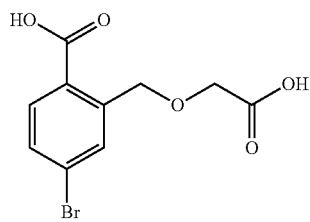

(14)

Compounds 13 (5.0 g, 21.64 millimole), bromoacetic acid (2.99 g, 21.64 millimole), tetrahydrofuran (60 mL) were added into three neck flask, stirred for 10 minutes, dissolved, batched with sodium hydride (3.46 g, 86.56 millimole) within half an hour, then sodium iodide (324.6 mg, 2.164 millimole) was added, and stirred at 70° C. for 16 hours, and The reaction was monitored with TLC. When complete, the reaction system was lowered to room temperature, water (150 mL) was added, and pH was adjusted to 3 with 2N hydrochloric acid. The products were extracted three times with 100 mL ethyl acetate. Organic phases were combined, washed with water and saturated sodium chloride, dried with anhydrous sodium sulfate, filtered and concentrated to obtain 4.27 g (70%) white solid. The white solid is compound 14 [4-bromo-2-((carboxymethoxy)methyl)benzoic acid]. The physical property is as follows: $^1$H NMR (400 MHz, CD$_3$OD) 7.93-7.87 (m, 2H), 7.55-7.52 (m, 1H), 4.98 (s, 2H), 4.23 (s, 2H).

Step 3: Preparation of Compound 15 [7-bromoisochroman-4-one]

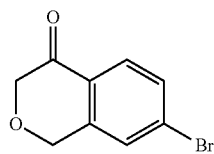

(15)

Compounds 14 (5.2 g, 18.06 millimole) were weighed. The acetic anhydride (100 mL) was measured, added into three neck flask, and stirred for 10 minutes. Potassium acetate (7.61 g, 77.64 millimole) was added, stirred for 2 hours at 100° C., and then the reaction system was lowered to room temperature. To quench the reaction and concentrate the products, water (100 mL) was added, the mixture were extracted three times with 100 mL ethyl acetate. Organic phase were combined, washed with water and saturated sodium chloride, dried with anhydrous sodium sulfate, filtered, concentrated, dissolved with ethanol (50 mL), added with sodium hydroxide (2.89 g, 72.24 millimole), and stirred for 2 hours at room temperature. To further concentrate the products, the mixture was added with water (100 mL), extracted three times with 100 mL ethyl acetate. Organic phases were combined, washed with water and saturated sodium chloride, dried with anhydrous sodium sulfate, filtered and concentrated, and the crude product was purified by column chromatography (mobile phase:ethyl acetate: petroleum ether=1:1). 725 mg (18%) yellow solid was obtained. The yellow solid is compound 15 [7-bromoisochroman-4-one]. The physical property is as follows: $^1$HNMR (400 MHz, CDCl$_3$) 5: 7.90 (d, 1H), 7.56 (dd, 1H), 7.42 (s, 1H), 4.86 (s, 2H), 4.36 (s, 2H).

Step 4; Preparation of Compound 16 [1-ethyl-4-(hex-5-en-1-yl)benzene]

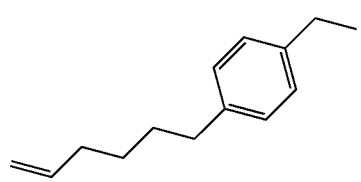

(16)

Under argon protection, magnesium powder (200 mg, 6.5 millimole) was added into 100 mL three neck flask. Ferric trichloride (50 mg, 0.3 millimole) was dissolved in 25 mL anhydrous tetrahydrofuran and slowly dripped into three neck flask. Tetramethylethylenediamine (800 mg, 6.5 millimole) was added into three neck flask. Stir at room temperature for 20 minutes. The temperature of the reaction system was lowered to 0° C. by ice-water bath. p-Ethyl bromobenzene (1 g, 5.4 millimole) and 6-bromo-1-hexene (1.1 g, 6.5 millimole) were separately weighed and slowly added to the reaction system, and then stirred at 0° C. for 3 hours. The reaction was monitored with TLC. When complete, 5 mL saturated ammonium chloride solution was added, stirred for 10 minutes, and then 15 mL water was added. The organic phase was extracted three times with 50 mL ethyl acetate, washed with water and saturated sodium chloride solution, dried with anhydrous sodium sulfate, filtered and concentrated, and the crude product was purified by column chromatography (mobile phase:petroleum ether). 400 mg (40%) colorless transparent liquid was obtained. The colorless transparent liquid is compound 16 [1-ethyl-4-(hex-5-en-1-yl)benzene], The physical property is as follows: $^1$H NMR (400 MHz, CDCl$_3$): δ1.24 (t, 3H), 1.44 (m, 2H), 1.65 (m, 2H), 2.10 (dd, 2H), 2.61 (m, 2H), 4.99 (m, 2H), 5.82 (m, 1H), 7.11 (m, 4H).

Preparation of Compound 17 [(E)-7-(6-(4-ethylphenyl)hex-1-en-1-yl)isochroman-4-one]

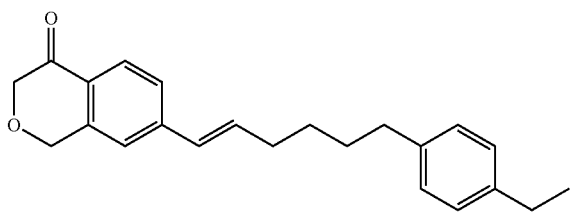

(17)

By a similar preparation method for compound 2, 110 mg (33%) white solid was obtained by the reaction of compound 15 (227 mg, 1 millimole) with compound 16 (282 mg, 1.5 millimole). The white solid is compound 17 [(E)-7-(6-(4-ethylphenyl)hex-1-en-1-yl)isochroman-4-one]. The physical property is as follows: $^1$H NMR (400 MHz, CDCl$_3$): δ1.25 (t, 3H), 2.23 (dd, 2H), 2.60 (m, 4H), 4.38 (s, 2H), 4.56 (s, 2H), 6.38 (m, 2H), 7.11 (m, 4H), 7.65 (m, 3H).

Step 6: Preparation of Compound 18 [6-(7-(4-ethylphenyl)hexyl)isochroman-4-one]

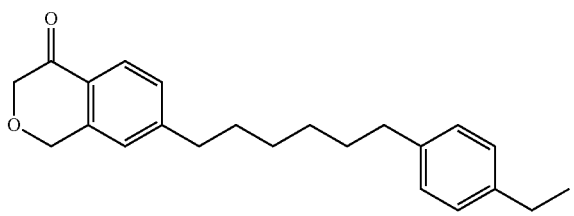

(18)

By a similar preparation method for compound 3, the reaction of compound 17 (3.3 g) with palladium on carbon (330 mg) yielded 3.2 g (96%) of white solid. The white solid is compound 18 [ELB00532, 6-(7-(4-ethylphenyl)hexyl) isochroman-4-one], The physical property is as follows: $^1$H NMR (400 MHz, CDCl$_3$): δ1.25 (t, 3H), 2.23 (dd, 2H), 2.60 (m, 6H), 4.37 (s, 2H), 4.53 (s, 2H), 7.18 (m, 4H), 7.69 (m, 3H).

Example 7

Preparation of Compound 21 [ELB00533, 6-(4-(4-ethylphenyl)butyl)-2H-benzo[b][1,4]oxazin-3(4H)-one]

Step 1: Preparation of Compound 19 [6-bromo-2H-benzo[b][1,4]oxazin-3(4H)-one]

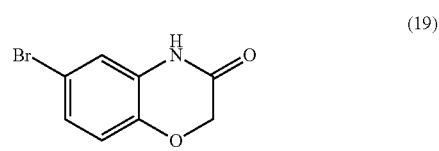 [SMILES: O=C1COc2ccc(Br)cc2N1]

(19)

2-amino-4-bromophenol (2.5 g, 13 millimole) was added into three neck flask, 80 mL tetrahydrofuran, and triethylamine (2.4 mL, 17 millimole) were added into the system. The reaction system was cooled to 0° C., and then dripped with chloroacetyl chloride (1.12 mL, 14 millimole). After stirred for 10 minutes at 0° C., the temperature was raised to room temperature for 2 hours, and then reduced to 0° C. Sodium hydride (1.05 g, 26 millimole) was added in batches. The reaction system was reduced to 0° C. for 20 minutes and then increased to room temperature for 2 hours. To quench the reaction and concentrate the products, 100 mL water was added to quench the reaction. Precipitation was filtered, washed, and dried. 2.5 g red solid was obtained. The red solid is compound 19 [6-bromo-2H-benzo[b][1,4]oxazin-3 (4H)-one]. The physical property is as follows: $^1$H NMR (400 MHz, CDCl$_3$): δ4.62 (s, 2H), 6.86 (d, 1H), 6.96 (d, 1H), 7.09 (dd, 1H).

Step 2: Preparation of Compound 20 [ELB00993, (E)-6-(4-(4-ethylphenyl)but-1-en-1-yl)-2H-benzo[b][1,4]oxazin-3(4H)-one]

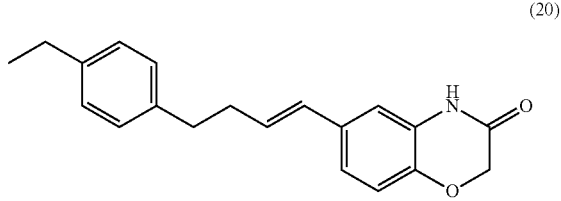 [SMILES: CCc1ccc(CC/C=C/c2ccc3c(c2)NC(=O)CO3)cc1]

(20)

By a similar preparation method for compound 5, the reaction of compound 19 (200 mg, 0.877 millimole) with compound 1 (150 mg, 1.05 millimole) yielded 100 mg (37.1%) yellow solid. The yellow solid is compound 20 [ELB00993, (E)-6-(4-(4-ethylphenyl)but-1-en-1-yl)-2H-benzo[b][1,4]oxazin-3(4H)-one]. The physical property is as follows: $^1$H NMR (400 MHz, CDCl$_3$): δ1.25 (t, 3H), 2.29 (m, 2H), 2.58 (m, 4H), 4.79 (s, 2H), 6.28 (m, 2H), 6.92 (m, 1H), 7.06 (m, 4H), 7.36 (m, 1H), 7.69 (m, 1H).

Step 3: Preparation of Compound 21 [ELB00533, 6-(4-(4-ethylphenyl)butyl)-2H-benzo[b][1,4]oxazin-3(4H)-one]

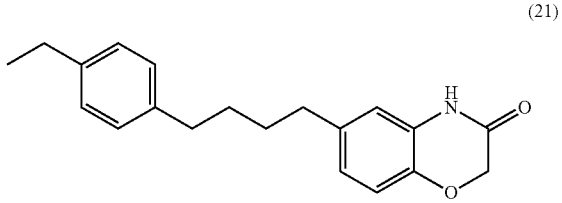 [SMILES: CCc1ccc(CCCCc2ccc3c(c2)NC(=O)CO3)cc1]
(21)

By a similar preparation method for compound 3, the reaction of compound 20 (1.8 g) with palladium on carbon (180 mg) yielded a white solid of 1.7 g (95%). The white solid is compound 21 [ELB00533, 6-(4-(4-ethylphenyl) butyl)-2H-benzo[b][1,4]oxazin-3(4H)-one]. The physical properly is as follows: $^1$H NMR (400 MHz, CDCl$_3$): δ1.25 (t, 3H), 1.59 (m, 4H), 2.61 (m, 6H), 4.78 (s, 2H), 6.93 (m, 1H), 7.09 (m, 4H), 7.39 (m, 1H), 7.69 (m, 1H).

Example 8

Preparation of Compound 26 [ELB00923, (R)-2-((3-(3-(4-ethylphenyl)propyl)phenyl)methyl)-1-methylimidazolidin-4-one]

Step 1: Preparation of Compound 22 [2-(3-bromobenzyl)imidazolidin-4-one]

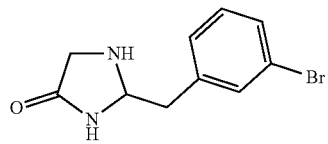
(22)

Compound 22 was obtained from the reaction of glycinamide hydrochloride (2.21 g, 20 millimole) with 3-bromophenylacetaldehyde (1.99 g, 10 millimole) in 5 mL triethylamine and 50 mL methanol in three neck flask. The reaction was heated first at 60° C. for 12 hours. To quench the reaction and concentrate the products, water (50 mL) were added, stirred for 30 minutes, and extracted three times with 50 mL ethyl acetate. Organic phases were combined, washed with water and saturated sodium chloride, dried with anhydrous sodium sulfate, filtered and concentrated. The crude product was purified by column chromatography (mobile phase:ethyl acetate:petroleum ether=1:6) to obtain 1.8 g (71%) white solid The white solid is compound 22 [2-(3-bromobenzyl)imidazolidin-4-one]. The physical property is as follows: $^1$H NMR (400 MHz, CDCl$_3$): δ2.98 (d, 2H), 3.45 (dd, 2H), 5.10 (t, 1H), 7.31 (m, 4H).

Step 2: Preparation of Compound 23 [2-(3-bromobenzyl)-1-methylimidazolidin-4-one]

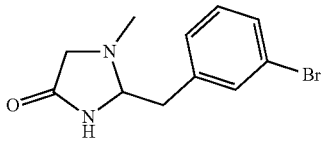
(23)

Compound 22 (2.69 g, 10 millimole), 50 mL tetrahydrofuran were added into three neck flask, cooled to 0° C., then sodium hydride (0.4 g, 10 millimole) was added in batches, stirred at 0° C. for 30 minutes, and then iodized methane (1.56 g, 11 millimole) was dripped into the reaction system. The temperature was raised to room temperature for 6 hours. To quench the reaction and concentrate the products, water (50 mL) were added, stirred for 10 minutes, and extracted three times with 50 mL ethyl acetate. Organic phases were combined, washed with water and saturated sodium chloride, dried with anhydrous sodium sulfate, filtered and concentrated. 2.51 g (90%) yellow liquid was obtained, which is compound 58 (2-(5-bromofuran-2-yl)-1-methylimidazolidin-4-one). The products need not be purified and can be directly used for the next reaction, named compound 23 [2-(3-bromobenzyl)-1-methylimidazolidin-4-one]. The products need not be purified and can be directly used for the next reaction.

Step 3: Preparation of Compound 24 [1-allyl-4-ethylbenzene]

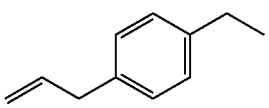
(24)

By a similar preparation method for compound 1, 380 mg (48%) colorless transparent liquid was obtained from the reaction of p-ethyl bromobenzene (1 g, 5.4 millimole) and 3-bromo-1-propylene (0.79 g, 6.5 millimole). The colorless transparent liquid is compound 24 [1-allyl-4-ethylbenzene]. The physical property is as follows: $^1$H NMR (400 MHz, CDCl$_3$): δ1.23 (t, 3H), 2.11 (dd, 2H), 2.61 (m, 2H), 4.99 (m, 2H), 5.82 (m, 1H), 7.13 (m, 4H).

Step 4: Preparation of Compound 25 [ELB00984, ((E)-2-(3-(3-(4-ethylphenyl)prop-1-en-1-yl)benzyl)-1-methylimidazolidin-4-one]

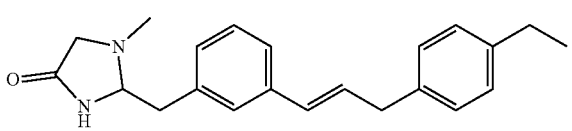
(25)

By a similar preparation method for compound 2, the reaction of compound 23 (2.69 g, 0.01 mole) with compound 24 (2.19 g, 0.015 mole) yielded 1.67 g (50%) white solid. The white solid is compound 25 [ELB00984, ((E)-2-(3-(3-(4-ethylphenyl)prop-1-en-1-yl)benzyl)-1-methylimidazolidin-4-one]. The physical property is as follows: $^1$H NMR (400 MHz, CDCl$_3$): δ1.24 (t, 3H), 2.26 (s, 3H), 2.70 (m, 4H), 3.23 (m, 4H), 5.11 (t, 1H), 6.55 (m, 2H), 6.98 (d, 2H), 7.18 (m, 5H), 7.42 (m, 1H).

Step 5: Preparation of Compound 26 [ELB00923, (2R)-2-((3-(3-(4-ethylphenyl)propyl)phenyl)methyl)-1-methylimidazolidin-4-one]

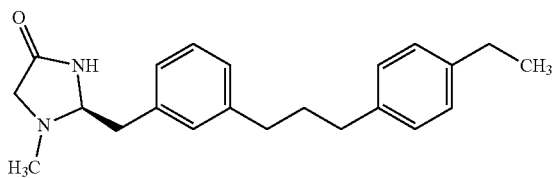

(26)

A colourless liquid of 80 mg was obtained by the reaction of compound 25 (110 mg) with palladium on carbon (11 mg) by a similar preparation method for compound 3. After purification by chiral analysis column, 25 mg (24%) white solid was obtained. The white solid is compound 26 [ELB00923, (2R)-2-((3-(3-(4-ethylphenyl)propyl)phenyl)methyl)-1-methylimidazolidin-4-one]. The physical property is as follows: $^1$H NMR (400 MHz, CDCl$_3$): δ1.25 (t, 3H), 1.95 (m, 2H), 2.61 (m, 6H), 3.03 (m, 2H), 3.49 (dd, 2H), 5.13 (t, 1H), 7.05 (m, 7H), 7.57 (m, 1H).

Example 9

Preparation of Compound 28 [ELB001056, 5-(4-(4-ethylphenyl)butyl)-2,3-dihydro-1-benzofuran-3-one]

Step 1: Preparation of Compound 27 [ELB001044, (E)-5-(4-(4-ethylphenyl)but-1-en-1-yl)benzofuran-3(2H)-one]

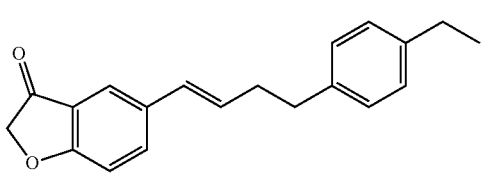

(27)

By a similar preparation method for compound 2, 181 mg (62%) white-like solids were obtained by the reaction of 5-bromo-3-benzofuranone (213.03 mg, 1 millimole) with compound 1 (240.39 mg, 1.5 millimole). This kind of white solid is compound 27 [ELB001044, (E)-5-(4-(4-ethylphenyl)but-1-en-1-yl)benzofuran-3(2H)-one]. The physical property is as follows: $^1$H NMR (400 MHz, CDCl$_3$): δ1.25 (t, 3H), 2.30 (dd, 2H), 2.58 (t, 2H), 2.71 (dd, 2H), 5.23 (s, 2H), 6.06 (m, 1H), 6.42 (d, 1H), 7.03 (m, 5H), 7.23 (s, 1H), 7.80 (d, 1H).

Step 2: Preparation of Compound 28 [5-(4-(4-ethylphenyl)butyl)-2,3-dihydro-1-benzofuran-3-one]

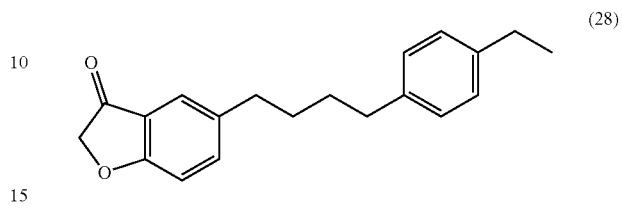

(28)

By a similar preparation method for compound 3, the reaction of compound 27 (100 mg) with palladium on carbon (10 mg) yielded 89 mg (88%) white-like solids. The white solid is compound 28 [ELB001056, 5-(4-(4-ethylphenyl)butyl)-2,3-dihydro-1-benzofuran-3-one]. The physical property is as follows: $^1$H NMR (400 MHz, CDCl$_3$): δ1.25 (t, 3H), 1.63 (t, 4H), 2.68 (m, 6H), 5.23 (s, 2H), 7.03 (d, 5H), 7.33 (d, 1H), 7.80 (s, 1H).

Example 10

Preparation of Compound 29 [ELB001046, (E)-6-(4-(4-ethylphenyl)but-1-en-1-yl)isochroman-4-one]

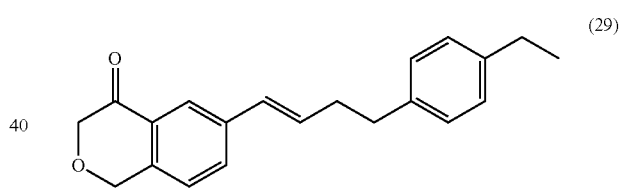

(29)

Under argon protection, 6-bromo-4-isodihydrochromone (20 mg, 0.088 millimole), compound 1 (28.16 mg, 0.176 millimole), palladium acetate (0.9878 mg, 0.0044 millimole), tri(o-methylphenyl)phosphine (2.6787 mg, 0.0088 millimole), triethylamine (0.5 mL), and N, N-dimethylformamide (0.5 mL) were added. The reaction system was heated to 110° C. in oil bath, stirred overnight, monitored by TLC, and decreased to room temperature. To quench the reaction and concentrate the products, water (2 mL) were added, stirred for 10 minutes, and extracted three times with 5 mL ethyl acetate. Organic phases were combined, washed with water and saturated sodium chloride, dried with anhydrous sodium sulfate, filtered and concentrated, and the crude product was purified by column chromatography (mobile phase:ethyl acetate:petroleum ether=1:10). 18.9 mg (70%) yellow liquid was obtained. The yellow liquid is compound 29 [ELB001046, (E)-6-(4-(4-ethylphenyl)but-1-en-1-yl)isochroman-4-one]. The physical property is as follows: $^1$H NMR (400 MHz, CDCl$_3$): δ1.23 (t, 3H), 2.31 (m, 2H), 2.60 (t, 2H), 2.75 (dd, 2H), 4.63 (d, 4H), 6.09 (m, 1H), 6.44 (d, 1H), 7.05 (s, 4H), 7.30 (t, 2H), 7.86 (d, 1H)

Example 11

Preparation of Compound 30 [ELB001058, 6-(4-(4-ethylphenyl)butyl)isochroman-4-one]

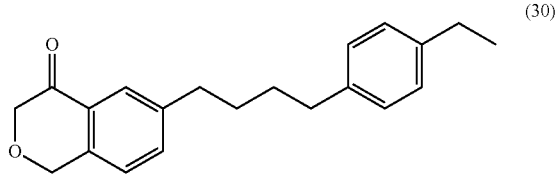 [SMILES: CCc1ccc(CCCCc2ccc3c(c2)C(=O)COC3)cc1]

(30)

By a similar preparation method for compound 3, the reaction of compound 29 (16 mg) with palladium on carbon (0.8 mg) yielded 14.2 mg (88%) of white solid. The white solid is compound 30 [ELB001058, 6-(4-(4-ethylphenyl)butyl)isochroman-4-one]. The physical property is as follows: $^1$H NMR (400 MHz, CDCl$_3$): δ1.25 (t, 3H), 1.64 (m, 6H), 2.75 (m, 6H), 4.63 (d, 4H), 7.06 (s, 4H), 7.28 (d, 1H), 7.39 (d, 1H), 7.78 (s, 1H).

Example 12

Preparation of Compound 32 [(B)-6-(4-(4-ethylphenyl)but-1-en-1-yl)-5-hydroxy-2,3-dihydro-1H-inden-1-one]

Step 1: Preparation of Compound 31 [5-hydroxy-6-iodo-2,3-dihydro-1H-inden-1-one]

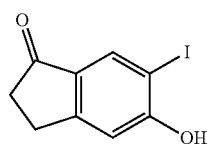

(31)

5-hydroxy-1-indene (1.48 g, 0.01 mole) and N-iodosuccinimide (2.25 g, 0.01 mole) were dissolved in 20 mL acetonitrile and stirred overnight at room temperature. The solvent was steamed, dried, washed with ethyl acetate, filtered and dried again. The obtained solid was recrystallized in acetonitrile and 0.92 g (33%) product was obtained which is compound 31 [5-hydroxy-6-iodo-2,3-dihydro-1H-inden-1-one]. The crude product was directly used in the next step.

Step 2: Preparation of Compound 32 [(H)-6-(4-(4-ethylphenyl)but-1-en-1-yl)-5-hydroxy-2,3-dihydro-1H-inden-1-one]

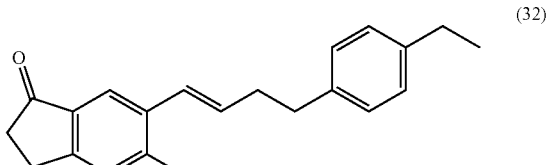

(32)

Compound 31 (274 mg, 1 millimole) was reacted with compound 1 (240 mg, 1.5 millimole) to obtain 168 mg (55%) white solids, named compound 32 [(E)-6-(4-(4-ethylphenyl)but-1-en-1-yl)-5-hydroxy-2,3-dihydro-1H-inden-1-one]. The physical property is as follows: $^1$H NMR (400 MHz, CDCl$_3$): δ1.23 (t, 3H), 2.33 (m, 2H), 2.70 (m, 4H), 3.09 (t, 2H), 5.89 (m, 1H), 6.75 (t, 2H), 7.07 (d, 5H), 10.28 (s, 1H).

Example 13

Preparation of Compound 34 [ELB001115, (E)-6-(3-(4-ethylphenoxy)prop-1-en-1-yl)-2,3-dihydro-1H-inden-1-one]

Step 1: Preparation of Compound 33 [1-(allyloxy)-4-ethylbenzene]

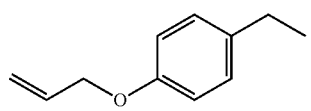

(33)

p-Ethylphenol (1 g, 8.186 millimole) was dissolved in 14 mL acetone, added with anhydrous potassium carbonate (1.2445 g, 9.005 millimole) and 3-bromopropylene (1.089 g, 9.005 millimole), and refluxed for 14 hours. The reaction liquid was added 35 mL water and extracted three times with 4 mL ethyl acetate. The organic phase was washed with 1M sodium hydroxide aqueous solution (15 mL), dried with anhydrous magnesium sulfate, and the solvent was removed by decompression. The crude product was purified by column chromatography (mobile phase:n-hexane:ethyl acetate=9:1) to yield 0.9 g (68%) colorless liquid, named compound 33 [1-(allyloxy)-4-ethylbenzene].

Step 2: Preparation of Compound 34 [ELB001115, (E)-6-(3-(4-ethylphenoxy)prop-1-en-1-yl)-2,3-dihydro-1H-inden-1-one]

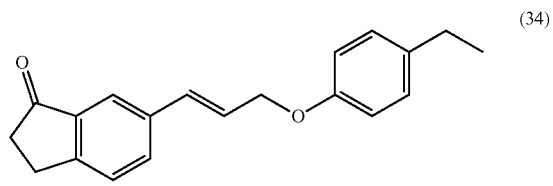 [SMILES: CCc1ccc(OC/C=C/c2ccc3c(c2)C(=O)CC3)cc1]

(34)

6-Bromo-1-indolone (112 mg, 0.53 millimole) and compound 33 (128.97 mg, 0.80 millimole) were reacted by a similar preparation method for compound 2. 45.3 mg (29%) pale yellow liquid and 15.1 mg (10%) pale yellow solid were obtained as compound 34 [ELB001115, (E)-6-(3-(4-ethylphenoxy)prop-1-en-1-yl)-2,3-dihydro-1H-inden-1-one)]. The physical property is as follows: $^1$H NMR (400 MHz, CDCl$_3$): δ1.24 (t, 3H), 2.59 (t, 2H), 2.75 (dd, 2H), 3.18 (t, 2H), 4.70 (d, 2H), 6.25 (m, 1H), 6.66 (d, 1H), 6.80 (d, 2H), 7.00 (d, 2H), 7.25 (m, 2H), 7.83 (d, 1H).

Example 14

Preparation of Compound 36 [ELB001116, (E)-6-(4-(4-methoxyphenyl)but-1-en-1-yl)-2,3-dihydro-1H-inden-1-one]

Step 1: Preparation of Compound 35 [1-(but-3-en-1-yl)-4-methoxybenzene]

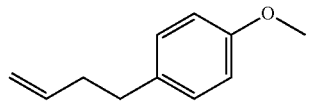
(35)

4-methoxychlorobenzyl (1.5661 g, 0.01 mole) was dissolved in 20 mL tetrahydrofuran, and then 1M allyl magnesium bromide/tetrahydrofuran solution (20 mL, 0.02 mole) was added under nitrogen protection. The reaction time was 4 hours at room temperature. The reaction was quenched in saturated ammonium chloride aqueous solution. The products were extracted with dichloromethane. Organic phase was dried with anhydrous magnesium sulfate, and isolated by column chromatography (mobile phase:n-hexane). 1.48 g (91%) pale yellow liquid was obtained, named compound 35 [1-(but-3-en-1-yl)-4-methoxybenzene].

Step 2: Preparation of Compound 36 [ELB001116, (E)-6-(4-(4-methoxyphenyl)but-1-en-1-yl)-2,3-dihydro-1H-inden-1-one]

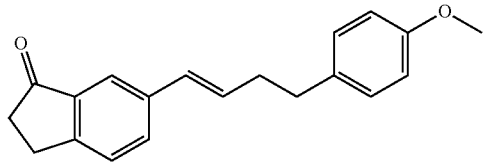
(36)

By a similar preparation method for compound 2, the reaction of 6-bromo-1-indene (112 mg, 0.53 millimole) with compound 35 (129.8 mg, 0.80 millimole) yielded 68.18 mg (44%) white solid, named compound 36 [ELB001116, (E)-6-(4-(4-methoxyphenyl)but-1-en-1-yl)-2,3-dihydro-1H-inden-1-one]. The physical property is as follows: $^1$H NMR (400 MHz, CDCl$_3$): δ2.32 (dd, 2H), 2.28 (m, 2H), 3.19 (t, 2H), 3.81 (s, 3H), 6.05 (m, 1H), 6.47 (d, 1H), 6.88 (d, 2H), 7.14 (d, 2H), 7.26 (m, 2H), 7.85 (d, 1H).

Example 15

Preparation of Compound 38 [ELB001125, (E)-6-(4-(5-ethylpyridin-2-yl)but-1-en-1-yl)-2,3-dihydro-1H-inden-1-one]

Step 1: Preparation of Compound 37 [2-(but-3-en-1-yl)-5-ethylpyridine]

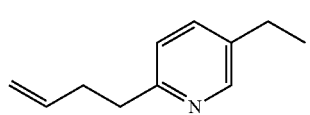
(37)

Under argon protection, 5-ethyl-2-methyl-pyridine (1 g, 8.25 millimole) was dissolved in 6 mL ether, cooled to −70° C., slowly dripped with n-butyl lithium/ether solution (8.25 millimole), and stirred for 0.5 hours at a constant temperature. 3-bromopropylene (1 g, 8.25 millimole) was dissolved in 5 mL ether, slowly dripped into the reaction system, and then reacted for 0.5 hours. To quench the reaction and concentrate the products, water (10 mL) were added, and extracted three times with 10 mL ethyl acetate. Organic phases were combined, washed with water and saturated sodium chloride, dried with anhydrous MgSO$_4$. After concentration, 1.05 g (79%) colorless liquid was obtained by column chromatography, named compound 37 [2-(but-3-en-1-yl)-5-ethylpyridine].

Step 2: Preparation of Compound 38 [ELB001125, (E)-6-(4-(5-ethylpyridin-2-yl)but-1-en-1-yl)-2,3-dihydro-1H-inden-1-one]

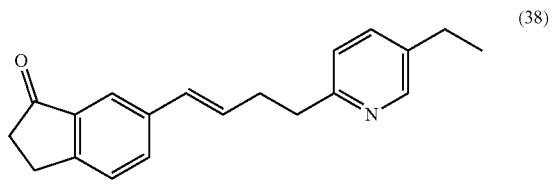 [SMILES: CCc1ccc(CC/C=C/c2ccc3c(c2)C(=O)CC3)nc1]
(38)

By a similar preparation method for compound 2, compound 37 (129 mg, 0.80 millimole) was reacted with 6-bromo-1-indene (112 mg, 0.53 millimole) to yield 182 mg (78%) white solid, which is compound 38 [ELB001125, (E)-6-(4-(5-ethylpyridin-2-yl)but-1-en-1-yl)-2,3-dihydro-1H-inden-1-one]. The physical property is as follows: $^1$H NMR (400 MHz, CDCl$_3$), δ1.29 (t, 3H), 2.31 (m, 2H), 2.59 (t, 2H), 2.77 (dd, 2H), 2.93 (t, 2H), 3.16 (t, 2H), 6.09 (m, 1H), 6.44 (d, 1H), 7.08 (d, 1H), 7.26 (m, 2H), 7.53 (d, 1H), 7.86 (d, 1H), δ1.30 (s, 1H).

Example 16

Preparation of Compound 40 [ELB001084, (E)-6-(4-(3-methoxyphenyl)but-1-en-1-yl)-2,3-dihydro-1H-inden-1-one]

Step 1: Preparation of Compound 39 [1-(but-3-en-1-yl)-3-methoxybenzene]

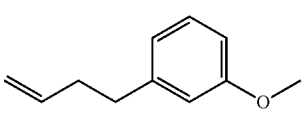
(39)

The reaction of 3-methoxybenzyl chloride (1.5661 g, 0.01 mole) with allyl magnesium bromide yields 1.3 g (82%) pale yellow liquid, which is compound 39 [1-(but-3-en-1-yl)-3-methoxybenzene]

Step 2: Preparation of Compound 40 [ELB001084, (E)-6-(4-(3-methoxyphenyl)but-1-en-1-yl)-2,3-dihydro-1H-inden-1-one]

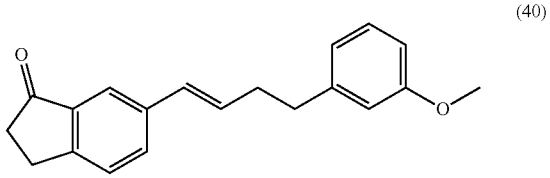 [SMILES: COc1cccc(CC/C=C/c2ccc3c(c2)C(=O)CC3)c1]

(40)

By a similar preparation method for compound 2, the reaction of 6-bromo-1-indene (112 mg, 0.53 millimole) with compound 39 (129.8 mg, 0.80 millimole) yielded 34 mg (22%) white solid, named compound 40 [ELB001084, (E)-6-(4-(3-methoxyphenyl)but-1-en-1-yl)-2,3-dihydro-1H-inden-1-one]. The physical property is as follows: $^1$H NMR (400 MHz, CDCl$_3$): δ2.32 (dd, 2H), 2.58 (m, 4H), 3.19 (t, 2H), 3.71 (s, 3H), 6.05 (m, 1H), 6.47 (d, 1H), 6.88 (m, 3H), 7.26 (m, 3H), 7.85 (d, 1H).

Example 17

Preparation of Compound 42 [ELB001201, (E)-6-(6-(4-ethylphenyl)hex-1-en-1-yl)-2,3-dihydro-1H-inden-1-one]

Step 1: Preparation of Compound 41 [1-ethyl-4-(hex-5-en-1-yl)benzene]

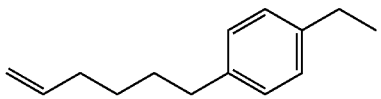

(41)

Method 1: Magnesium powder (1.04 g, 0.043 mole) was added into 500 mL three neck flask under argon protection. Ferric trichloride (300 mg, 0.00178 mole) was dissolved in 200 mL anhydrous tetrahydrofuran and slowly dripped into three neck flask. Tetramethylethylenediamine (5.00 g, 0.043 mole) was added into three neck flask, and stirred at room temperature for 20 minutes. The temperature of the reaction system was lowered to 0° C. by ice-water bath. p-Ethyl bromobenzene (6.6 g, 0.036 mole) and 6-bromo-1-hexene (7.0 g, 0.043 mole) were weighed respectively and added slowly to the reaction system, and then stirred for 3 hours at 0° C. The reaction was monitored by TLC. When completed, 50 mL saturated ammonium chloride solution was added and stirred for 10 minutes. To quench the reaction and concentrate the products, water (150 mL) were added, and extracted three times with 150 mL ethyl acetate. Organic phases were combined, washed with water and saturated sodium chloride, dried with anhydrous sodium sulfate, filtered and concentrated, and the crude product was purified by column chromatography (mobile phase:petroleum ether). 7.1 g (62%) colorless transparent liquid was obtained, which is compound 41 [1-ethyl-4-(hex-5-en-1-yl)benzene].

Method 2: 4-ethylbenzaldehyde (0.90 g, 6.67 millimole) was weighed and added to 25 mL round bottom flask. 4-enonyl magnesium bromide/tetrahydrofuran solution (8.0 millimole) was added to the flask in ice water bath. The reaction was stirred for 2 hours at 0° C., and monitored by TLC. When complete, to quench the reaction and concentrate the products, water (10 mL) were added, stirred for 10 minutes, and extracted three times with 15 mL ethyl acetate. Organic phases were combined, washed with water and saturated sodium chloride, dried with anhydrous sodium sulfate, filtered and concentrated to obtain 0.72 g (61%) colorless liquid 4-(4-ethylphenyl)-1-butene-4-ol. Triethoxysilane (2.1 g, 18.36 millimole) was added to the mixture, and boron trifluoride/ether solution (6.13 millimole) was added to the ice bath. The reaction was stirred for 2 hours at 0° C., and monitored by TLC. When complete, to quench the reaction and concentrate the products, water (10 mL) were added, stirred for 10 minutes, and extracted three times with 15 mL ethyl acetate. Organic phases were combined, washed with water and saturated sodium chloride, dried with anhydrous sodium sulfate, filtered and concentrated, and the crude product was purified by column chromatography (mobile phase:petroleum ether:ethyl acetate=5:1). 4.7 g (72%) colourless transparent liquid was obtained, i.e. compound 41 [1-ethyl-4-(hex-5-en-1-yl)benzene].

Step 2: Preparation of Compound 42 [ELB001201, (E)-6-(6-(4-ethylphenyl)hex-1-en-1-yl)-2,3-dihydro-1H-inden-1-one]

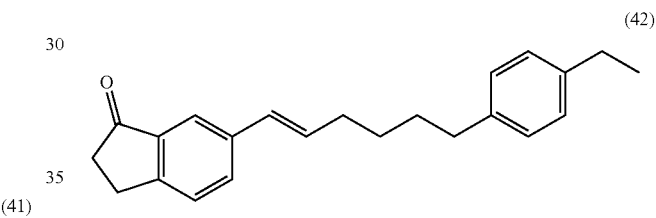

(42)

By a similar preparation method for compound 2, the reaction of 6-bromo-1-indene (112 mg, 0.53 millimole) with compound 41 (150.65 mg, 0.80 millimole) yielded 70.9 mg (42%) white solid, named compound 42 [ELB001201, (E)-6-(6-(4-ethylphenyl)hex-1-en-1-yl)-2,3-dihydro-1H-inden-1-one]. The physical property is as follows: $^1$H NMR (400 MHz, CDCl$_3$): δ1.29 (m, 5H), 1.59 (m, 2H), 2.17 (dd, 2H), 2.69 (m, 6H), 3.18 (t, 2H), 6.09 (m, 1H), 6.47 (d, 1H), 7.09 (s, 4H), 7.26 (m, 2H), 7.89 (d, 1H).

Example 18

Preparation of Compound 43 [ELB001090, 2-(3-(3-(4-ethylphenyl) prop-1-en-1-yl)benzyl)imidazolidin-4-one]

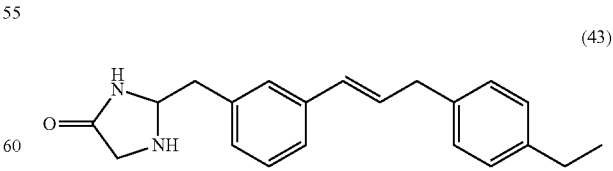

(43)

By a similar preparation method for compound 2, the reaction of compound 22 (2.55 g, 0.01 mole) with compound 24 (2.19 g, 0.015 mole) yielded 1.38 g (43%) white solid, named compound 43 [ELB001090, 2-(3-(3-(4-ethylphenyl) prop-1-en-1-yl)benzyl)imidazolidin-4-one]. The physical property is as follows: ¹H NMR (400 MHz, CDCl₃): δ1.22 (t, 3H), 2.77 (m, 4H), 3.39 (m, 4H), 5.15 (t, 1H), 6.39 (m, 2H), 6.69 (m, 1H), 7.09 (m, 4H), 7.23 (m, 6H), 7.51 (m, 3H).

Example 19

Preparation of Compound 44 [ELB001091, 2-(3-(3-(4-ethylphenyl)propyl)benzyl)imidazolidin-4-one]

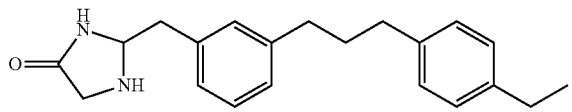

(44)

By a similar preparation method for compound 3, compound 43 (2.3 g) reacted with palladium on carbon (230 mg) to obtain 2.0 g (86%) white solid, which is compound 44 [ELB001091, 2-(3-(3-(4-ethylphenyl)propyl)benzyl)imidazolidin-4-one]. The physical property is as follows: ¹H NMR (400 MHz, CDCl₃): δ1.21 (t, 3H), 1.97 (m, 2H), 2.76 (m, 8H), 3.49 (dd, 2H), 5.14 (t, 1H), 6.39 (s, 1H), 7.15 (m, 8H), 7.51 (t, 1H).

Example 20

Preparation of Compound 45 (ELB001057, 7-(4-(4-ethylphenyl)butyl)chroman-4-one

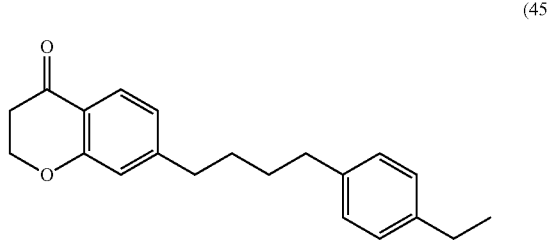

(45)

By a similar preparation method for compound 3, the reaction of compound 9 (100 mg) with palladium on carbon (10 mg) yields 90 mg (90%) white-like solid, named compound 45 [ELB001057, 7-(4-(4-ethylphenyl)butyl) chroman-4-one]. The physical property is as follows: ¹H NMR (400 MHz, CDCl₃): δ1.20 (t, 3H), 1.62 (t, 3H), 2.73 (m, 3H), 4.66 (d, 4H), 6.96 (d, 1H), 7.05 (t, 4H), 7.37 (s, 1H), 1.02 (d, 1H).

Example 21

Preparation of Compound 48 [ELB001203, 6-((1E)-4-(3-ethylphenyl)but-1-en-1-yl)-2,3-dihydro-1H-inden-1-one]

Step 1: Preparation of Compound 46 [1-(3-ethylphenyl)but-3-en-1-ol]

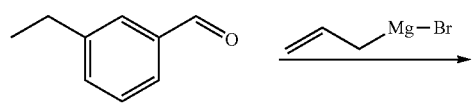

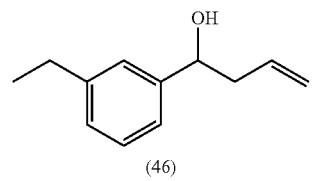

(46)

Weigh 3-ethylbenzaldehyde (2.68 g, 20 millimole) into a round bottom flask, and cool the system temperature to 0° C. in an ice water bath. With stirring, a 1M Allylmagnesium bromide/Diethyl ether solution (24 mL, 24 millimole) was slowly added dropwise. After the dropwise addition was completed, the reaction was stirred at 0° C. for 4 hours. After the reaction was monitored by thin layer chromatography, 10 mL of saturated aqueous ammonium chloride solution was added to quench the reaction. It was extracted three times with 10 mL of ethyl acetate, and the organic phases were combined. The organic phases were washed with water and saturated aqueous sodium chloride solution, dried over anhydrous sodium sulfate overnight, filtered and concentrated. The crude product was purified by column chromatography (mobile phase:petroleum ether:ethyl acetate=5:1) to obtain 2.86 g (81% yield) of a colorless transparent liquid, referred as Compound 46 [1-(3-ethylphenyl)but-3-en-1-ol].

Step 2: Preparation of Compound 47 [1-(but-3-en-1-yl)-3-ethylbenzene]

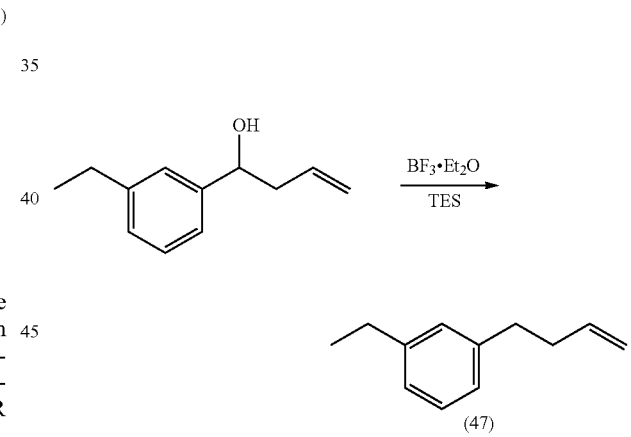

(47)

Weigh Compound 46 (1.76 g, 10 millimole), triethoxysilane (5.6 g, 48 millimole), add to the round bottom flask, ice water bath to reduce the temperature of the system to 0° C. Boron trifluoride/ether solution (4.9 g, 16 millimole) was slowly added dropwise with stirring. Stir the reaction overnight at 0° C. After monitoring the reaction by thin layer chromatography, add 20 mL of saturated aqueous ammonium chloride solution to quench the reaction, extract three times with 30 mL of ethyl acetate, combine the organic phases, and wash the organic phases with water and saturated aqueous sodium chloride solution, respectively. Dry over anhydrous sodium sulfate overnight, filler and concentrate. The crude product was purified by column chromatography (mobile phase:petroleum ether:ethyl acetate=5:1) to obtain 1.36 g (85% yield) of a light yellow transparent liquid, referred as Compound 47 [1-(but-3-en-1-yl)-3-ethylbenzene].

Step 3: Preparation of Compound 48 [ELB001203, 6-((1E)-4-(3-ethylphenyl)but-1-en-1-yl)-2,3-dihydro-1H-inden-1-one]

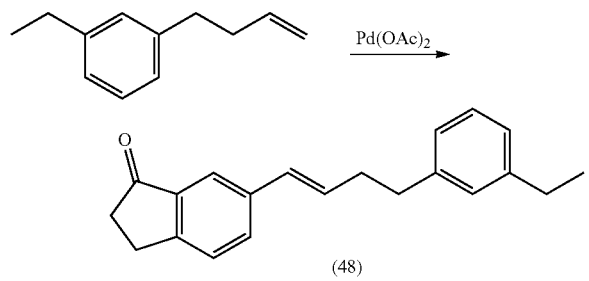

(48)

Weigh 6-bromoindenone (0.62 g, 3 millimole), Compound 47 (0.64 g, 4 millimole), palladium acetate (34 mg, 0.15 millimole), tris(o-methylphenyl)phosphine (92.5 mg, 0.30 millimole) Add a round bottom flask. Under the protection of argon, triethylamine (3 mL) and N,N-dimethylformamide (3 mL) were added, and the reaction was stirred at 110° C. overnight. After monitoring the reaction by thin layer chromatography, 5 mL of saturated aqueous ammonium chloride solution was added to quench the reaction, and extracted three times with 10 mL of ethyl acetate. The organic phases were combined, and the organic phase was washed with water and saturated aqueous sodium chloride solution, and dried over anhydrous sodium sulfate overnight. Filter and concentrate. The crude product was purified by column chromatography (mobile phase:petroleum ether:ethyl acetate=5:1) to obtain 0.58 g of light yellow oily liquid (67% yield), named compound 48 [ELB001203, 6-((1E)-4-(3-ethylphenyl)but-1-en-1-yl)-2,3-dihydro-1H-inden-1-one]. The physical property is as follows: 1H NMR (400 MHz, CDCl3): δ1.23 (t, 3H), 2.59 (d, 2H), 2.63 (d, 2H), 2.68 (d, 2H), 3.05 (m, 4H), 3.53 (m, 4H), 5.96 (s, 1H), 6.57 (s, 1H), 6.98 (s, 1H), 7.08 (m, 2H), 7.17 (s, 1H), 7.23 (s, 1H), 7.32 (s, 1H), 7.85 (s, 1H).

If not specified, all the compounds in the following experiments were formulated with 5% Cremophor®EL (BASF), 5% Tween 80 (sigma-aldrich), and 90% phosphate buffer (pH 7.4), including the vehicles used for oral and injection administration.

Experiment 1: Detection of the Activity of Compounds to Inhibit the Production of Reactive Oxygen Species Mitochondrial reactive oxygen species-induced oxidative stress is the source of many diseases. This experiment is used to test whether the carbonyl-containing cyclic compounds provided by the present invention can reduce the production of reactive oxygen species. HEK 293T cells were divided into 96-well plates at 5000 cells per well, cultured in a 37° C. carbon dioxide incubator with serum-free Duchenne's Modified Eagle's Medium (DMEM) for 6 hours, and then representatives for compounds listed in Table 2 and 3 were added to a final concentration of 0, 0.1, 0.3, 1, 3, 10, 30 micromole/L, with each concentration in triplicate. After 18 hours of incubation, the reactive oxygen species detection kit (ROS-Glo™ $H_2O_2$ Assay) and the GloMax microplate fluorescence detector (Promega, USA) were used to detect reactive oxygen species production. At the same time, pioglitazone was used as a control. The amount of fluorescence is positively related to the production of reactive oxygen species. A three-parameter Sigmoid function curve was used to fit the obtained data. The abscissa represents the logarithmic value of the concentration, and the ordinate represents the percentage of reduced reactive oxygen species production relative to those of the control. Then EC50 value was calculated with professional software.

The experimental results showed that, compared to the DMSO control, one old drug rosiglitazone can inhibit up to 58% of the active oxygen production, and its EC50 is 2.5 micromole/L; another old drug pioglitazone can inhibit the active oxygen production of up to 42%, and its EC50 is 0.7. micromole/L; ELB00824 can inhibit the production of reactive oxygen species by up to 45%, and its EC50 is 1.5 micromole/L. The lower the EC50 value, the stronger the ability to inhibit the production of reactive oxygen species is. Therefore, in terms of the EC50, the ability of ELB00824 and the old drug pioglitazone are close, both of which are stronger than the old drug rosiglitazone. The EC50s of representatives for compounds listed in Table 2 (i.e., ELB00824, ELB00727, ELB00702, ELB00993, ELB001045, ELB001046, ELB001115, ELB001125, ELB001201, ELB001090), Table 3 (i.e., ELB00825) of the present invention are less than 10 micromole/L, indicating that these new compounds have the properties to inhibit the production of reactive oxygen species. In addition to ELB00824, the EC50s of some of these compounds were less than 3 micromole/L, such as those of ELB00824, ELB00727, ELB00702, ELB00993, ELB001045, ELB001115, ELB001125, ELB001201, ELB001203 and ELB001090, indicating that they have a higher ability to inhibit the production of reactive oxygen species, and thus they have the potential to treat oxidative stress-related diseases, including, but not limited to, neurological disorders and strokes, inflammation and immune diseases, metabolic diseases, kidney diseases.

Experiment 2: Detection of the Blood-Brain Barrier Permeability of Compounds

The blood-brain barrier permeability of carbonyl-containing cyclic compounds is determined in in vivo studies.

Healthy male rats used in the study were divided into compound group and control group. Representatives for compounds listed in Table 2, and Table 3, and pioglitazone and rosiglitazone, was diluted into the concentration of 10 mg/kg, and intraperitoneally injected into animals at 10 mg/kg body weight with each dose in triplicate. Rats were anesthetized 0.5, 1, 2, 4, 6, 10, 24 hour after administration of ELB00824, pioglitazone and rosiglitazone, or 1 hour after administration of other compounds. The brains were dissected, heated immediately at boiling water for 2 min, homogenized with methanol, and centrifuged. The upper layer was collected and dried under vacuum to remove solvents, and then resuspended in methanol. The above samples are filtered through a 0.45 micron nylon membrane, and then 20 microL of sample were load into a high-performance liquid chromatographic (HPLC) system (Model LC-16P, Shitnadzu, Japan) to perform quantitative analysis. For pioglitazone and rosiglitazone, the mobile phases consisted of 0.1% trifluoroacetic acid in water (solvent A) and 0.1% trifluoroacetic acid in acetonitrile (solvent B). For ELB00824, the mobile phases consisted of 75% methanol and 0.4% acetic acid in water (solvent A), and 50% acetonitrile, 37.5% methanol, 12.5% tetrahydrofuran, 0.4% acetic acid in acetonitrile (solvent B). To monitor analyte peak elution, the fluorescence detector (Model RF-20AXS, Shimadzu, Japan) was set to an emission wavelength of 247 nm with excitation at 367 nm for rosiglitazone, and the UV detector (Model SPD-16, Shimadzu, Japan) was set to a wavelength of 240 nm to 269 nm for other compounds. Statistical analysis of the linear regression curve of standard compound solutions of different concentrations showed that the fluorescence detection method has a good linear relationship with the fluorescence peak area in the solubility range of 0.1 micromole/L to 1000 micromole/L of the compounds ($r^2=0.99$).

FIG. 1 shows the results of measurement for the compounds (e.g., ELB00824 as an example) in rat brain. Area under the compound concentration-time curve (AUC) represents the compound bioavailability. For ELB00824, the peak brain concentration ($C_{max}$), time to maximum brain concentration (Tmax), AUC from zero hour to 6 hours or 24 hours after administration ($AUC_{0-6h}$ and $AUC_{0-24h}$, respectively) are 16.4 micromole/L (4830 nanogram/mL), 2 hours, 18706 ng·h/mL and 31517 ng·h/mL. For pioglitazone, $C_{max}$, $T_{max}$, $AUC_{0-6h}$ and $AUC_{0-24h}$ is 2.2 micromole/L (740 nanogram/mL), 1 hour, 1506 ng·h/mL and 3522 ng·h/mL, respectively. For rosiglitazone, Cmax, Tmax, $AUC_{0-6h}$ and $AUC_{0-24h}$ is 1.4 micromole/L (504 nanogram/mL), 1 hour, 774 ng·h/mL and 1933 ng·h/mL, respectively. Therefore, the $C_{max}$, $AUC_{0-6h}$ and $AUC_{0-24h}$ of ELB00824 is 7, 12 and 9 times those of pioglitazone, respectively, and is 10-12, 24 and 16 times those of rosiglitazone, respectively. This showed that the peak concentration and bioavailability of the old drug pioglitazone in the brain is higher than those of the old drug rosiglitazone. The peak concentration and bioavailability of the ELB00824 in the brain are significantly higher (i.e., an order of magnitude higher) than those of the old drug rosiglitazone and pioglitazone, indicating that the blood-brain barrier permeability of ELB00824 is far better than the PPARγ agonists currently approved for use on the market.

The experimental results also showed that the $C_{max}$ and $AUC_{0-6h}$ of representatives for compounds listed in Table 2 and Table 3 of the present invention were more than three times those of pioglitazone, indicating that their blood-brain permeabilities have been greatly improved. The $C_{max}$ and $AUC_{0-6h}$ of representatives for compounds listed in Table 2 and Table 3 were more than 5 and 8 times those of pioglitazone, respectively. These compounds include ELB001080, ELB001045, ELB00984, ELB001044, ELB001046, ELB001058, ELB001115, ELB001116, ELB001084, ELB001201, ELB001057, indicating that the blood-brain barrier permeabilities of these compounds are far better than the PPARγ agonists currently approved for use on the market. Therefore compounds listed in Table 2 and Table 3 have the potential to treat PPARγ agonist-related diseases, including, but not limited to, neurological disorders and strokes, inflammation and immune diseases, metabolic diseases, kidney diseases.

Experiment 3: The In Vitro Transcriptional Activity of PPARγ Gene Induced by the Compounds In this experiment, the PPARγ gene was used as target gene to detect the in vitro transcription activity of the compounds. The compounds of interest were detected was first dissolved with dimethyl sulfoxide (DMSO). After adding dissolved compound to the cell culture medium, the volume of DMSO did not exceed 0.5%. First two plasmids were constructed: PPARγ protein expression plasmid and luciferase reporter plasmid. They are both from the lentiviral plasmid pLV-CMVIE-ZsGreen-Puro, whose DNA sequence contains the cytomegalovirus immediate early (CMVie) promoter, ZsGreen and Puro dual reporter. The PPARγ expression plasmid pLV-CMVIE-PPAR□-ZsGreen-Puro was constructed by cloning full-length coding sequences of the pertinent receptors into pHBLV-CMVIE-ZsGreen-Puro vector. To construct the luciferase (luc) reporter plasmid pLV-PPRE-luc-ZsGreen-Puro, the CMVie promoter in plasmid pHBLV-CMVIE-ZsGreenPuro was first replaced by a peroxisome proliferator responsive element (PPRE) containing fragments comprised the nucleotide sequence 50-GTCGACAGGGGACCAGGACAAAGGT-CACGTTCGGGAGTCGAC, repeated four times in tandem, to generate a new plasmid, at a multiple cloning site of which the luc gene was then inserted. The sequence is from reference 7: (Gijsbers L, et al. Stable reporter cell lines for peroxisome proliferator-activated receptor γ (PPARγ)-mediated modulation of gene expression. Anal Biochem, 2011, 414(1): 77-83). The compounds used for screening are representatives for compounds listed in Table 2, and Tables 3 of the present invention. In the meantime, rosiglitazone and pioglitazone were used as controls. HEK 293 T cells were grown at 37° C. and 5% $CO^2$. Cells were distributed in 10-cm tissue culture plates at a density of 5.5 million cells per plate, and then transfected with the luciferase reporter plasmid (6 nanogram/plate) and the PPARγ expression plasmid (18 nano gram/plate). Cells were cultured for 6 hours. Renew the DMEM medium containing 10% FBS, and continue cultivation for 18 hours. Renew the DMEM medium containing 10% FBS again, and continue cultivation for 24 hours. Then the cells were distributed in 96-well plates at a density of 20,000 cells per well. After incubation for 6 h, compounds or control with different concentration were placed into each well, resulting in the finical concentration of 0.1, 0.3, 1, 3, 10, and 30 millimole/L with each concentration in triplicate. Twenty-one hours later, promoter activation was detected by the addition of SteadyLite (PerkinElmer, Waltham, Mass.) and GloMax 96 Microplate Luminometer (Promega, Madison, Wis.). The amount of Luminometer emitted from each well is positively correlated with the expression of PPARγ gene. A three-parameter Sigmoid function curve was used to fit the obtained data. The abscissa represents the logarithmic value of the concentration, and the ordinate represents the percentage of PPARγ gene activation relative to those of the control. Then EC50 value was calculated with professional software, which is the concentration of a carbonyl-containing cyclic compound that can cause 50% activation, where 100% activation should be induced by 1 micromole/L of the positive control (N-(2-chlorophenyl)-1H-indole-3-carboxamide). In Statistical analysis, the coefficient of variation is used to measure the robustness and repeatability of the experiment. An analysis of variance (ANOVA) and Dunnett post hoc comparison test are used to compare the significance of the differences between different groups of data. The difference is significant with $P<0.05$. EC50 is a parameter of its activity. The lower the EC50 value, the higher the activity of corresponding compound.

The results showed that the EC50s of pioglitazone and rosiglitazone were 22.1 and 6.5 micromole/L, respectively, and the EC50 values of representatives for compounds listed in Table 3 of the present invention were close to or higher than those of rosiglitazone. The EC50 value of representatives for compounds listed in Table 2 was lower than those of rosiglitazone (6.4 micromole/L). These compounds include ELB00532, ELB00702, ELB00727, ELB00824, ELB00827, ELB00993, ELB001080, ELB001045, ELB001046, ELB001090, ELB001115, ELB001116, ELB001125, ELB001203 and ELB001201. In particular, the EC50 value of some compounds were very low, e.g., ELB00702 (3.1 micromole/L), ELB00824 (4.7 micromole/L), ELB01045 (3.5 micromole/L), ELB001090 (3.9 micromole/L), ELB001115 (4.8 micromole/L), ELB001201 (5.8 micromole/L), indicating that compounds listed in Table 2 of the present invention can induce transcriptional activity of PPARγ gene in vitro, and their activities are stronger than the old PPARγ agonists on the market.

Experiment 4: The In Vitro Transcriptional Activity of Klotho Gene Induced by the Compounds Klotho is an important downstream gene of PPARγ pathway. The following experiments tested the properties of the compounds in Table 2 and 3 to activate the klotho gene in vitro. First, a stable cell line, KL-Luc, was constructed. The klotho gene carried by the cell line retained the DNA sequence of klotho gene promoter, but the coding sequence of the klotho gene was replaced with luciferase. KL-Luc fragment includes a promoter sequence of the klotho gene (a DNA region of 18,000 base pairs in length upstream of the transcription start site of the gene) and a luciferase-encoding sequence. To construct the KL-Luc sequence containing lentiviral vector, the KL-Luc fragment was cloned into the pDONR vector using BP recombinase, so that the target fragment had attL recombination sites on both sides. Then the KL-Luc fragment was transferred from the pDONR vector to a lentiviral vector (without exogenous promoter) pLenti6/BLOCK-IT-DEST. The constructed lentiviral vector of the target fragment was then transfected into HEK293T cells, and then the KL-Luc gene lentiviral expression vector and the packaginanogram/helper plasmid were co-transfected into HEK293T cells to perform lentiviral packaging. The virus was harvested, and virus titer was calculated. And the lentivirus was used to infect target cells. The stable strains were screened by adding drugs. Finally, monoclonal cell lines were selected from polyclonal cells by cell cloning. The effective luciferase expression of each monoclonal cell line was determined by quantitative polymerase chain reaction (qPCR). The inventors chose a third monoclonal cell line (KL-Luc-3) to continue the compound screening. The compounds of interest were the compounds in Table 2 and 3. At the same time, rosiglitazone and pioglitazone were used as a control. KL-Luc-3 cells were divided into 96-well plates at 5000 cells in 80 microL per well, cultured in a 37° C. carbon dioxide incubator with serum-free Duchenne's Modified Eagle's Medium (DMEM) for 6 hours, and then the compounds were added to a final concentration of 0, 0.1, 0.3, 1, 3, 10, 30 micromole/L, with each concentration in triplicate. After 16 hours of incubation, the SteadyLite (PerkinElmer, Waltham, Mass.) and the GloMax Microplate Luminometer (Promega, USA) were used for quantitation of luciferase activity. The amount of luminescence emitted from each well is positively related to the transcriptional activity of the klotho promoter. A three-parameter Sigmoid function curve was used to fit the obtained data. The abscissa represents the logarithmic value of the concentration, and the ordinate represents the percentage of the activity relative to those of the control. Then EC50 value was calculated with professional software, which is the concentration of a carbonyl-containing cyclic compound that can cause 50% activation, where 100% activation should be induced by 1 micromole/L of the positive control (N-(2-chlorophenyl)-1H-indole-3-carboxamide). In Statistical analysis, the coefficient of variation is used to measure the robustness and repeatability of the experiment. An analysis of variance (ANOVA) and Dunnett post hoc comparison test are used to compare the significance of the differences between different groups of data. The difference is significant with P<0.05. EC50 is a parameter of its activity. The lower the EC50 value, the higher the activity of corresponding compound.

Figure 2:
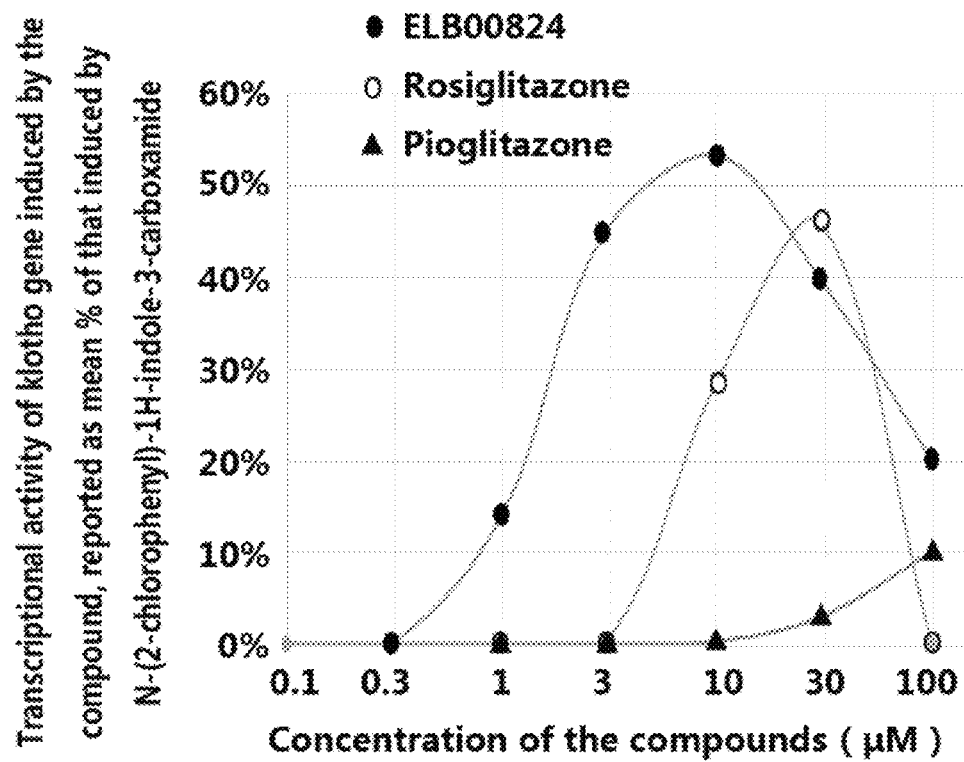
FIG. 2 shows the effects of the carbonyl-containing cyclic compounds provided by the present invention on inducing the transcriptional activities of klotho gene in vitro.

FIG. 2 shows the results for these compounds (including ELB00824). The results showed that the EC50s of ELB00824 was 1.5 micromole/L, which is ⅙, and less than 1/67 those of rosiglitazone and pioglitazone, respectively. Therefore, the ELB00824-induced transcriptional activity of klotho gene is 6 and more than 66 folds those of rosiglitazone and pioglitazone, respectively. The experimental results also showed higher transcriptional activity of klotho gene induced by representatives for compounds listed in Table 2 and Table 3 of the present invention with all EC50s less than 20 micromole/L. The EC50s of some compounds, such as ELB00532, ELB00702, ELB00727, ELB00827, ELB00993, ELB001045, ELB001046, ELB001090, ELB001115, ELB001116, ELB001125, ELB001201, ELB001203 were less than that of rosiglitazone (9.7 micromole/L). Furthermore, The EC50s of ELB00702, ELB00727, ELB00993, ELB001046, et al, were less than 3 micromole/L. This that the transcriptional activities of klotho gene induced by these compounds exceed those of PPARγ agonists currently approved for use on the market. Therefore, compounds in Tables 2 and Table 3 of the present invention have the potential to treat PPARγ or klotho-related diseases, including, but not limited to, neurological disorders and strokes, inflammation and immune diseases, metabolic diseases, cardiovascular diseases, kidney diseases, skin diseases (including skin aging and damage), and cancer.

Experiment 5: The In Vivo Brain Transcriptional Activity of Klotho and PPARγ Gene Induced by the Compounds The compounds in the present invention were proposed to activate PPARγ in vivo, which in turn increases the transcriptional activity of the downstream gene klotho, indicated by the mRNA level of the mouse brain klotho gene. The higher the mRNA level, the higher the in vivo brain transcriptional activity of the compound. To verify this hypothesis, adult male Kunming mice were used in the experiments. Representatives for compounds listed in Table 2, and 3, rosiglitazone or pioglitazone, were formulated and injected into tail vein at a dose of 10 mg/kg body weight/day for 10 or 30 days with each dose in triplicate. The injection volume is 8 ml/kg body weight. Dimethyl sulfoxide (DMSO) was used as a vehicle control of the compounds. After 30 days, mice were killed, brain tissue was removed and the total RNA was extracted by the Trizol method. The RNA was then reverse-transcribed to the cDNA, and quantified by SYBR Green fluorescence quantitative PCR kit (HaiGenc) and a quantitative PCR system (Bio-Rad MinOpticon Type 2) were used for real-time fluorescent quantitative polymerase chain reaction (RT-PCR). The mouse gene primers were design as follows:

```
KLOTHO-forward
5'-TTGCTGGGTTCCCTTTGTGAGGAA-3';

LOTHO-reverse
5'-AACCACTGAGCCAGACTCCAACAT-3';
```

```
GAPDH-forward
5'-TTCCGTGTTCCTACCCCCAATG-3';

GAPDH-reverse
5'-TGCCTGCTTCACCACCTTCTT-3'.
```

The results of RT-PCR experiments were semi-quantitatively corrected using the expression of GAPDH gene as an internal reference. Data analysis was performed using the $2^{-\Delta\Delta ct}$ method. Semi-quantitative values of gene expression were then normalized by the control mean.

The test results showed that, after 10 days of continuous injection, the mRNA level of klotho gene activated by representatives for compounds listed in Table 2 and Table 3 of the present invention in the brain of the mouse is more than twice that of the vehicle control group, and these compounds include ELB00532, ELB00702, ELB00727, ELB00824. ELB00827, ELB00993, ELB001045, ELB001046, ELB001090. ELB001115, ELB001116, ELB001125, and ELB001201, while no change of brain mRNA levels was detected in the old drugs rosiglitazone and pioglitazone treated mice. Therefore, the in vivo transcriptional activity of klotho gene induced by representatives for compounds listed in Tables 2 and 3 are higher than those of rosiglitazone and pioglitazone. After 30 days of continuous injection, the mRNA level of klotho gene activated by some compounds such as ELB00532, ELB00702, ELB00727, ELB00824, ELB00827, ELB00993, ELB001045, ELB001046, ELB001115, ELB001116, and ELB001125 is more than 5 times that of the vehicle control group, while no change of brain mRNA levels was detected in the old drugs rosiglitazone and pioglitazone treated mice, indicating the in vivo transcriptional activity of klotho gene induced by these compounds are higher than those of PPARγ agonists now approved for use on the market. Therefore, compounds in Tables 2 and Table 3 of the present invention have the potential to treat PPARγ or klotho-related diseases, including, but not limited to, neurological disorders and strokes, inflammation and immune diseases, metabolic diseases, cardiovascular diseases, kidney diseases, skin diseases (including skin aging and damage), and cancer.

Experiment 6: The Effectiveness of the Compounds for Treating Neurological Disorders, as in the Case of (1) Alzheimer's Disease Alzheimer's disease is a common type of neurological disorder. This experiment uses the learning and memory function of an animal model of Alzheimer's disease as a platform for evaluating the effectiveness of the compounds for treating neurological disorders. The method was as follows: Five-month-old male APP/PS1 transgenic mice (double transgenic mice expressing a chimeric mouse/human amyloid precursor protein with Swedish mutations (K595N/M596L) and a mutant human presenilin 1 (PS1-dE9)) and non-transgenic mice of the same age (from Beijing Huafukang Biotechnology Co., Ltd.) were used in the experiment. The treatment lasted for a total of 30 days. The compounds was dissolved in DMSO and mixed into food pellets. The animals were given ad libitum access to the pellets. The mice were divided into the following 6 groups with 12 mice in each group, including: (1) healthy control group, where non-transgenic mice were fed with normal chow, (2) disease control group, where APP/PS1 transgenic mice were fed with normal chow, (3) rosiglitazone group, where APP/PS1 transgenic mice were fed with rosiglitazone (10 mg/kg body weight/day); (4) ELB00727 group, where APP/PS1 transgenic mice were fed with carbonyl-containing cyclic compound ELB00727 (10 mg/kg body weight/day); (5) ELB00824 group, where APP/PS1 transgenic mice were fed with a carbonyl-containing cyclic compound ELB00824 (10 mg/kg body weight/day); and (6) donepezil group, where APP/PS1 transgenic mice were fed with donepezil (3 mg/kg body weight/day) as the positive control.

No any side effect, or significant body weight changes, or significant dietary changes were found during the administration. A common indicator used in academia in memory and dementia experiments is the number of errors in the water maze (reference memory). More errors mean poorer memory. On the last 3 days of dosing, eight-arm radial water maze was used by experimenters who were blind to drug treatment. As a classic experimental instrument, to detect slight deficits in learning and memory, the eight-arm water maze is more sensitive than not only Morris maze, but also Six-arm radial water maze. For details, see reference 8: Alamed J et al. Two-day radial-arm water maze learning and memory task; robust resolution of amyloid-related memory deficits in transgenic mice [J], Nature Protocols 2006, 1(4): 1671-1679. This experiment uses an eight-arm water maze built in accordance with the above literature. The eight-arm water maze is placed in a basin with an interior diameter of 102 cm. Each arm measures 30 cm long, 14.5 cm wide, and 40 cm high. Escape platform is located at the end of one of the arms. In the reference memory version of the task described here, the goal arm is held constant for all trials, with a different start arm on successive trials. On day one, mice received 12 trials, with trials alternating between visible and hidden platform. On day 2 and 3, mice received 12 additional trials but the platform was kept hidden throughout the trials. Entry into an incorrect arm was scored as a spatial reference error. Errors were averaged into three trial blocks, with four blocks per day, e.g., the first block (the 1st to 3rd trial), the second block (the 4th to 6th trial), and so on. A total of 30 trials can be divided into 10 blocks. The line charts were made with the number of blocks as the abscissa and the average of the number of errors as the ordinate. At the end of the experiments, the cerebral cortex and hippocampus of the mice were removed, RNA was extracted, and the expression of many genes was analyzed by semi-quantitative RT-PCR. An analysis of variance (ANOVA) and Dunnett post hoc comparison test are used to compare the significance of the differences between different groups of data. The difference is significant with P<0.05.

Figure 3:
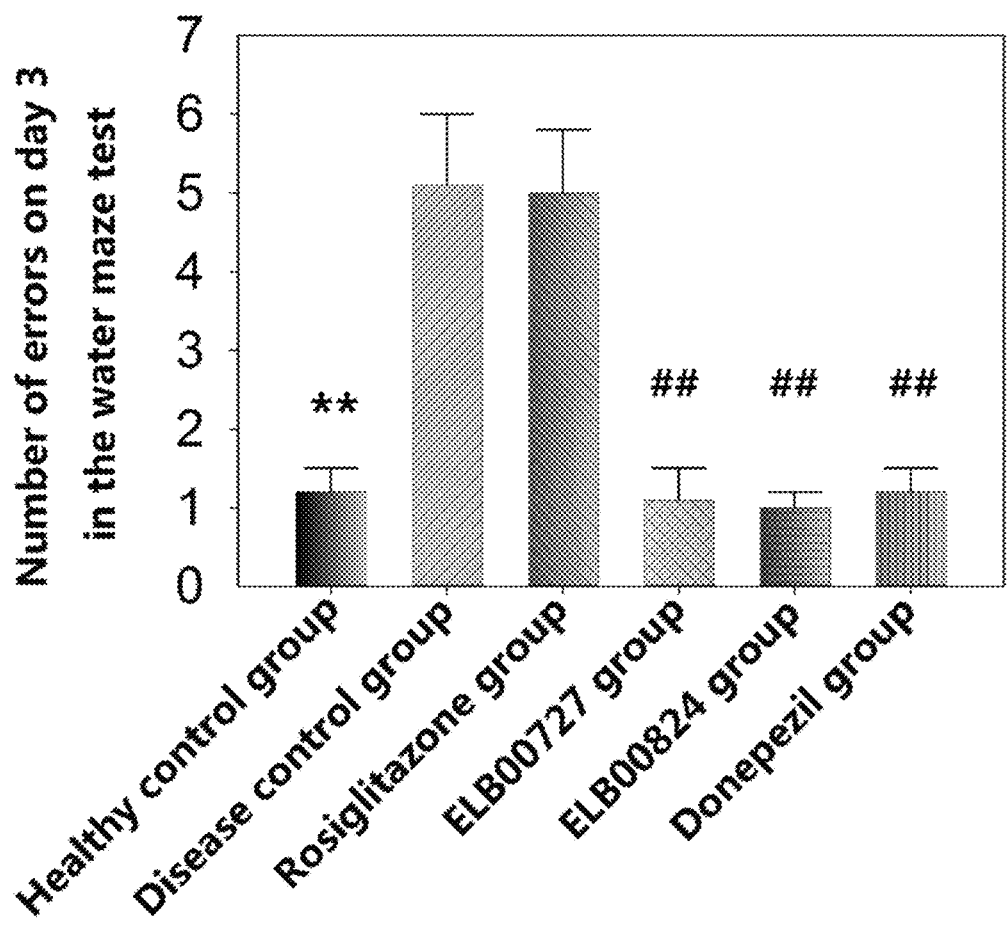
FIG. 3 shows the therapeutic effects of carbonyl-containing cyclic compounds provided by the present invention on Alzheimer's disease.

The result of the number of errors in three days (reference memory) is shown in FIG. 3. In the third day, compared with that in the first day, a significant reduction in the number of errors indicated normal learning and memory function, while a non-significant reduction in the number of errors indicated memory deficits. The experimental results on the third day, compared with that on the first day, showed that 1) the number of errors in the healthy control group was reduced significantly (** in the figure indicated P<0.01), while the number of errors in the disease control group was not reduced significantly, indicating that the transgenic mice in the disease control group have memory deficits; 2) the reduction in the number of errors was not significant for Rosiglitazone group, indicating that this old PPARγ agonist has no effect on restoring memory function, probably because it is difficult to penetrate the blood-brain barrier; 3) the reduction in the number of errors was significant for ELB00727 group, ELB00824 group and Donepezil group (## in the figure indicated P<0.01), and the number of errors (i.e., 5) on the first day was reduced to close to 1 on the third day, indicating that these compounds can restore memory function. The anti-dementia efficacy of these compounds is unique among PPARγ agonists, because it is much stronger than those of the old PPARγ agonists.

In order to investigate the etiology of the therapeutic effect of ELB00824, the changes in expression levels of important genes involved in etiology in the cerebral cortex and hippocampus were measured after compound administration, and compared with those before administration. Compared with that of the disease control group, significant increase of the expression levels of the following genes was detected; include the klotho gene (9 folds), the antioxidant MnSOD and Prx-2 genes (tripled or quadrupled), Gng11 gene (tripled). GluN2B gene (doubled), and Bcl-xl gene that inhibits apoptosis on the outer membrane of mitochondria (doubled). Therefore, the results demonstrated that the expression levels of these neuroprotective genes in the ELB00824 group were significantly higher than those in the disease control group, indicating that the etiology of ELB00824 anti-dementia effects involves the improvement of the abovementioned various neuroprotective mechanisms in the brain, and thus ELB00824 can treat both manifestation and root cause of the disease. None of the abovementioned gene expression levels in donepezil group was significantly increased, indicating that the donepezil as a clinically used anti-dementia drug, treat only the symptoms but not the root cause.

Using to the same method as above, the anti-dementia properties of other representatives for compounds listed in Table 2 and Table 3 of the present invention were also evaluated. The results showed that the number of errors in water maze on the third day for these compounds were comparable to that of ELB00824, especially for ELB00825, ELB001080, ELB001045, ELB001046, ELB001115, ELB001116, and ELB001125. After experiments of these compounds, the mRNA level of some neuroprotective genes in the animal brain, such as the klotho gene, MnSOD gene were determined, and found that these compounds induced significantly higher gene expression levels than that of the vehicle group, supporting the therapeutic potentials of compounds listed in Table 2 and Tables 3 on Alzheimer's disease.

Experiment 7: The Effectiveness of the Compounds for Treating Neurological Disorders, as in the Case of (2) Parkinson's Disease Parkinson's disease is also a common type of neurological disorder. This experiment uses an animal model of Parkinson's disease as a platform for evaluating the effectiveness of the compounds for treating neurological disorders. The method was as follows:

Injection of MPTP-HCl (1-methyl-4-phenyl-1,2,3,6-tetrahydropyridine hydrochloride) is a method commonly used in academia to establish Parkinson's disease model mice. Three month-old male wild type mice were used in the experiment. The treatment lasted for a total of 35 days. The mice were divided into the following 5 groups with 12 mice in each group, including: (1) healthy control group, where mice were intraperitoneally injected with vehicle daily; (2) disease control group, where mice were intraperitoneally injected with a vehicle daily; (3) rosiglitazone group, where mice were intraperitoneally injected with rosiglitazone (5 mg-kg body weight); (4) ELB00824 group, where mice were intraperitoneally injected with carbonyl-containing cyclic compound ELB00824 (5 mg/kg body weight); (5) ELB00727 group, where mice were intraperitoneally injected with carbonyl-containing cyclic compound ELB00727 (5 mg/kg body weight). In addition, mice of group (2) to (5) were intraperitoneally injected with MPTP-HCl at 25 mg/kg body weight and with probenecid at 250 mg/kg body weight every 3.5 days. For all abovementioned groups. Motor skills were assessed on the 36th to 40th days after compound administration. Beam traversal test is a method commonly used in academia to detect movement coordination in animals with Parkinson's disease. The beam was constructed according to the following Reference 9: Fleming S M, et al., Early and Progressive Sensorimotor Anomalies in Mice Overexpressing Wild-Type Human α-Synuclein [J], J of Neuroscience 2004, 24: 9434-9440. The mice were first trained for 2 consecutive days, and taught to trained to traverse the length of the beam. On the day of the test, a mesh grid (1 cm squares) of corresponding width was placed over the beam surface leaving a 1 cm space between the grid and the beam surface. Animals were then videotaped while traversing the grid-surfaced beam for a total of five trials. An error was counted when, during a forward movement, a forelimb or hindlimb slipped through the grid. The number of errors made per step (referred to as "error per step scores") was counted. An analysis of variance (ANOVA) and Dunnett post hoc comparison test are used to compare the significance of the differences between different groups of data. The difference is significant with $P<0.05$.

Figure 4:
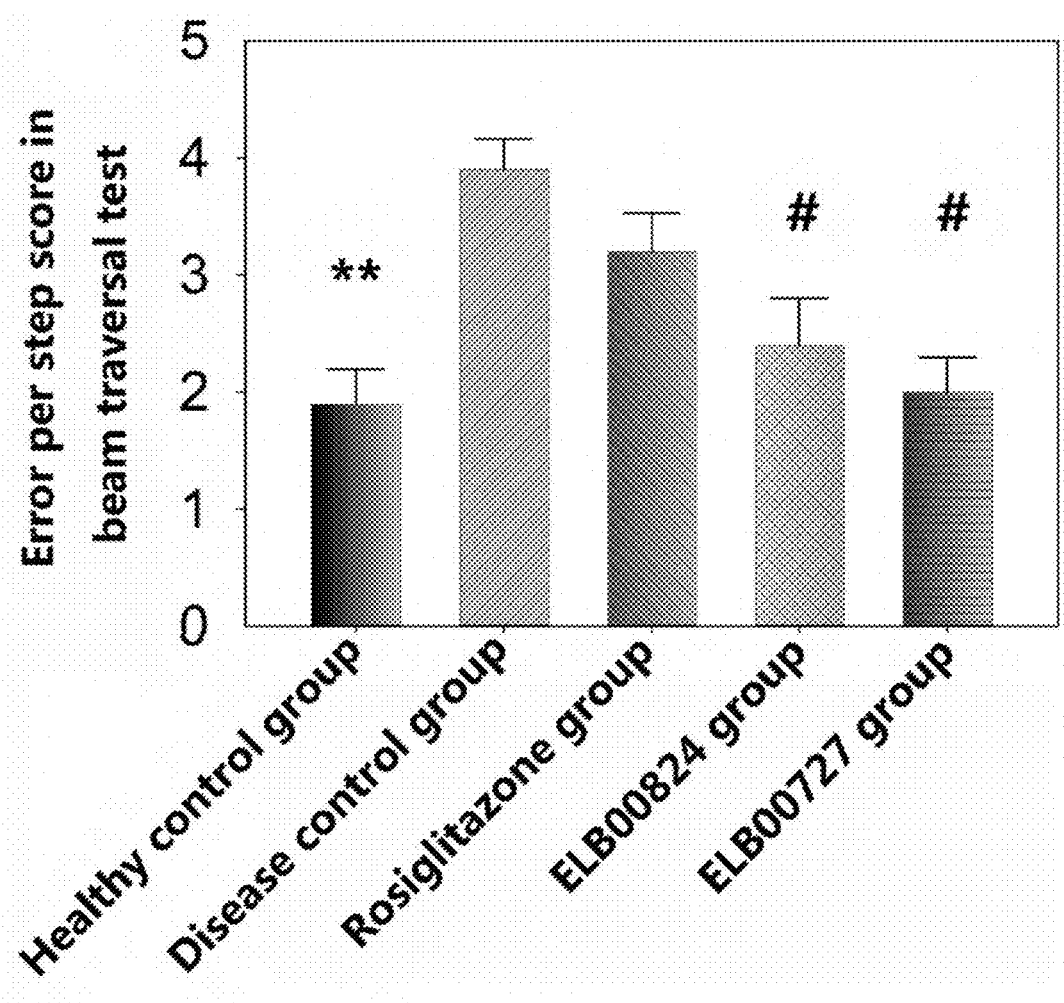
FIG. 4 shows the therapeutic effects of carbonyl-containing cyclic compounds provided by the present invention on Parkinson's disease.

The calculated errors per step scores were showed in FIG. 4. The higher scores, the poorer the coordination of the movement. Compared with disease control group, the results showed that 1) the error per step in the healthy control group was significantly lower (** in the figure indicated $P<0.01$), indicating better coordination of the movement for the healthy control group, and poorer coordination of the movement for the disease control group; 2) the reduction in the number of errors per step was not significant for Rosiglitazone group, indicating that this old PPARγ agonist has no effect on restoring movement coordination, probably because it is difficult to penetrate the blood-brain barrier; 3) the reduction in the number of errors per step was significant for ELB00727 group and ELB00824 group p (## in the figure indicated $P<0.01$), indicating that these compounds can restore movement coordination. The anti-Parkinson's disease efficacy of these compounds is unique, because it is much stronger than those of the old PPARγ agonists.

Using to the same method as above, the anti-Parkinson's disease properties of other representatives for compounds listed in Table 2 and Table 3 of the present invention were also evaluated. The results showed that compared with disease control group, the error per step in the group treated by these compounds was significantly lower, and the efficacies on restoring movement coordination for these compounds were comparable to those of ELB00824 and ELB00727. The abovementioned compounds include ELB00825, ELB001045, ELB001046, ELB001115, ELB001116, and ELB001125. In conclusion, we found that compounds in Table 2 and Table 3 show efficacies on restoring movement coordination. The anti-Parkinson's disease efficacy of these compounds is unique among PPARγ agonists, because it is much stronger than those of the old PPARγ agonists.

Experiment 8: The Effectiveness of the Compounds for Treating Neurological Disorders, as in the Case of (3) a Type of Neuropathic Pain Called Trigeminal Neuralgia This experiment uses an animal model of a special type of neuropathic pain, i.e., trigeminal neuralgia, as a platform for evaluating the effectiveness of the carbonyl containing cyclic compounds for treating neurological disorders. A common rat model of trigeminal neuralgia is a chronic compression injury model (CCI) caused by ligation of the infraorbital nerve (IoN). In the present study, an improved rat model of trigeminal neuropathic pain was used, in which CCI is induced by ligation of distal segment of IoN (dIoN). Wild type male Sprague-Dawley rats with body weight 250 to 260 grams underwent dIoN-CCI surgery experiments. The mechanical threshold of pain in rats without surgery experiments will exceed 6 grams. If the dIoN-CCI surgery is successful, it will reduce the pain threshold to less than 2 grams.

The mice were divided into the following 11 groups with 4 to 5 mice in each group. The formulation used for transdermal treatment is cream. The cream formulation contains miglyol 812, cetyl alcohol, glycerol monostearate, oleyl alcohol, stearyl alcohol, carbopol, sodium cetostearyl sulphate, benzyl alcohol, and citric acid. The compound administration of each group starts on the third day after successful dIoN-CCI surgery. The groups include: (1) oral vehicle group, where animals were gavaged with vehicle; (2) oral pioglitazone group, where animals were gavaged with pioglitazone (300 mg/kg body weight); (3) oral ELB00824 group, where animals were gavaged with ELB00824 (1 mg/kg body weight); (4) oral ELB00824 group, where animals were gavaged with ELB00824 (3 mg/kg body weight); (5) oral ELB00824 group, where animals were gavaged with ELB00824 (10 mg/kg body weight); (6) oral ELB00824 group, where animals were gavaged with ELB00824 (20 mg/kg body weight); (7) oral gabapentin group, where animals were gavaged with gabapentin (1 mg/kg body weight, a commonly used neuropathic painkiller) as a positive control; (3) oral ELB00824 group, where animals were gavaged with ELB00824 (1 mg/kg body weight); (8) IP vehicle group, where animals were intraperitoneally injected with vehicle; (3) IP ELB00824 group, where animals were intraperitoneally injected with ELB00824 (20 mg/kg body weight); (10) Transdermal vehicle group, where the formulation is the vehicle cream, which is evenly spread on a whisker pad with an area of 0.7 $cm^2$ and a dose of 100 $mg/cm^2$, (11) Transdermal ELB00824 group, where a cream containing 7% ELB00824 is evenly spread on a whisker pad with an area of 0.7 $cm^2$ and a dose of 100 $mg/cm^2$. The method for detecting rat facial hypersensitivity is performed using Von Frey filaments. An analysis of variance (ANOVA) and Dunnett post hoc comparison test are used to compare the significance of the differences between different groups of data. The difference is significant with $P<0.05$. For detailed methods of the dIoN-CCI surgery and pain evaluation, see the reference 10: Ding W, et al. An improved rodent model of trigeminal neuropathic pain by unilateral chronic constriction injury of distal infraorbital nerve. J Pain 2017; 18: 899-007.

The results of oral treatment groups of different compounds are as follows: in oral ELB00824 group, the mechanical pain threshold before CCI ligation (9±3 g) is not significantly different from the threshold 2 hours (8.9±2 g) after oral treatment with ELB00824 (10 mg/kg body weight), indicating that oral ELB00824 has a significant anti-allodynic effect. The mechanical threshold of 4.9±0.9 g at 2 hours after oral administration of pioglitazone (300 mg/kg body weight) in the oral pioglitazone group was similar to that of 4.2±0.8 g at 2 hours after oral administration of ELB00824 (3 mg/kg body weight) threshold in an oral ELB00824 group, indicating that the minimum effective anti-allodynic dose (3 mg/kg) of ELB00824 is equivalent to 1% of the minimum effective anti-allodynic dose of pioglitazone (300 mg/kg), which means that the anti-allodynic properly of ELB00824 is about 100 times stronger than that of pioglitazone. Note that for pioglitazone, the dose of 300 mg/kg body weight in rats has greatly exceeded its safe dose (i.e., 4.7 mg/kg body weight in rats, converted from 45 mg/60 kg or 0.75 mg/kg body weight in humans, based on normalization of dose to body surface area). Therefore there is no therapeutic window for pioglitazone.

At the time of administration, no side effect was found in all ELB00824 (a carbonyl-containing cyclic compound) group, while the gabapentin group showed drowsiness. The anti-allodynic effect in the ELB00824 group (10 mg/kg) was last for 2 hour. While the anti-allodynic effect in the gabapentin group was only last for 1 hour, much shorter than that of ELB00824, and disappeared at 2 hours after drug administration. Therefore, the carbonyl-containing cyclic compounds of the present invention have great application potential, due to fewer side effects, longer duration of efficacy, and far higher efficacy than traditional PPAR agonists. In contrast, there is no therapeutic window for traditional PPAR agonists, which thus are lack of practical application value.

The comparison results of different administration routes were as follows: for the rats with body weight approximately 250 grams, 5 mg of ELB00824 was administered at 20 mg/kg body weight through three different routes, by which rats were divided into the following three groups: oral ELB00824 group, IP ELB00824 group, transdermal ELB00824 group. After 1 hour of administration, the mechanical pain thresholds induced by different routes of administration are in the order of transdermal (19.8±3.1 g)>IP (12.8±2.2 g)>oral (6.8±1.9 g). When the appearance of anti-allodynic effect is defined as the time when the mechanical threshold is increased to 10 grams and above, the duration of anti-allodynic effect provide by transdermal administration (2.3 hours) is longer than that of IP administration (1.8 hours), and much longer than that of oral administration (0.7 hours). The time (2.3 hours) for the drug to exert anti-allodynic effect (the pain threshold is maintained above 10 grams) is longer than the time for abdominal injection (1.8 hours) and much longer than the time for oral administration (0.7 hours). These data indicated that under the same dosage, the efficacy and duration of anti-allodynic effect provide by transdermal administration is the highest and longest, respectively.

The compound in the abovementioned fifth group (oral ELB00824 group, 10 mg/kg) were then substituted with other representatives for compounds listed in Table 2 and Table 3 of the present invention, and at 2 hours after oral administration (10 mg/kg), their anti-allodynic effects were evaluated. It was found that the other representatives for compounds listed in Table 2 and Table 3 of the present invention also have anti-allodynic properties similar to ELB00824, among which the anti-allodynic properties of the following compounds are stronger (i.e., pain threshold greater than 4.9 g): ELB00825, ELB001080, ELB001045, ELB001046, ELB001115, ELB001116, ELB001125, etc. In conclusion, compounds listed in Table 2 and Table 3 of the present invention have good anti-allodynic potentials, which is much better than those of the old PPARγ agonists.

Experiment 9: The Effectiveness of the Compounds for Treating Neurological Disorders, as in the Case of (4) a Type of Neuropathic Pain Called Diabetic Peripheral Neuropathy This experiment uses an animal model of a special type of neuropathic pain, i.e., diabetic peripheral neuropathy as a platform for evaluating the effectiveness of the carbonyl containing cyclic compounds for treating neurological disorders. The method was as follows: A detailed method for constructing a mouse model of peripheral neuropathy induced by type 2 diabetes can be found in reference 11: Shi T J, et al. Coenzyme Q10 prevents peripheral neuropathy and attenuates neuron loss in the db$^-$/db$^-$ mouse, a type 2 diabetes model [J]. PNAS USA 2013, 110: 690-695. Male 5-6 week-old male db$^-$/db$^-$ mice were used in the experiment, and their normoglycemic heterozygous littermates were used as controls, db$^-$/db$^-$ is a commonly used type 2 diabetes animal model. The compounds was dissolved in DMSO and mixed into food pellets. The animals were given ad libitum access to the pellets, beginning from 8 to 9 weeks of age for 10 weeks. The mice were divided into the following 5 groups with 10 mice in each group: (1) ELB00824 group, where db$^-$/db$^-$ mice were fed with ELB00824 at 10 mg/kg body weight/day; (2) ELB001116 group, where db$^-$/db$^-$ mice were fed with ELB001116 at 10 mg/kg body weight/day; (3) pregabalin group, where db$^-$/db$^-$ mice were fed with pregabalin at 30 mg/kg body weight/day; (4) disease control group, where db$^-$/db$^-$ mice were fed with normal chow; (5) healthy control group, where the heterozygous littermates were fed with normal chow. The method for detecting mice hindlimb hypersensitivity is performed using Von Frey filaments. An analysis of variance (ANOVA) and Dunnett post hoc comparison test are used to compare the significance of the differences between different groups of data. The difference is significant with $P<0.05$. The increase of mitochondrial reactive oxygen species (ROS) in the sciatic nerve of mice, which in turn leads to the increase of intracellular malondialdehyde (MDA), is the etiology of this type of neuropathic pain. The efficacy of compound to treat the root cause of the disease was evaluated by measurement of the levels of MDA and mitochondrial ROS from the sciatic nerves.

The experimental results showed that there is no difference in the mechanical pain thresholds, ROS lewis and MDA levels of the above five groups of 8-9 week old mice, but after 10 week treatment, the mice have the following differences: (1) The pain thresholds of the disease control group is more than double that of the healthy control group, indicating that the db$^-$/db$^-$ mice experience pain symptoms at the end of treatment; (2) There is no difference in mechanical threshold between ELB00824 group, ELB001116 group, pregabalin group and normal control group, indicating that ELB00824, ELB001116 and pregabalin can relief the pain symptoms; (3) The levels of ROS and MDA in the disease control group were significantly higher than those in the healthy control group, indicating that db$^-$/db$^-$ mice had nerve damage at the end of treatment. (4) There was no difference in levels of ROS or MDA between ELB00824, ELB001116 and healthy control groups, indicating that both ELB00824 and ELB001116 can treat nerve damage in db$^-$/db$^-$ mice. However, there was no difference in the levels of ROS or MDA between pregabalin group and disease control group, and both were significantly higher than that of healthy control group, indicating that pregabalin could not treat the nerve damage in db$^-$/db$^-$ mice, and could not treat the root cause (i.e., nerve damage) of this type of neuropathic pain. Therefore, these data indicated that ELB00824 and ELB001116 can treat both manifestation and root cause of the disease, while old neuropathic painkiller treat only the symptoms but not the root cause.

Using to the same method as above, the properties of anti-diabetic peripheral neuropathy of other representatives for compounds listed in Table 2 and Table 3 of the present invention were also evaluated. The results showed that the anti-allodynic effects for these compounds were comparable to those of ELB00824 and ELB001116, significantly improved the mechanical pain threshold, and reduced the levels of ROS and MDA in the animals of interest. The representative compounds include ELB00825, ELB001080, ELB001045, ELB001046, ELB001115, and ELB001125. In conclusion, compounds listed in Table 2 and Table 3 of the present invention also have good therapeutic potentials to treat both pain symptom and the root cause, which is much better than those of the old neuropathic painkillers.

Experiment 10: The Effectiveness of the Compounds for Treating Cancers

Due to the unique properties of the compounds provided by the present invention to cross the blood-brain barrier, this experiment uses mouse model of brain cancer as a platform for evaluating the effectiveness of the compounds for treating cancers.

Malignant astrocytic glioma is the most common primary brain tumors, and the median overall survival of the most malignant variant glioblastoma is poor. The method of this experiment was as follows: Male wild mice from Beijing Huafukang Biotechnology Co., Ltd. were used. The treatment lasted for a total of 30 days. The compounds was dissolved in DMSO and mixed into food pellets. The animals were given ad libitum access to the pellets. The mice were divided into the following 5 groups with 8 mice in each group: (1) healthy control group, where animals were fed with normal chow; (2) disease control group, animals fed with normal chow; (3) rosiglitazone group, where animals fed with rosiglitazone at 5 mg/kg body weight/day; (4) ELB00727 group, where animals gavaged with carbonyl-containing cyclic compound ELB00727 at 5 mg/kg body weight/day; (5) ELB00824 group, where animals gavaged with carbonyl-containing cyclic compound ELB00824 at 5 mg/kg body weight/day. In addition, mice of group (2) to (5) were implanted with tumor cells before the compounds administration. Before implantation, LN-229 cells (Nanjing Kebai Biological Technology Co., Ltd.) were cultured in Dulbecco's Modified Eagle Medium (DMEM) with 10% fetal calf serum, trypsinized, concentrated, and resuspended in DMEM to the finial concentration of 100,000 cells/microL. The mice were anesthetized and placed in a stereotactic frame. A hole was drilled in the cranium, and cells were injected into the striatum. Two microL of tumor cells were injected at a depth of 3.5 mm. Thereafter, the skull was cleaned and the incision sutured. Compound administration was started 4 days after surgery. For all abovementioned groups, no any side effect, or significant body weight changes, or significant dietary changes were found during the administration. All animals were sacrificed after 30 days after initiation of treatment. Total brains were serially sectioned at 10 micrometer using a cryostat, and sections were H&E stained. Images of H&E sections containing tumors were captured with a camera using a 1× objective and images processed using NIH J Image 1.62 software (Bethesda, Md., USA). The tumor area of each section was measured. The area was then multiplied by the section thickness (10 micrometer section) to achieve a section volume measurement. Volumes of all sections were added to calculate the total volume of each tumor. An analysis of variance (ANOVA) and Dunnett post hoc comparison test are used to compare the significance of the differences between different groups of data. The difference is significant with $P<0.05$.

Figure 5:
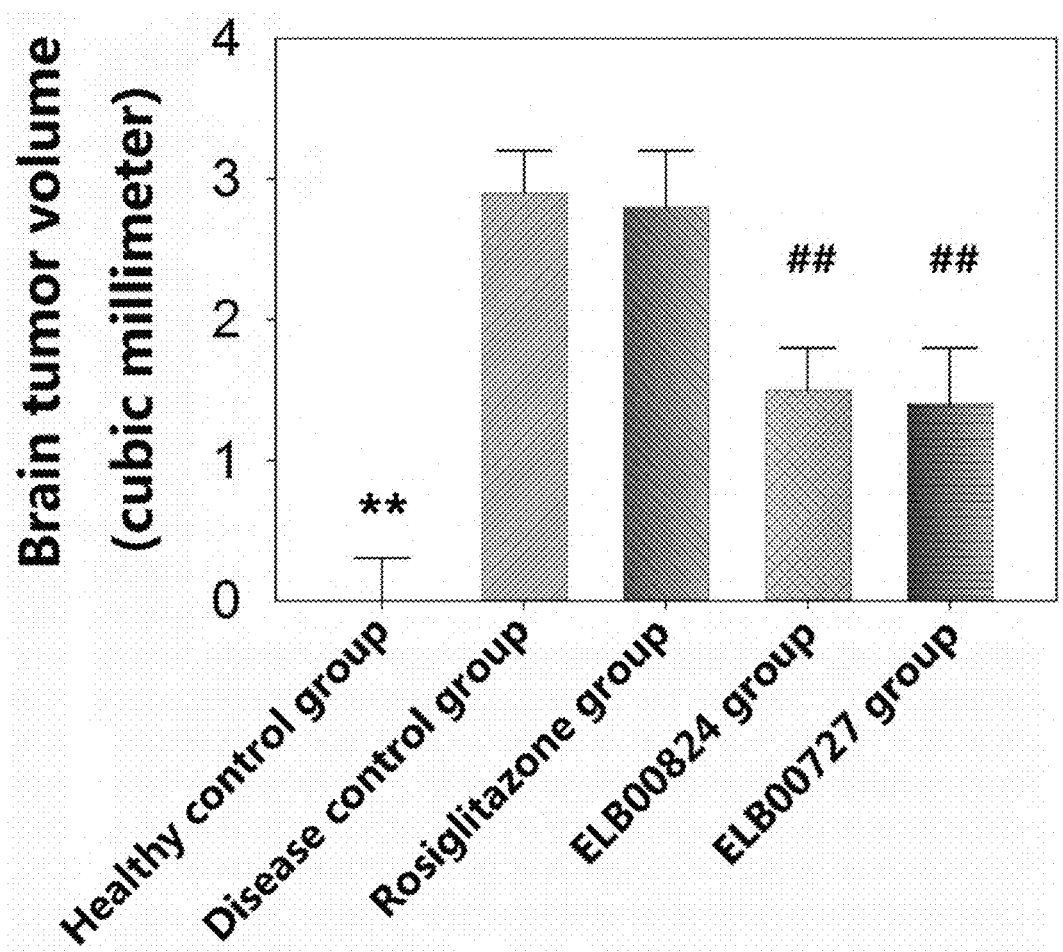
FIG. 5 shows the therapeutic effects of carbonyl-containing cyclic compounds provided by the present invention on brain cancer.

The experiment results were shown in FIG. 5. Compared with that of the disease control group, no significant difference in tumor volume at 30 days could be observed in the rosiglitazone group, indicating that old PPARγ agonists have no therapeutic effect, probably because it is difficult to penetrate the blood-brain barrier; however, animals in the ELB00727 group and ELB00824 group showed significant tumor volume reduction, indicating good effectiveness of the compounds for treating brain cancer. The anti-cancer efficacy of these compounds is unique among PPARγ agonists, because it is much stronger than those of the old PPARγ agonists.

Using to the same method as above, the properties of anti-cancer of other representatives for compounds listed in Table 2 and Table 3 of the present invention were also evaluated. The results showed that the anti-cancer effects for these compounds were comparable to those of ELB00727 and ELB00824. Compared with that of the disease control group, animals treated with these compounds showed significant tumor volume reduction, indicating good effectiveness of the compounds for treating brain cancer. The anti-cancer efficacy of these compounds is unique among PPARγ agonists, because it is much stronger than those of the old PPARγ agonists.

Experiment 11: The Effectiveness of the Compounds for Treating Kidney Diseases, Metabolic Diseases, Inflammation and Immune Diseases This experiment uses a rat model of hyperglycemia-induced nephropathy as a platform for evaluating the effectiveness of the compounds for treating kidney diseases, metabolic diseases, inflammation and immune diseases. The method was as follows:

Wild type Sprague-Dawley rats were used. The compounds was dissolved in DMSO and mixed into food pellets. The animals were given ad libitum access to the pellets. The animals were divided into the following 4 groups with 8 animals (body weight of 200 to 450 grams) in each group, including: (1) healthy control group, where animals were fed with normal chow; (2) disease control group, where animals were fed with normal chow; (3) ELB00727 group, where animals were fed with carbonyl-containing cyclic compound ELB00727 (5 mg/kg body weight/day); (4) ELB00824 group, where animals were fed with carbonyl-containing cyclic compound ELB00824 (5 mg/kg body weight/day). In addition, 3 days before compound treatment, the animal of group 2 to 4 were given a single intraperitoneal injection of streptozotocin, and 3 days later, blood glucose levels were measured from tail veins using a glucose meter. Animals with blood glucose levels above 500~650 milligrams per deciliter were considered as hyperglycemia and were used for further study. No any side effect, or significant body weight changes, or significant dietary changes were found during the administration. After 90 days after initiation of treatment, blood pressure values were measured with the tail cuff system. The day before the kidneys were harvested, animals were placed in metabolic cages for 24 h for urine collection, and albumin to creatinine ratio (ACR) was measured. Animals were then fasted for 12 hours and sacrificed under anesthesia with a 10% chloral hydrate solution (0.3 g/kg). Serum samples were isolated and biochemical parameters were analyzed with by enzyme colorimetry in an automatic analyzer (Roche) to determine the FBG (fasting blood glucose) level (unit millimole/L). In addition, fasting insulin (FINS) levels, where the units are milliIU/L, were determined by enzyme-linked immunosorbent assay (ELISA) method with anti-rat insulin antibodies, and TNF-α was detected by rat tumor necrosis factor-α (TNF-α) ELISA kit (BD). An analysis of variance (ANOVA) and Dunnett post hoc comparison test are used to compare the significance of the differences between different groups of data. The difference is significant with P<0.05.

Figure 6:
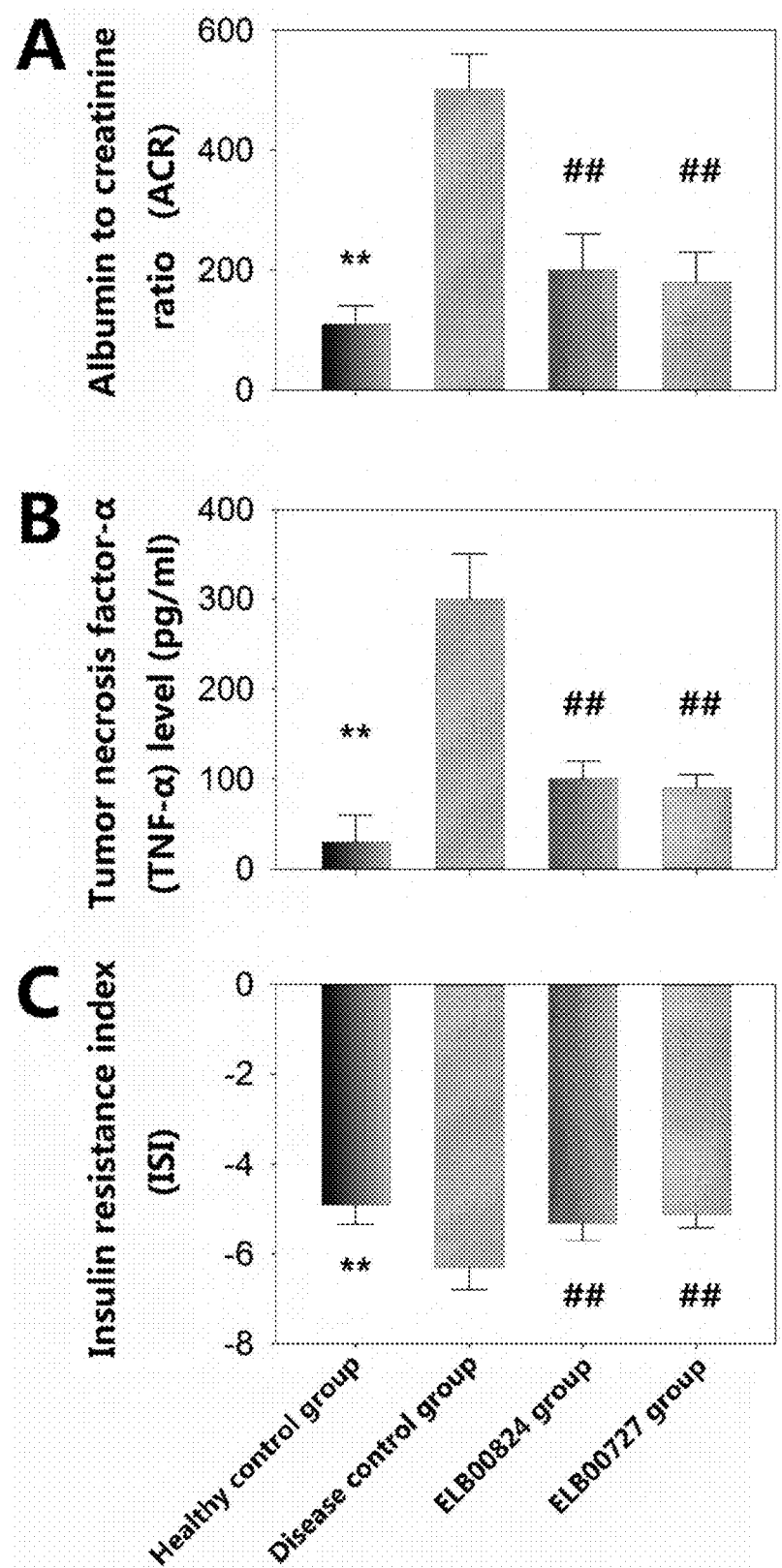

Effectiveness for treating kidney diseases: Urine albumin to creatinine ratio (ACR) is a sensitive and reliable indicator for the diagnosis of early kidney disease. The higher the ACR value, the more severe kidney injury is. The experiment results were shown in FIG. 6A. Compared with that of the healthy control group, animals in the disease group showed significant ACR increase ( in the figure indicated P<0.01), indicating hyperglycemia induced kidney injury; compared with that of the disease control group, animals in the ELB00727 group and ELB00824 group showed significant ACR reduction ( in the figure indicated P<0.01), indicating the hyperglycemia induced kidney injuries were mitigated by the administration of carbonyl-containing cyclic compounds ELB00727 and ELB00824.

Effectiveness for treating inflammation and immune diseases: Tumor necrosis factor-α is a typical cytokine that can promote inflammation, which is mainly secreted by macrophages. The higher the blood TNF-α level, the more severe the inflammation is. The experiment results were shown in FIG. 6B. Compared with that of the healthy control group, animals in the disease group showed significant TNF-α level increase ( in the figure indicated P<0.01), indicating severe inflammation; compared with that of the disease control group, animals in the ELB00727 group and ELB00824 group showed significant TNF-α level reduction ( in the figure indicated P<0.01), indicating the anti-inflammation effects of carbonyl-containing cyclic compounds ELB00727 and ELB00824.

Effectiveness for treating metabolic diseases: Type 2 diabetes is a common metabolic disease, where one of its major etiology is insulin resistance. Insulin works like a key that opens the door of cells to glucose transport into cells. However, after the occurrence of insulin resistance, insulin does not work well, the glucose retains in the blood and cannot enter the cells, and it will eventually cause persistent high blood sugar, a typical indicator of insulin resistance. The insulin resistance index (ISI) is an important indicator for assessing the degree of insulin resistance. See reference 12: Li G W, et al. A new insulin-sensitivity index for the population-based study [J]. Zhonghua Nei Ke Za Zhi 1993, 32(10): 856-660. The index is calculated by the formula: ISI=ln(FBG*FINS). The lower the ISI value, the stronger the insulin resistance is, and the more severe the diabetes onset is. The experiment results were shown in FIG. 6C. Compared with that of the healthy control group, animals in the disease group showed significant ISI reduction ( in the figure indicated P<0.01), indicating severe diabetes onset; compared with that of the disease control group, animals in the ELB00727 group and ELB00824 group showed significant ISI increase ( in the figure indicated P<0.01), indicating the decreased insulin resistance and marked alleviation in diabetes by the administration of carbonyl-containing cyclic compounds ELB00727 and ELB00824.

Using to the same method as above, the effectiveness of other representatives for compounds listed in Table 2, and Table 3 of the present invention were also evaluated. The results showed that the effectiveness of the compounds for treating kidney diseases, metabolic diseases, inflammation and immune diseases were comparable to those of ELB00727 and ELB00824. Compared with those of the disease control group, animals treated with these compounds showed significant ACR and TNF-α level reduction, and significant ISI increase, indicating good effectiveness of the compounds for mitigating hyperglycemia induced kidney injuries, reducing inflammation, decreasing insulin resistance and alleviating diabetes.

The embodiments described herein are provided to illustrate the invention and do not limit the scope thereof. It will be readily apparent to one skilled in the art that varying substitutions and modifications can be made which are meant to be encompassed by the spirit and scope of the invention.

INDUSTRIAL APPLICATIONS

The present invention provides novel compounds as PPARγ agonists capable of inhibiting the production of mitochondrial reactive oxygen species and/or having high blood-brain barrier permeability, and a preparation method thereof, and the compounds can be used as medicaments for the prevention and treatment of related diseases and is suitable for industrial applications.

What is claimed is:

1. A PPARγ agonist of formula (I) or pharmaceutically acceptable salts, solvates, or prodrugs thereof:

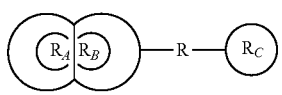

(I)

wherein:
sum of nitrogen and oxygen (referred as "(N+O)") in the formula (I) together with all its substituents is limited to 1, 2 or 3;
the formula (I) and all its substituents do not contain diacety, or α-hydroxy ketone, thiazolidinedione, oxazolidinedione or sulfonyl;
$R_A$—$R_B$ is

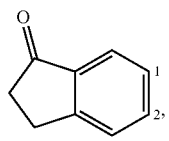

(A)

wherein $R_A$ is the carbonyl containing cyclic ring in the structure (A); $R_B$ is the phenyl in the structure (A), and $R_B$ is optionally substituted by 0 to 3 $R^b$;
R is connected to the $R_A$—$R_B$ with the carbon atom on the phenyl only at position 1 or 2 as a connecting position;
R is $C_{4-6}$ alkyl, or $C_{4-6}$ alkenyl;
$R_C$ is phenyl, thiophene, 1H-pyrrole, pyridyl, furan, or 1,3-thiazole, optionally substituted by 0, 1, 2, 3 $R^c$;
wherein following groups are excluded from formula (I), $R^b$, and $R^c$: quaternary ammonium, carboxyl, carboxylate, thiazolidinedione, phosphono, phosphate, sulfino, sulfo, carbothioic S-acid, carbothioic O-acid, carbodithioic acid, sulfhydryl when the pKa in water is lower than 7.4, or amine when the pKa in water is higher than 7.4;

the molecular weight of the formula (I) is less than 400 Dalton; the molecular weight of $R^b$ or $R^c$ is less than 200 Dalton; and the number of carbons in $R^b$ or $R^c$ is no more than 10;

if $R_C$ is phenyl, 1H-pyrrole or thiophene, $R^b$, and $R^c$ can be independently selected from hydroxyl, hydrogen, $C_{1-6}$ alkyl, $C_{2-8}$ alkenyl, $C_{2-8}$ alkynyl, $C_{3-10}$ aryl, halo, halogenated $C_{1-8}$ alkyl, halogenated $C_{1-6}$ alkoxy, amine when the pKa in water is not higher than 7.4, imine, nitrile, isonitrile, pyridyl, $C_{1-6}$ alkylthio, $C_{1-6}$ alkoxy, $C_{1-6}$ alkoxyl $C_{1-6}$ alkyl, sulfhydryl when the pKa in water is not lower than 7.4, sulfide, disulfide, carbonothioyl, carbodithio, thiocyanate, thionoester, borinate, borino, phosphino, or combination thereof as long as the total (N+O) in all $R^b$, and $R^c$ together is 0 or 1;

if $R_C$ is pyridyl, furan, or 1,3-thiazole, $R^b$, and $R^c$ can be independently selected from hydrogen, $C_{1-6}$ alkyl, $C_{2-8}$ alkenyl, $C_{2-8}$ alkynyl, $C_{3-10}$ aryl, halo, halogenated $C_{1-8}$ alkyl, sulfhydryl when the pKa in water is not lower than 7.4, sulfide, disulfide, carbonothioyl, carbodithio, borinate, borino, phosphino, and combinations thereof as long as the combinations thereof are not containing any nitrogen or oxygen;

and wherein any alkyl or alkenyl groups thereof can be linear or branched.

2. A PPARγ agonist, or pharmaceutically acceptable salts, solvates, or prodrug thereof, wherein the PPARγ agonist is selected from the group consisting of:
(E)-6-(4-(4-ethylphenyl)but-1-en-1-yl)-2,3-dihydro-1H-inden-1-one;
(E)-6-(4-(4-ethylphenyl)but-1-en-1-yl)-5-fluoro-2,3-dihydro-1H-inden-1-one;
(E)-6-(4-(4-ethylphenyl)but-1-en-1-yl)-5-(18F)fluoro-2,3-dihydro-1H-inden-1-one;
(E)-6-(4-(4-methoxyphenyl)but-1-en-1-yl)-2,3-dihydro-1H-inden-1-one;
(E)-6-(4-(5-ethylpyridin-2-yl)but-1-en-1-yl)-2,3-dihydro-1H-inden-1-one;
(E)-6-(4-(3-methoxyphenyl)but-1-en-1-yl)-2,3-dihydro-1H-inden-1-one;
(E)-6-(6-(4-ethylphenyl)hex-1-en-1-yl)-2,3-dihydro-1H-inden-1-one;
6-((1E)-4-(3-ethylphenyl)but-1-en-1-yl)-2,3-dihydro-1H-inden-1-one;
6-((1E)-5-(2-methyl-5-phenyl-1H-pyrrol-1-yl)pent-1-en-1-yl)-2,3-dihydro-1H-inden-1-one;
6-((1E)-4-(4-phenoxyphenyl)but-1-en-1-yl)-2,3-dihydro-1H-inden-1-one;
6-((1E)-4-(4-benzylphenyl)but-1-en-1-yl)-2,3-dihydro-1H-inden-1-one; and
6-(4-(4-ethylphenyl)butyl)-2,3-dihydro-1H-inden-1-one.

3. The PPARγ agonist according to claim 2, wherein the PPARγ agonist is selected from the group consisting of:
(E)-6-(4-(4-ethylphenyl)but-1-en-1-yl)-2,3-dihydro-1H-inden-1-one;
(E)-6-(4-(5-ethylpyridin-2-yl)but-1-en-1-yl)-2,3-dihydro-1H-inden-1-one;
(E)-6-(6-(4-ethylphenyl)hex-1-en-1-yl)-2,3-dihydro-1H-inden-1-one; and
6-(4-(4-ethylphenyl)butyl)-2,3-dihydro-1H-inden-1-one;
or pharmaceutically acceptable salts, solvates, or prodrugs thereof.

4. The PPARγ agonist according to claim 2, wherein the PPARγ agonist is selected from the group consisting of:
6-((1E)-4-(3-ethylphenyl)but-1-en-1-yl)-2,3-dihydro-1H-inden-1-one;

6-((1E)-5-(2-methyl-5-phenyl-1H-pyrrol-1-yl)pent-1-en-1-yl)-2,3-dihydro-1H-inden-1-one;

6-((1E)-4-(4-phenoxyphenyl)but-1-en-1-yl)-2,3-dihydro-1H-inden-1-one; and 6-((1E)-4-(4-benzylphenyl)but-1-en-1-yl)-2,3-dihydro-1H-inden-1-one;

or pharmaceutically acceptable salts, solvates, or prodrugs thereof.

5. A pharmaceutical composition comprising the PPARγ agonist of formula (I) according to claim 1, or pharmaceutically acceptable salts, solvates, or prodrugs, and a pharmaceutically acceptable carrier.

6. The pharmaceutical composition according to claim 5, wherein the composition is formulated into a dosage form selected from a group consisting of aqueous dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and immediate release formulations.

\* \* \* \* \*